United States Patent
Kumar et al.

(10) Patent No.: US 10,227,360 B2
(45) Date of Patent: Mar. 12, 2019

(54) COMPOUNDS FOR USE AS GPR120 AGONISTS

(71) Applicant: PIRAMAL ENTERPRISES LIMITED, Mumbai (IN)

(72) Inventors: Sanjay Kumar, Mumbai (IN); Rajiv Sharma, Mumbai (IN); Somnath Halder, Mumbai (IN); Sangameshwar Prabhakar Sawargave, Mumbai (IN); Vijaykumar Bhagwan Deore, Mumbai (IN)

(73) Assignee: Piramal Enterprises Limited, Mumbai (IN)

(*) Notice: Subject to any disclaimer, the term of this patent is extended or adjusted under 35 U.S.C. 154(b) by 0 days.

(21) Appl. No.: 15/117,430

(22) PCT Filed: Feb. 18, 2015

(86) PCT No.: PCT/IB2015/051232
§ 371 (c)(1),
(2) Date: Aug. 8, 2016

(87) PCT Pub. No.: WO2015/125085
PCT Pub. Date: Aug. 27, 2015

(65) Prior Publication Data
US 2016/0347768 A1 Dec. 1, 2016

Related U.S. Application Data

(60) Provisional application No. 61/941,794, filed on Feb. 19, 2014.

(51) Int. Cl.
*C07D 513/04* (2006.01)
*C07C 59/72* (2006.01)
*C07D 213/57* (2006.01)
*C07D 305/06* (2006.01)
*C07D 405/04* (2006.01)
*C07D 213/65* (2006.01)
*C07D 307/80* (2006.01)
*C07D 333/56* (2006.01)
*C07D 221/04* (2006.01)
*C07D 333/16* (2006.01)
*C07D 333/24* (2006.01)
(Continued)

(52) U.S. Cl.
CPC ............ *C07D 513/04* (2013.01); *C07C 59/72* (2013.01); *C07C 59/86* (2013.01); *C07C 255/46* (2013.01); *C07D 213/30* (2013.01); *C07D 213/57* (2013.01); *C07D 213/64* (2013.01); *C07D 213/65* (2013.01); *C07D 221/04* (2013.01); *C07D 239/26* (2013.01); *C07D 277/24* (2013.01); *C07D 277/60* (2013.01); *C07D 277/66* (2013.01); *C07D 285/12* (2013.01); *C07D 305/06* (2013.01); *C07D 305/08* (2013.01); *C07D 307/80* (2013.01); *C07D 333/16* (2013.01); *C07D 333/24* (2013.01); *C07D 333/56* (2013.01); *C07D 401/12* (2013.01); *C07D 405/04* (2013.01); *C07D 405/12* (2013.01); *C07D 409/12* (2013.01); *C07D 417/12* (2013.01); *C07D 513/06* (2013.01); *C07C 2601/02* (2017.05); *C07C 2601/04* (2017.05); *C07C 2601/10* (2017.05); *C07C 2601/14* (2017.05); *C07C 2601/16* (2017.05); *C07C 2602/06* (2017.05); *C07C 2602/08* (2017.05); *C07C 2602/10* (2017.05)

(58) Field of Classification Search
CPC ............................ C07D 513/04; C07D 333/24
USPC .......................................................... 514/303
See application file for complete search history.

(56) References Cited

U.S. PATENT DOCUMENTS 5,789,423 A 8/1998 Wakabayashi et al.
8,299,296 B2 10/2012 Shimada et al.
(Continued)

FOREIGN PATENT DOCUMENTS

CN 104046350 9/2014
EP 1688138 * 8/2006
(Continued)

OTHER PUBLICATIONS

Kwon et al., "Adipokines mediate inflammation and insulin resistance", Frontiers Endocrinol., 2013, 4: 1-11. PMID: 23781214.
(Continued)

*Primary Examiner* — Yong L Chu
(74) *Attorney, Agent, or Firm* — Foley & Lardner LLP

(57) ABSTRACT

The present invention relates to a compound of formula (I), or a tautomer, stereoisomer, geometrical isomer, prodrug, carboxylic acid isostere, solvate, polymorph, N-oxide, S-oxide or pharmaceutically acceptable salt thereof, which are GPR120 agonists. The present invention also relates to a pharmaceutical composition of a compound of formula (I) for the treatment of metabolic disorders, particularly Type 2 diabetes and associated diseases.

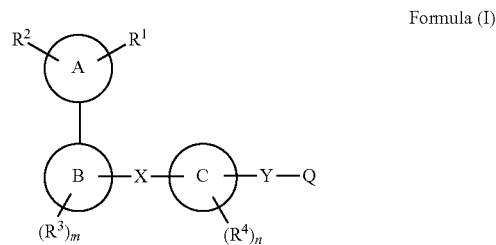

Formula (I)

28 Claims, No Drawings

(51) Int. Cl.

| | | |
|---|---|---|
| C07D 401/12 | (2006.01) | |
| C07D 239/26 | (2006.01) | |
| C07D 405/12 | (2006.01) | |
| C07D 409/12 | (2006.01) | |
| C07D 417/12 | (2006.01) | |
| C07D 277/24 | (2006.01) | |
| C07D 277/60 | (2006.01) | |
| C07D 277/66 | (2006.01) | |
| C07D 513/06 | (2006.01) | |
| C07D 285/12 | (2006.01) | |
| C07D 213/30 | (2006.01) | |
| C07D 305/08 | (2006.01) | |
| C07C 59/86 | (2006.01) | |
| C07C 255/46 | (2006.01) | |
| C07D 213/64 | (2006.01) | |

(56) References Cited

U.S. PATENT DOCUMENTS

| | | | |
|---|---|---|---|
| 8,367,708 | B2 | 2/2013 | Hashimoto et al. |
| 2011/0065739 | A1 | 3/2011 | Ishikawa et al. |
| 2011/0313003 | A1 | 12/2011 | Shi et al. |
| 2012/0115861 | A1 | 5/2012 | Calderini et al. |
| 2013/0217781 | A1 | 8/2013 | Carroll et al. |
| 2014/0069963 | A1 | 3/2014 | Stein |
| 2014/0275179 | A1* | 9/2014 | Sui ................ C07D 417/12 514/342 |
| 2017/0210731 | A1 | 7/2017 | Kumar et al. |
| 2017/0283410 | A1 | 10/2017 | Kumar et al. |

FOREIGN PATENT DOCUMENTS

| | | |
|---|---|---|
| EP | 1688138 A1 | 8/2006 |
| EP | 2125758 A1 | 12/2009 |
| GB | 990397 | 4/1965 |
| GB | 1139607 | 1/1969 |
| WO | WO-2005/086661 | 9/2005 |
| WO | WO 2008/103500 | 8/2008 |
| WO | WO 2009/038204 | 3/2009 |
| WO | WO-2009/054479 | 4/2009 |
| WO | WO 2010/008831 | 1/2010 |
| WO | WO 2010/048207 | 4/2010 |
| WO | WO 2010/080537 | 7/2010 |
| WO | WO 2010/104195 | 9/2010 |
| WO | WO 2011/072132 | 6/2011 |
| WO | WO-2011/159297 | 12/2011 |
| WO | WO-2013/128378 A1 | 9/2013 |
| WO | WO 2013/139341 | 9/2013 |
| WO | WO 2013/185766 | 12/2013 |
| WO | WO-2014/059232 | 4/2014 |
| WO | WO-2015/125085 | 2/2015 |
| WO | WO-2016/022446 | 2/2016 |

OTHER PUBLICATIONS

Kahn, S.E., "The importance of the beta-cell in the pathogenesis of type 2 diabetes mellitus", Am. J. Med., 2000, 108(6, Suppl 1):2S-8S.
PCT International Search Report and Written Opinion for Application No. PCT/IB2015/051232 dated May 18, 2015.
Talukdar et al., "Targeting GPR120 and other fatty acid sensing GPCRs ameliorates insulin resistance and inflammatory diseases", Trends Pharmacol. Sci., 2011, 32(9):543-550.
Wild et al., "Global prevalence of diabetes: estimates for the year 2000 and projections for 2030", Diabetes Care, 2004, 27(5):1047-1053.
Duncton et al., "Preparation of Heteroaryloxetanes and Heteroarylazetidines by Use of a Minisci Reaction", J. Org. Chem., (2009), 74(16):6354-6357.
Siddiqui et al., "BRET biosensor analysis of receptor tyrosine kinase functionality", Frontiers in Endocrinology, (2013), vol. 4, article 46, p. 1-11.

CAS Registry No. 1025918-57-3, STN Entry Date 6 Jun. 2008 3-(2-((2-(6-aminonaphthalen-2-yl)cyclopentyl)methoxy)phenyl)propanoic acid.
CAS Registry No. 1026475-19-3, STN Entry Date Jun. 8, 2008 2-[[2-[6-(carboxymethoxy)-2-naphthalenyl]cyclohexyl]methoxy]-benzenepropanoic acid.
CAS Registry No. 1026489-82-6, STN Entry Date Jun. 8, 2008 methyl 3-(2-((2-(6-aminonaphthalen-2-yl)cyclopentyl)methoxy)phenyl)propanoate.
CAS Registry No. 1026500-58-2, STN Entry Date Jun. 8, 2008 6-[2-[[2-(2-carboxyethyl)phenoxy]methyl]cyclohexyl]-2-naphthalenecarboxylic acid.
CAS Registry No. 1027427-54-8, STN Entry Date Jun. 11, 2008 2-[[2-(7-amino-2-naphthalenyl)cyclopentyl]methoxy]-benzenepropanoic acid.
CAS Registry No. 1027654-19-8, STN Entry Date Jun. 12, 2008 6-[2-[[2-(3-methoxy-3-oxopropyl)phenoxy]methyl]cyclohexyl]-2-naphthalenecarboxylic acid.
CAS Registry No. 1027894-93-4, STN Entry Date Jun. 13, 2008 2-[[2-(7-amino-2-naphthalenyl)cyclopentyl]methoxy]-benzenepropanoic acid methyl ester.
CAS Registry No. 1287459-87-3, STN Entry Date Apr. 29, 2011 rel-3-[[[(2R,3S)-2-(2-fluoro-5-methoxyphenyl)-6-oxo-3-piperidinyl]amino]methyl]-1H-indole-1-acetamide.
CAS Registry No. 1287467-25-7, STN Entry Date Apr. 29, 2011 rel-3-[[[(2R,3S)-2-(2-fluoro-5-methoxyphenyl)-6-oxo-3-piperidinyl]amino]methyl]-1H-indole-1-propanamide.
CAS Registry No. 1346947-23-6, STN Entry Date Dec. 1, 2011 3,4-dihydro-7-[[[(3R,4R)-4-[4-[3-[(2-methoxyphenyl)methoxy]propoxy]phenyl]-3-piperidinyl]oxy]methyl]-1(2H)-quinolineethanesulfonamide.
CAS Registry No. 1347559-94-7, STN Entry Date Dec. 2, 2011 3-[[[(2S,3S)-2-phenyl-3-piperidinyl]amino]methyl]-4-(2,2,2-trifluoroethoxy)-benzeneacetamide.
CAS Registry No. 1553145-75-7, STN Entry Date Feb. 23, 2014 5-[[[2-(1H-imidazol-1-yl)cyclopentyl]amino]methyl]-2-thiopheneacetic acid.
CAS Registry No. 1627272-79-0, STN Entry Date Sep. 28, 2014 methyl 2-(4-(((2-phenyltetrahydro-2H-pyran-3-yl)methyl)amino)-1H-pyrazolo[3,4-d]pyrimidin-1-yl)acetate.
CAS Registry No. 1645359-44-9, STN Entry Date Feb. 8, 2015 N-methyl-4-[[(2-phenylcyclopentyl)amino]methyl]-2-thiazoleacetamide.
CAS Registry No. 173160-56-0, STN Entry Date Feb. 13, 1996 [1S-(exo,exo)]-2-[[3-[4-[[(4-cyclohexylbutyl)amino]carbonyl]-2-oxazolyl]-7-oxabicyclo[2.2.1]hept-2-yl]methoxy]-benzeneacetic acid.
Guda et al., "An efficient synthesis of styryl 1,3,4-thiadiazoles using Lawesson's reagent and propylphosphonic anhydride-precursors for bis heterocycles", Arabian Journal of Chemistry (2014) 7, 947-954 (available online Aug. 29, 2014).
Marhraoui et al., "Synthese de nouveaux glycosyl-1,2,3-triazoles 1,4-disubstitues", J. Maroc. Chim. Hétérocyclique., 2010, 9(1):59-67. (No Abstract Available).
Muralkirishna et al., "Synthesis, antimicrobial and cytotoxic activities of sulfone linked bis heterocycles", European Journal of Medicinal Chemistry, 2012, 54:605-614.
National Diabetes Statistics Report (2014)(12 pages).
Padmaja et al., "Synthesis and antimicrobial activity of pyrrolyl/pyrazolyl arylaminosulfonylmethyl 1,3,4-oxadiazoles, 1,3,4-thiadiazoles and 1,2,4-triazoles", Chem. Pharm. Bull., 2011, 59(11)1509-1517.
Paulsen et al., "Expression of the Fatty Acid Receptor GPR120 in the Gut of Diet-Induced-Obese Rats and Its Role in GLP-1 Secretion", PLOS one, 2014, 9(2):e88227, pp. 1-6.
PCT International Search Report and Written Opinion for Application No. PCT/IB2015/055572 dated Jan. 21, 2016. (17 pages).
Reddy et al., "Synthesis and antioxidant activity of a new class of mono- and bis-heterocycles", Arch. Pharm. Chem. Life Sci., 2013, 346:154-162.
Reddy et al., "Synthesis and antioxidant activity of styrylsulfonylmethyl 1,3,4-oxadiazoles, pyrazolyl/isoxazolyl-1,3,4-oxadiazoles", Chem. Pharm. Bull., 2013, 61(12):1291-1297.

(56) References Cited

OTHER PUBLICATIONS

Shimpukade et al., "Discovery of a Potent and Selective GPR120 Agonist", J. Med. Chem., 2012, 55:4511-4515.
Suckow et al., "Alteration of the Glucagon Axis in GPR120 (FFAR4) Knockout Mice. A Role for GPR120 in Glucagon Secretion", J. Biol Chem., 2014, 289(22):15751-15763.
Concise Encyclopedia Chemistry (1993) Walter de Gruyter Berlin New York, pp. 872-873.
Vippagunta et al., "Crystalline solids", Advanced Drug Delivery Reviews, 2001;48:3-26.
CAS RN 536695-50-8; STN entry date: Jun. 24, 2003. 3-(4-aminobutyl)-2-[ I , I '-biphenyl]-4-yl-I H-indole-5-acetic acid.
CAS RN 536695-51-9; STN entry date: Jun. 24, 2003. 3-(4-aminobutyl)-2-[I ,I '-biphenyl]-2-yl-I H-indole-5-acetic acid.
Deng, G. et al, "Identification of benzoxazole analogs as novel, S1 P3 sparing SIP1 agonists", Bioorganic & Medicinal Chemistry Letters, 2012, vol. 22, pp. 3973-3977 Abstract; Compounds 16d, 16f, Table 3, p. 3976.
PCT International Search Report and Written Opinion for Application No. PCT/IB2015/056891 dated Mar. 7, 2016.

* cited by examiner

COMPOUNDS FOR USE AS GPR120 AGONISTS

CROSS-REFERENCE TO RELATED APPLICATIONS

This application is a U.S. national stage application of International Patent Application No. PCT/IB2015/051232, filed on Feb. 18, 2015, which claims priority to U.S. Provisional Application No. 61/941,794, filed on Feb. 19, 2014, the contents of each of these applications is incorporated herein by reference in their entirety.

FIELD OF THE INVENTION

The present invention relates to compounds of formula (I) (as described herein), processes for their preparation, pharmaceutical compositions comprising the compounds, and methods for their use for the prophylaxis and/or treatment of the diseases or disorders which are mediated by GPR120 receptor.

BACKGROUND OF THE INVENTION

Metabolic diseases or disorders are caused by an abnormal metabolic process and may either be congenital due to an inherited enzyme abnormality or acquired due to a disease of an endocrine organ or failure of a metabolically important organ such as the liver or the pancreas.

Among the metabolic disorders, diabetes mellitus is the most prevalent and is considered to be one of the five leading causes of death in the world (*Diabetes Care*, vol. 27, 2004, pp. 1047-1053). Diabetes mellitus is typically classified into two main subtypes: Type 1 and Type 2 diabetes mellitus. Type 1 diabetes mellitus (otherwise known as Insulin Dependent Diabetes Mellitus, IDDM), which generally occurs in adolescents under 20 years of age, is an autoimmune disease causing an insulitis with the subsequent destruction of insulin-producing β-cells of the pancreas. Further, in latent autoimmune diabetes in adults (LADA), β-cells are destroyed due to autoimmune attack. The subsequent lack of insulin leads to elevated levels of blood and urine glucose (hyperglycemia). Although the exact trigger for this autoimmune response is not known, patients with Type 1 diabetes have high levels of antibodies against pancreatic beta cells (hereinafter "beta cells"). However, it cannot be ascertained that all patients with high levels of these antibodies develop Type 1 diabetes. Type 2 diabetes mellitus or non-insulin-dependent diabetes mellitus (NIDDM) is developed when human muscle, fat and liver cells are not able to respond normally to insulin that body secretes. This inability to respond, otherwise known as insulin resistance, may be due to restriction on the numbers of insulin receptors on these cells, or a dysfunctional behaviour of signalling pathways within the cells, or both. Initially, the β-cells which are responsible for the production of insulin, compensate for this insulin resistance by increasing their insulin secretion. However, these cells gradually become unable to produce enough insulin to facilitate the normal glucose homeostasis, causing the progression to Type 2 diabetes (*Am J Med*. 108(6), Supplement 1, 2000, pp. 2S-8S). Type 2 diabetes (T2D) is characterised by fasting hyperglycemia which occurs as an effect of the combined lesions of insulin resistance and β-cell dysfunction. There are two types of defects associated with the β-cells: the first component, an increase in the basal insulin release which usually occurs in the presence of low, non-stimulatory glucose concentrations. The second component is a failure to enhance the insulin release in response to a hyperglycaemic challenge.

Obesity is another risk factor for developing metabolic diseases or disorders such as diabetes, cardiovascular disorders, hypertension, hyperlipidemia and an increased mortality. Diabetes caused by insulin resistance and obesity are part of the "metabolic syndrome" which is defined as the linkage between several diseases (also referred to as syndrome X, insulin-resistance syndrome, or deadly quartet). These often occur in the same patients and are major risk factors for the development of Type 2 diabetes and cardiovascular diseases (*Frontiers in Endocrinology*, vol. 4, 2013, pp. 1-11). It has been suggested that the control of lipid levels and/or glucose levels is required to treat type 2 diabetes and cardiovascular diseases. Even though lifestyle changes like exercise and healthy diet are regarded as the most efficient ways to prevent and manage the disease, pharmaceutical intervention is frequently necessary.

Current treatment options for diabetes, particularly T2D include use of hypoglycaemic agents and insulin. Metformin is one such hypoglycemic agent which is used in the treatment of Type 2 diabetes. It is, in fact, one of the oldest drugs used for the treatment of T2D and it still remains the drug of choice despite associated gastrointestinal (GI) side effects including anorexia, nausea, diarrhea and vomiting commonly associated with it. In fact, metformin should be used with caution in patients with renal impairment because of the slight risk of lactic acidosis. Sulfonylureas (SUs) e.g. glimepiride, glipizide, are insulin secretagogues, which act on β-cells to increase insulin release, are commonly used in the treatment of Type 2 diabetes. However, use of sulfonylureas is also associated with adverse effects in that they increase the risk of hypoglycaemia and lead to weight gain. Insulin treatment which is chosen by patients carries the same side-effects. Thiazolidinedione compounds e.g. rosiglitazone, pioglitazone, are insulin sensitizers which bind to peroxisome proliferator-activated receptors (PPARs) in cells and thereby increase the insulin sensitivity. Though, thiazolidinedione compounds have also been widely used, the enhanced risks of cardiovascular disease and hepatotoxicity have resulted in stringent limitations on their use. Relatively recently, regulatory authorities approved new classes of anti-diabetic agents such as GLP-1 agonists (exenatide and liraglutide) and DPP-4 inhibitors (linagliptin and alogliptin).

It is a known fact that metabolic processes are regulated by fatty acids which are important biological molecules that serve both as a source of energy and as signalling molecules. Generally, it is believed that fatty acids produce their biological effects through interacting with intracellular targets including, for example, the family of peroxisome proliferator-activated receptors (PPARs). However, in the recent years it has become clear that fatty acids also serve as agonists for a group of cell surface G protein-coupled receptors (GPCRs). Free fatty acids (FFAs) have been demonstrated to act as ligands of several GPCRs including GPR40 (FFAR1), GPR43, GPR84, GPR119 and GPR120. One of the GPCR namely GPR40 facilitates glucose-stimulated insulin secretion from pancreatic β-cells, whereas the other GPCR namely GPR120 regulates the secretion of glucagon-like peptide-1 (GLP-1) in the intestine, as well as insulin sensitivity in macrophages. GPR120 is localized to intestinal enteroendocrine cells, such as colonic L cells. Certain research studies conducted relative recently, identified that loss-of-function GPR120 human variant is associated with obesity, diabetes and other insulin resistance, and related metabolic disorders and also with inflammatory disorders. These findings establish GPR120 as a potential target for the treatment of diabetes, other metabolic disorders and also, inflammatory disorders (*Trends Pharmacol Sci.* vol. 32(9), 2011 pp. 543-550).

Thus, in view of the role of GPR120 receptor in potentiating metabolic disorders such as diabetes and also, inflammatory disorders, there is need in the art to develop compounds that act by modulating the GPR120 receptor pathways.

Various patent documents describe compounds which are reported to be GPR120 modulators. Examples of patent documents describing GPR120 modulators include PCT Application Publications WO2008103500, WO2009038204, WO2010008831, WO2010048207, WO2010080537, WO2010104195, WO2011072132, WO2013139341 and WO2013185766; European Published Patent Application EP2125758A1; US Published Patent Application US2011065739 and U.S. Pat. No. 8,367,708.

SUMMARY OF THE INVENTION

In one aspect, the present invention relates to a compound of formula (I) (as described herein) or a tautomer, a stereoisomer or a geometrical isomer thereof; or pharmaceutically acceptable salt, a pharmaceutically acceptable solvate, a prodrug, a polymorph, an N-oxide, a S-oxide or a carboxylic acid isostere thereof.

In another aspect of the present invention, there is provided a process for the preparation of the compound of Formula (I) or a pharmaceutically acceptable salt thereof.

In a further aspect, the present invention relates to a pharmaceutical composition comprising a therapeutically effective amount of a compound of Formula (I) or a stereoisomer, a tautomer or a geometrical isomer thereof or a pharmaceutically acceptable salt or a pharmaceutically acceptable solvate thereof; and at least one pharmaceutically acceptable carrier or excipient.

In a further aspect, the present invention relates to a pharmaceutical composition comprising a therapeutically effective amount of a compound of Formula (I) or a pharmaceutically acceptable salt thereof; and one further therapeutically active agent and at least one pharmaceutically acceptable carrier or excipient.

In another further aspect, the present invention relates to a method for modulating GPR120 function in a cell.

In yet another aspect, the present invention provides a compound of Formula (I) or a stereoisomer, a tautomer or a geometrical isomer thereof or a pharmaceutically acceptable salt or a pharmaceutically acceptable solvate thereof; for use in the treatment or prophylaxis of a disease or a disorder mediated by GPR120.

In yet another further aspect, the present invention provides a method for the treatment or prophylaxis of a disease or a disorder mediated by GPR120, comprising administering to a subject in need thereof; a therapeutically effective amount of the compound of Formula (I) or a stereoisomer, a tautomer or a geometrical isomer thereof or a pharmaceutically acceptable salt or a pharmaceutically acceptable solvate thereof.

In a still further aspect, the present invention relates to use of the compound of Formula (I) or a stereoisomer, a tautomer or a geometrical isomer thereof or a pharmaceutically acceptable salt or a pharmaceutically acceptable solvate thereof; in the manufacture of a medicament, for the treatment or prophylaxis of a disease or a disorder mediated by GPR120.

In another further aspect, the present invention relates to use of the compound of Formula (I) or a stereoisomer, a tautomer or a geometrical isomer thereof or a pharmaceutically acceptable salt or a pharmaceutically acceptable solvate thereof; in combination with one further therapeutically active agent for the treatment or prophylaxis of a disease or a condition mediated by GPR120.

These and other objectives and advantages of the present invention will be apparent to those skilled in the art from the following description.

DETAILED DESCRIPTION OF THE INVENTION

In a first aspect, the present invention relates to a compound of formula (I),

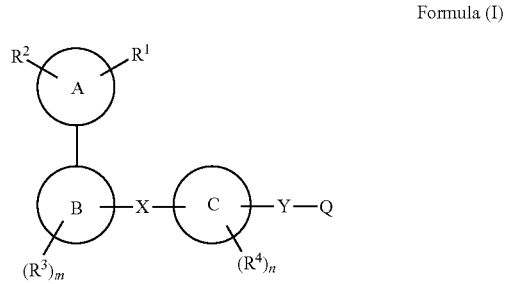

Formula (I)

or a tautomer, a stereoisomer or a geometrical isomer thereof; or pharmaceutically acceptable salt, a pharmaceutically acceptable solvate, a prodrug, a polymorph, an N-oxide, a S-oxide or a carboxylic acid isostere thereof;

wherein:

Ring A is a saturated or unsaturated 4- to 10-membered carbocycle; a 5- to 10-membered heteroaryl; or a saturated or partly saturated or unsaturated 5- to 10-membered heterocycle; wherein said heteroaryl or heterocycle contain 1, 2, 3 or 4 heteroatoms independently selected from N, O and S;

Ring B and Ring C are independently selected from the group consisting of $(C_6-C_{10})$aryl and 6- to 10-membered heteroaryl which contains 1, 2 or 3 heteroatoms independently selected from the group consisting of N, O and S;

X is $-(CR^8R^9)_p-O-$, $-(CR^8R^9)_p-S-$, $-(CR^8R^9)_p-N(R^{10})-$, $-O-(CR^8R^9)_p-$, $-S-(CR^8R^9)_p-$ or $-N(R^{10})-(CR^8R^9)_p$;

Y is $-(CR^{14}R^{15})_g-$;

Q is $CO_2M$, $-CONH_2$, $-CONH[(C_1-C_6)alkyl]$, $-CON[(C_1-C_6)alkyl]_2$ or $-CONHSO_2(C_1-C_6)alkyl$;

M is hydrogen, deuterium or $(C_1-C_6)$alkyl;

$R^1$ is

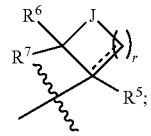

wherein is point of attachment to ring A;

J is $-CH_2-$, $-CHF-$, $-CF_2-$, $-C[(C_1-C_6)alkyl]_2-$, $-O-$, $-NR^a-$ or $-S-$; "—" represents an optional bond;

$R^a$ is hydrogen, $(C_1-C_6)$alkyl or halo$(C_1-C_6)$alkyl;

$R^2$ is selected from the group consisting of hydrogen, halogen, $(C_1-C_6)$alkyl, halo$(C_1-C_6)$alkyl, $(C_1-C_6)$alkoxy, hydroxy, $(C_3-C_{10})$cycloalkyl, $(C_6-C_{10})$aryl, heteroaryl, heterocyclyl, $(C_6-C_{10})$aryl-$(C_1-C_6)$alkyl, $(C_1-C_6)$alkyl-$(C_6-C_{10})$aryl, $(C_6-C_{10})$aryloxy, heterocyclyl-$(C_1-C_6)$alkyl, $(C_1-C_6)$alkyl-heterocyclyl, heteroaryl-$(C_1-C_6)$alkyl, $(C_1-C_6)$alkyl-heteroaryl, cyano, —$NR^{10}R^{11}$, —$C(O)NR^{10}R^{11}$, —$C(S)NR^{10}R^{11}$, —$S(O)_tR^{12}$ and —$C(O)R^{13}$; or $R^1$ and $R^2$ are combined together with one or two atoms of Ring A to form:
i) a 3- to 8-membered partly unsaturated or saturated carbocycle; or
ii) a 3- to 8-membered saturated heterocycle which contains 1, 2 or 3 heteroatoms independently selected from the group consisting of N, O and S;
wherein the said carbocycle or heterocycle can be unsubstituted or substituted with one or more groups independently selected from the group consisting of $(C_1-C_6)$alkenyl, $(C_1-C_6)$alkyl, halo$(C_1-C_6)$alkyl, $(C_1-C_6)$alkoxy, hydroxy, halogen, cyano, oxo, $(C_3-C_{10})$cycloalkyl, $(C_6-C_{10})$aryl, heteroaryl and heterocyclyl;

$R^3$ at each occurrence, is independently selected from the group consisting of hydrogen, halogen, $(C_1-C_6)$alkyl, halo$(C_1-C_6)$alkyl, $(C_1-C_6)$alkoxy, hydroxy, $(C_3-C_{10})$cycloalkyl, $(C_6-C_{10})$aryl, heteroaryl, heterocyclyl, $(C_6-C_{10})$aryl-$(C_1-C_6)$alkyl, $(C_1-C_6)$alkyl-$(C_6-C_{10})$aryl, $(C_6-C_{10})$aryloxy, heterocyclyl-$(C_1-C_6)$alkyl, $(C_1-C_6)$alkyl-heterocyclyl-, heteroaryl-$(C_1-C_6)$alkyl, $(C_1-C_6)$alkyl-heteroaryl, cyano, —$NR^{10}R^{11}$, —$C(O)NR^{10}R^{11}$, —$C(S)NR^{10}R^{11}$, —$S(O)_tR^{12}$ and —$C(O)R^{13}$;

$R^4$, at each occurrence, is independently selected from the group consisting of hydrogen, $(C_1-C_6)$alkyl, halo$(C_1-C_6)$alkyl, $(C_1-C_6)$alkoxy, hydroxy, halogen, cyano, $(C_3-C_{10})$cycloalkyl, $(C_6-C_{10})$aryl, heteroaryl, heterocyclyl, $(C_6-C_{10})$aryl-$(C_1-C_6)$alkyl, $(C_1-C_6)$alkyl-$(C_6-C_{10})$aryl, $(C_6-C_{10})$aryloxy, heterocyclyl-$(C_1-C_6)$alkyl, $(C_1-C_6)$alkyl-heterocyclyl, heteroaryl-$(C_1-C_6)$alkyl, $(C_1-C_6)$alkyl-heteroaryl, —$NR^{10}R^{11}$, —$S(O)_tR^{12}$ and —$C(O)R^{13}$;

$R^5$ is selected from the group consisting of hydrogen, $(C_1-C_6)$alkyl, hydroxy, cyano, —$COR^{10}$, —$NR^{10}R^{11}$, —$CONR^{10}R^{11}$, $(C_1-C_6)$alkylamino, di$(C_1-C_6)$alkyl amino, $(C_1-C_6)$alkoxy, halo$(C_1-C_6)$alkyl, —$S(O)_tR^{12}$ and —$C(O)R^{13}$;

$R^6$ and $R^7$ are independently selected from the group consisting of hydrogen, $(C_1-C_6)$alkyl, halo$(C_1-C_6)$alkyl and halogen;

$R^8$ and $R^9$ are independently selected from the group consisting of hydrogen, deuterium, $(C_1-C_6)$alkyl, halo$(C_1-C_6)$alkyl and halogen; or $R^8$ and $R^9$ can combine together to form
i) a 3- to 5-membered saturated carbocycle selected from the group consisting of cyclopropane, cyclobutane, cyclopentane and cyclohexane; or
ii) a 4- to 6-membered saturated heterocycle selected from the group consisting of oxetane, thietane, azetidine, tetrahydrofuran, tetrahydrothiophene, pyrrolidine and piperidine;

$R^{10}$ is hydrogen, hydroxy, $(C_1-C_6)$alkyl, halo$(C_1-C_6)$alkyl, $(C_1-C_6)$alkoxy, $(C_3-C_{10})$cycloalkyl, $(C_6-C_{10})$aryl, heterocyclyl, heteroaryl, $(C_6-C_{10})$aryloxy, $(C_6-C_{10})$aryl-$(C_1-C_6)$alkyl, $(C_1-C_6)$alkyl-$(C_6-C_{10})$aryl, heterocyclyl-$(C_1-C_6)$alkyl, $(C_1-C_6)$alkyl-heterocyclyl, heteroaryl-$(C_1-C_6)$alkyl or $(C_1-C_6)$alkyl-heteroaryl or —$S(O)_tR^{12}$;

$R^{11}$ is hydrogen, hydroxy, $(C_1-C_6)$alkyl, halo$(C_1-C_6)$alkyl, $(C_3-C_{10})$cycloalkyl, $(C_1-C_6)$alkoxy, $(C_3-C_{10})$cycloalkyl, $(C_6-C_{10})$aryl, heterocyclyl, heteroaryl, $(C_6-C_{10})$aryloxy, $(C_6-C_{10})$aryl-$(C_1-C_6)$alkyl, $(C_1-C_6)$alkyl-$(C_6-C_{10})$aryl, heterocyclyl-$(C_1-C_6)$alkyl, $(C_1-C_6)$alkyl-heterocyclyl, heteroaryl-$(C_1-C_6)$alkyl, $(C_1-C_6)$alkyl-heteroaryl or —$S(O)_tR^{12}$; or $R^{10}$ and $R^{11}$ are combined together to form a 3- to 8-membered saturated or unsaturated ring which contains 1, 2 or 3 heteroatoms independently selected from the group consisting of N, O and S;

$R^{12}$ and $R^{13}$ are independently selected from the group consisting of hydrogen, $(C_1-C_6)$alkyl, halo$(C_1-C_6)$alkyl, $(C_3-C_{10})$cycloalkyl, $(C_6-C_{10})$aryl, heterocyclyl, heteroaryl, $(C_6-C_{10})$aryl-$(C_1-C_6)$alkyl, $(C_1-C_6)$alkyl-$(C_6-C_{10})$aryl, heterocyclyl-$(C_1-C_6)$alkyl, $(C_1-C_6)$alkyl-heterocyclyl, heteroaryl-$(C_1-C_6)$alkyl and $(C_1-C_6)$alkyl-heteroaryl;

$R^{14}$ and $R^{15}$ are independently selected from the group consisting of hydrogen, $(C_1-C_6)$alkyl, halo$(C_1-C_6)$alkyl and halogen;
or
$R^{14}$ and $R^{15}$ are combined together to form a 3- to 5-membered saturated carbocycle or 4- to 6-membered saturated heterocycle which optionally contains 1 or 2 heteroatoms independently selected from the group consisting of N, O and S; wherein the said carbocycle or heterocycle can be substituted or unsubstituted.

g is 2, 3, 4, 5 or 6;
m is 0, 1 or 2;
n is 0, 1 or 2;
p is 1, 2 or 3;
r is 0, 1, 2, 3 or 4;
t is 0, 1 or 2;
wherein
$(C_1-C_6)$alkyl is unsubstituted or substituted with one or more groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, $(C_6-C_{10})$ aryloxy, heterocyclyl, heteroaryl, amino, cyano, nitro, —$NH(C_1-C_6)$alkyl, —$N[(C_1-C_6)$alkyl$]_2$, —$C(O)(C_1-C_6)$alkyl, —$C(O)O(C_1-C_6)$alkyl, —$C(O)NH_2$, —$C(O)NH(C_1-C_6)$alkyl, —$C(O)N[(C_1-C_6)$alkyl$]_2$ and —$C(O)NHSO_2(C_1-C_6)$alkyl;

$(C_3-C_{10})$cycloalkyl is unsubstituted or substituted with one or more groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, amino, cyano and nitro;

carbocycle is unsubstituted or substituted with one or more groups independently selected from the group consisting of $(C_1-C_6)$alkyl, halo$(C_1-C_6)$alkyl, hydroxy, halogen, $(C_1-C_6)$alkoxy, halo$(C_1-C_6)$alkoxy, $(C_6-C_{10})$aryl, $(C_3-C_{10})$cycloalkyl, heteroaryl, heterocyclyl, amino, cyano, nitro, —$C(O)O(C_1-C_6)$alkyl, —$C(O)NR^{10}R^{11}$ and —$S(O)_tR^{12}$; wherein $R^{10}$, $R^{11}$, $R^{12}$ and t are as defined above;

$(C_6-C_{10})$aryl is unsubstituted or substituted with one or more groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —$C(O)O(C_1-C_6)$alkyl, —$C(O)NR^{10}R^{11}$ and —$S(O)_tR^{12}$; wherein $R^{10}$, $R^{11}$, $R^{12}$ and t are as defined above;

heterocyclyl is unsubstituted or substituted with one or more groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —$C(O)NR^{10}R^{11}$ and —$S(O)_tR^{12}$; wherein $R^{10}$, $R^{11}$, $R^{12}$ and t are as defined above;

heteroaryl is unsubstituted or substituted with one or more groups independently selected from the group consisting of $(C_1-C_6)$alkyl, halogen, halo$(C_1-C_6)$alkyl, hydroxy, $(C_1-C_6)$ alkoxy, halo$(C_1-C_6)$alkoxy, heterocyclyl, heteroaryl, amino, cyano, nitro, —C(O)NR$^{10}$R$^{11}$ and —S(O)$_t$R$^{12}$; wherein R$^{10}$, R$^{11}$, R$^{12}$ and t are as defined above.

Definitions

Unless otherwise indicated, the following definitions are set forth to illustrate and define the meaning and scope of the various terms used to describe the invention herein and the appended claims. These definitions should not be interpreted in the literal sense as they are not intended to be general definitions and are relevant only for this application.

The singular forms "a", "an" and "the" include plural aspects unless the context clearly dictates otherwise. For instance, the terms "a", "an" and "the" refers to "one or more" when used in the subject specification, including the claims. Thus, for example, reference to "a compound" may include a plurality of such compounds, or reference to "a disease" or "a disorder" includes a plurality of diseases or disorders.

It should also be noted that the term "or" is generally employed in its sense including "and/or" unless the content clearly dictates otherwise.

The term "independently" when used in the context of selection of substituents for a variable, it means that where more than one substituent is selected from a number of possible substituents, those substituents may be the same or different.

As used herein, the term "$(C_1-C_6)$alkyl" or "alkyl" as used herein; alone or as part of a substituent group, refers to the radical of saturated aliphatic groups, including straight or branched-chain alkyl groups. A straight-chain or branched chain alkyl has six or fewer carbon atoms in its backbone, for instance, $C_1-C_6$ for straight chain and $C_3-C_6$ for branched chain. As used herein, $(C_1-C_6)$-alkyl refers to an alkyl group having 1 to 6 (both inclusive) carbon atoms; preferably refers to an alkyl group having 1 to 4 (both inclusive) carbon atoms i.e. $(C_1-C_4)$-alkyl. Representative examples of alkyl include, but are not limited to, methyl, ethyl, n-propyl, n-butyl, n-pentyl, n-hexyl, isopropyl, sec-butyl, isobutyl, tert-butyl, isopentyl, 2-methylbutyl and 3-methylbutyl. In the "$(C_1-C_6)$alkyl" group, one or more carbon atoms can be optionally replaced with one or more heteroatoms independently selected from N, O and S.

Furthermore, unless stated otherwise, the alkyl group can be unsubstituted or substituted with one or more groups; preferably with 1-4 groups, independently selected from the group consisting of $(C_1-C_6)$alkyl, halogen, halo$(C_1-C_6)$ alkyl, hydroxy, $(C_1-C_6)$alkoxy, halo$(C_1-C_6)$alkoxy, $(C_3-C_{10})$ cycloalkyl, $(C_6-C_{10})$aryl, $(C_6-C_{10})$ aryloxy, heterocyclyl, heteroaryl, amino, cyano, nitro, —NH$(C_1-C_6)$alkyl, —N[$(C_1-C_6)$alkyl]$_2$, —C(O)$(C_1-C_6)$alkyl, —C(O)O$(C_1-C_6)$ alkyl, —C(O)NH$_2$, —C(O)NH$(C_1-C_6)$alkyl, —C(O)N[$(C_1-C_6)$alkyl]$_2$ and —C(O)NHSO$_2$$(C_1-C_6)$alkyl.

As used herein, the term "halo$(C_1-C_6)$alkyl" or "haloalkyl" refers to the alkyl group which is substituted with one or more halogens. A monohalo$(C_1-C_6)$alkyl radical, for example, can have a chlorine, bromine, iodine or fluorine atom. Dihalo and polyhalo$(C_1-C_6)$alkyl radicals can have two or more of the same or different halogen atoms. Representative examples of halo$(C_1-C_6)$alkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like groups.

As used herein, the term "$(C_1-C_6)$-alkoxy" or "alkoxy" refers to a $(C_1-C_6)$-alkyl having an oxygen radical attached thereto. The term "$(C_1-C_6)$-alkoxy" or "O—$(C_1-C_6)$-alkyl" or alkoxy wherever used in this specification have the same meaning. Representative examples of alkoxy groups include, but are not limited to, methoxy, ethoxy, propoxy, isopropoxy, n-butoxy, isobutoxy and t-butoxy. Furthermore, unless stated otherwise, the alkoxy groups can be unsubstituted or substituted with one or more groups. A substituted alkoxy refers to a $(C_1-C_6)$-alkoxy substituted with 1-5 groups, preferably with 1-3 groups selected from the groups indicated above as the substituents for the alkyl group.

As used herein, the term "halogen" refers to chlorine, fluorine, bromine or iodine and is preferably, chlorine, bromine or fluorine.

The term "carbocycle" or "carbocyclic ring" refers to a saturated, partially unsaturated, unsaturated or aromatic 3 to 12 membered monocyclic or bicyclic ring systems whose ring atoms are all carbon, and that the said carbocycle has a single point of attachment to the rest of the molecule. If the carbocycle is a bicyclic ring system, then any one ring in the said bicyclic ring system is a 3-7 membered ring. Representative examples of carbocycle include, but are not limited to, cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. "Aromatic carbocycle" or "aromatic carbocyclic ring" refers to 3 to 12 membered monocyclic or bicyclic aromatic ring systems whose all ring atoms are carbon.

The term "$(C_6-C_{14})$-aryl" or "aryl" as used herein refers to monocyclic or bicyclic hydrocarbon groups having 6 to 14 ring carbon atoms, preferably 6 to 10 carbon atoms i.e. "$(C_6-C_{10})$-aryl" in which the carbocyclic ring(s) present have a conjugated pi electron system, which may be optionally substituted by one or more groups. Representative examples of $(C_6-C_{14})$-aryl include, but are not limited to, phenyl, naphthyl, fluorenyl and anthracenyl.

Furthermore, unless stated otherwise, the aryl group can be unsubstituted or substituted with one or more groups. A substituted aryl refers to a $(C_6-C_{14})$-aryl substituted with one or more groups, preferably 1 to 7 groups and more preferably 1 to 3 groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, nitro, —C(O)O$(C_1-C_6)$alkyl, —C(O)NR$^{10}$R$^{11}$ and —S(O)$_t$R$^{12}$; wherein R$^{10}$, R$^{11}$, R$^{12}$ and t are as defined above.

As used herein, the terms "heterocycle", "heterocyclyl" or "heterocyclic" whether used alone or as part of a substituent group, refers to a 3- to 12-membered, preferably 5- to 10-membered saturated or partially unsaturated monocyclic, bicyclic or tricyclic ring system containing 1 to 4 heteroatoms independently selected from oxygen, nitrogen and sulfur. Saturated heterocyclic ring systems do not contain any double bond, whereas partially unsaturated heterocyclic ring systems, can contain at least one double bond, but do not form an aromatic system containing a heteroatom. The oxidized form of the ring nitrogen and sulfur atom contained in the heterocyclyl to provide the corresponding N-oxide, S-oxide or S,S-dioxide is also encompassed in the scope of the present invention. Representative examples of heterocyclyls include, but are not limited to, azetidinyl, acridinyl, benzodioxolyl, benzodioxanyl, dioxolanyl, indolizinyl, perhydroazepinyl, phenothiazinyl, phenoxazinyl, tetrahydroisoquinolinyl, piperidinyl, piperazinyl, homopiperazinyl, 2-oxoazepinyl, azepinyl, 4-piperidonyl, pyrrolidinyl, oxazolinyl, oxazolidinyl, isoxazolidinyl, thiazolinyl, thiazolidinyl, isothiazolyl, quinuclidinyl, isothiazolidinyl, indolinyl, isoindolinyl, octahydroindolyl, octahydroisoindolyl, decahydroisoquinolyl, benzopyranyl, morpholinyl, thiomorpholinyl, thiomorpholinyl sulfoxide, tetrahydrofuryl, tetrahydropyranyl, chromanyl and isochromanyl. When the heterocyclyl group represents "5- to 10-membered heterocyclyl", the representative examples include, but are not limited to, benzodioxolyl, benzo[d][1,3]dioxolyl, benzodioxanyl, tetrahydroisoquinolinyl, piperidinyl, piperazinyl, homopiperazinyl, 2-oxoazepinyl, 4-piperidonyl, pyrrolidinyl, oxazolinyl, oxazolidinyl, and morpholinyl.

Furthermore, unless stated otherwise, the heterocyclyl groups can be unsubstituted or substituted with one or more groups, preferably with 1-7 groups, more preferably with 1-3 groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, amino, cyano, nitro, —C(O)NR$^{10}$R$^{11}$ and —S(O)$_t$R$^{12}$; wherein R$^{10}$, R$^{11}$, R$^{12}$ and t are as defined above.

As used herein, the term "heteroaryl" whether used alone or as part of a substituent group, refers to 5- to 10-membered heterocyclyl having an aromatic ring containing one to four identical or different heteroatoms independently selected from oxygen, nitrogen and sulfur atom. Representative examples of heteroaryls include, but are not limited to, pyrrole, pyrazole, imidazole, tetrazole, pyrazine, furan, thiophene, oxazole, oxadiazole, thiazole, benzimidazole, benzoxazole, triazole, benzothiazole, benzofuran, indole, isoindole, cinnoline, indazole, isoindole, thiadiazole, isoquinoline, benzoxazole, thiophene, benzothiazole, isoxazole, triazine, purine, pyridine, quinoline, isoquinoline, phenazine, oxadiazole, pteridine, carbazole, pyridazine, quinazolinyl, pyrimidine, isothiazole, quinoxaline (benzopyrazine), tetrazole, pyrido[2,3-b]pyrazine. The oxidized form of the ring nitrogen and sulfur atom contained in the heteroaryl to provide the corresponding N-oxide, S-oxide or S,S-dioxide is also encompassed in the scope of the present invention.

Furthermore, unless stated otherwise, the heteroaryl groups can be unsubstituted or substituted with one or more groups; preferably with 1-7 groups, more preferably with 1-3 groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, heterocyclyl, heteroaryl, amino, cyano, representative examples of heteroaryl include, but are not limited to, pyrrole, pyrazole, imidazole, pyrazine, furan, thiophene, triazole, benzothiazole, benzofuran, indole, purine, pyridine, quinoline, isoquinoline, pyridazine, quinazolinyl, pyrimidine and isothiazole.

As used herein, the term "$(C_3-C_{12})$-cycloalkyl" or "cycloalkyl", whether used alone or as part of a substituent group, refers to a saturated cyclic hydrocarbon radical including 1, 2 or 3 rings and including a total of 3 to 12 carbon atoms forming the rings, which may be optionally substituted by one or more substituents. The term cycloalkyl includes bridged, fused and spiro ring systems. As used herein, $(C_3-C_{12})$-cycloalkyl refers to a cycloalkyl group having 3 to 12 (both inclusive) carbon atoms; preferably, refers to cycloalkyl group having 3 to 10 (both inclusive) carbon atoms i.e. $(C_3-C_{10})$-cycloalkyl; and more preferably, refers to cycloalkyl group having 3 to 7 (both inclusive) carbon atoms i.e. $(C_3-C_7)$-cycloalkyl. Representative examples of cycloalkyl include, but are not limited to, cyclopropyl, cyclobutyl, cyclopentyl, cyclohexyl, perhydronaphthyl, adamantyl, homoadamantyl, noradamantyl, norbornyl, bicyclo[2.1.0]pentanyl, bicyclo[2.2.1]heptyl, spiro[3.3]heptanyl and spiro[4.4]non-2-yl.

The term "tautomer" refers to the coexistence of two or more compounds that differ from each other only in the position of one (or more) mobile atoms and in electron distribution. In fact, tautomers are structural isomers of different energies which are interconvertible via a low energy barrier. For example, proton tautomers (also known as prototropic tautomers) include interconversions via migration of a proton, such as keto-enol and imine-enamine isomerizations.

The term "prodrugs" as used herein refers to any pharmacologically inactive or less active compound which, when metabolized or chemically transformed in vivo by a chemical or physiological process, e.g., a prodrug on being brought to the physiological pH or through enzyme action is converted to the parent compound e.g. the compound of formula (I) of the present invention. For example, in the context of the present invention prodrugs can be esters of the compound of formula (I) which on metabolism the ester group is cleaved to form the active compound of formula (I). Examples of esters include lower alkyl esters, such as the methyl or ethyl ester; carboxy-lower alkyl esters, such as the carboxymethyl ester; nitrooxy- or nitrosooxy-lower alkyl esters, such as the 4-nitrooxybutyl or 4-nitrosooxybutyl ester; and the like.

The phrase, "carboxylic acid isostere" refers to a functional group or a moiety that elicits similar physical, biological and/or chemical properties as a carboxylic acid moiety. Representative examples of carboxylic acid isostere include, but are not limited to:

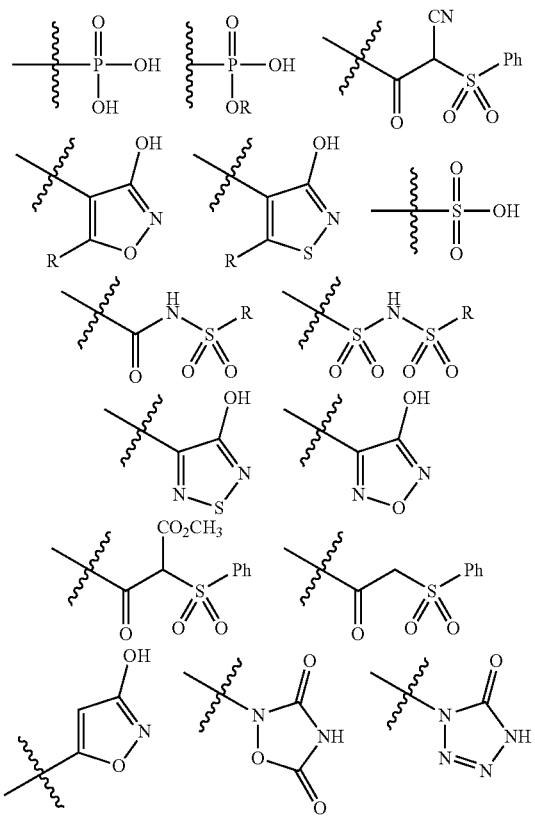

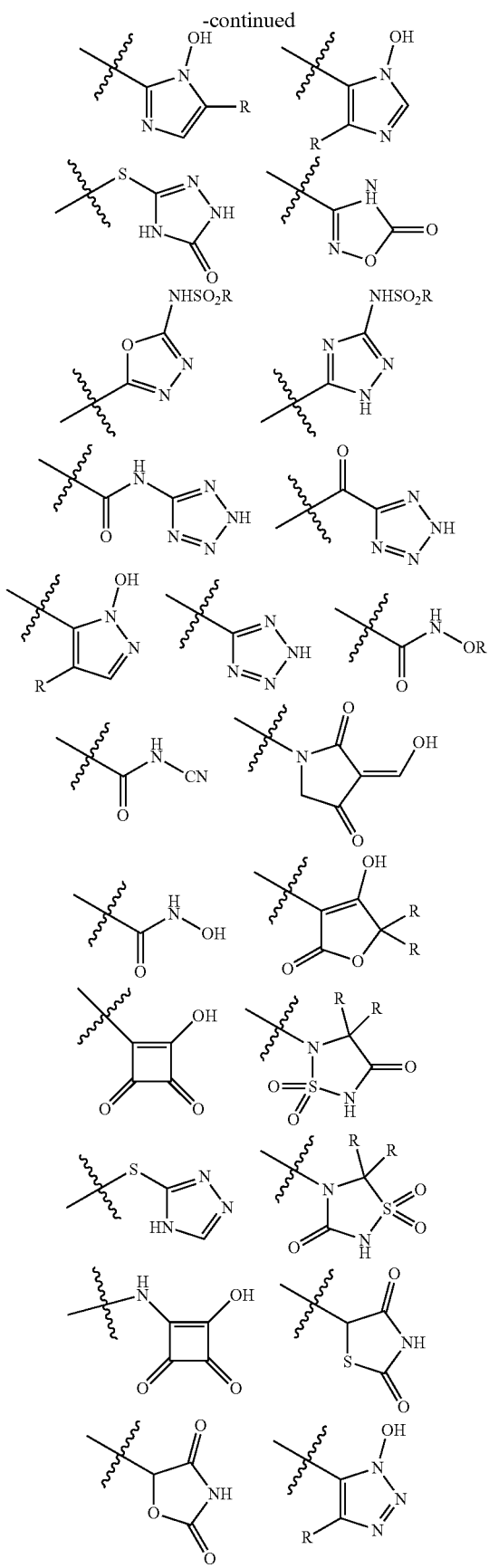

wherein R is hydrogen or $(C_1\text{-}C_3)$alkyl.

As used herein, the term "pharmaceutically acceptable" means that the carrier, diluent, excipient, and/or salt must be compatible with the other ingredients of the formulation, and not deleterious to the recipient thereof.

The term "pharmaceutically acceptable salt(s)" as used herein includes a salt or salts of the active compound i.e. the compound of formula I, which retain the desired biological activity of the subject compound and exhibit minimal undesired toxicological effects; and are prepared with suitable acids or bases, depending on the particular substituents found on the compounds described herein.

Within the context of the present invention and as used herein "N-oxide" refers to the oxide of the nitrogen atom of a nitrogen-containing heteroaryl or heterocycle. N-oxide can be formed in the presence of an oxidizing agent for example peroxide such as m-chloro-perbenzoic acid or hydrogen peroxide. N-oxide refers to an amine oxide, also known as amine-N-oxide, and is a chemical compound that contains N→O bond.

Within the context of the present invention and as used herein "S-oxide" refers to the oxide of the sulfur atom (S-oxide) or dioxide of the sulfur atom (S,S-dioxide) of a sulfur-containing heteroaryl or heterocycle. S-oxide and S,S-dioxides can be formed in the presence of an oxidizing agent for example peroxide such as m-chloro-perbenzoic acid or oxone.

Within the context of the present invention and as used herein, the term "solvate" or "solvates" describe a complex wherein the compound of Formula (I) of the present invention, is coordinated with a proportional amount of a solvent molecule. Specific solvates, wherein the solvent is water, are referred to as hydrates.

Within the context of the present invention and as used herein the term "polymorph" or "polymorphic form" or "polymorphs" refer to crystals of the same compound that differs only in the arrangement and/or conformation of the molecule in the crystal lattice.

The term "subject" as used herein refers to an animal, preferably a mammal, and most preferably a human. The term "mammal" used herein refers to warm-blooded vertebrate animals of the class 'mammalia', including humans, characterized by a covering of hair on the skin and, in the female, milk-producing mammary glands for nourishing the young. The term mammal includes animals such as cat, dog, rabbit, bear, fox, wolf, monkey, deer, mouse, pig and human.

As used herein, the terms "treatment" "treat" and "therapy" and the like refer to alleviate, slow the progression, attenuation, or as such treat the existing diseases or condition (e.g. diabetes). Treatment also includes treating, or alleviating to some extent, one or more of the symptoms of the diseases or condition.

The term "prophylaxis", "prevention" or "preventing" can be used interchangeably and mean preventing the disease or disorder by causing the clinical symptoms of the conditions, diseases, disorders or syndromes to not develop or decreasing the development of the disease or disorder or preventing the further development of the disease or disorder in the subjects (the patients).

The term "compound(s) for use" as used herein embrace any one or more of the following: (1) use of compound(s), (2) method of use of compound(s), (3) use in the treatment of, (4) the use for the manufacture of pharmaceutical composition/medicament for treatment/treating or (5) method of treatment/treating/preventing/reducing/inhibiting comprising administering an effective amount of the active compound to a subject in need thereof.

The term, "therapeutically effective amount" as used herein means an amount of a compound of formula (I) or a pharmaceutically acceptable salt thereof or a composition comprising a compound of formula (I) or a salt thereof, effective in producing the desired therapeutic response in a particular patient (subject) suffering from a disease or disorder mediated by GPR120. An example of a disease or disorder mediated by GPR120 is diabetes such as type 2 diabetes. Particularly, the term "therapeutically effective amount" includes the amount of a compound (in the context of the present invention, the compound of formula (I) or a pharmaceutically acceptable salt thereof), when administered that induces a positive modification in the disease or disorder to be treated or is sufficient to prevent development of, or alleviate to some extent one or more of the symptoms of the disease or disorder being treated in a subject. In respect of the therapeutic amount of the compound, consideration is also given that the amount of the compound used for the treatment of a subject is low enough to avoid undue or severe side effects, within the scope of sound medical judgment. The therapeutically effective amount of the compound or composition will vary with the particular condition (in the context of the present invention, the disease or disorder that is mediated by GPR120) being treated, the age and physical condition of the subject, the severity of the condition being treated or prevented, the duration of the treatment, the nature of concurrent therapy, the specific compound or composition employed, the particular pharmaceutically acceptable carrier utilized and other related factors.

Within the context of the present invention and as used herein interchangeably throughout this application, the terms "compounds of Formula (I)", and "compounds of the present invention" include all the stereoisomeric and tautomeric forms and mixtures thereof in all ratios, and their pharmaceutically acceptable salts, solvates, polymorphs, prodrugs, carboxylic acid isosteres, N-oxides and S-oxides. Further, in the context of the present invention, reference to the compounds of Formula (I) includes reference to the compounds presented herein in one or more embodiments either as such or represented by one or more structural formula.

Within the context of the present invention and as used herein, the term "GPR120 agonist" or "GPR120 agonists" refer to the compound(s) of Formula (I) of the present invention or a tautomer, a stereoisomer or a geometrical isomer thereof; or pharmaceutically acceptable salt, a pharmaceutically acceptable solvate, a prodrug, a polymorph, an N-oxide, a S-oxide or a carboxylic acid isostere thereof; which binds to, activates, increases, stimulates, potentiates, sensitizes or upregulates GPR120 receptor and promotes glucose induced insulin secretion.

The term "optionally substituted" means "substituted or unsubstituted," and therefore, the generic structural formulae described herein encompasses compounds containing the specified optional substituent as well as compounds that do not contain the optional substituent.

Embodiments

According to one embodiment, the present invention encompasses a compound of Formula (I); wherein $R^1$ is

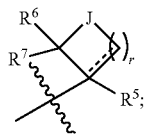

wherein
l is point of attachment to ring A;
J is $—CH_2—$, $—CHF—$, $—CF_2—$, $—CH[(C_1-C_6)alkyl]-$, $—C[(C_1-C_6)alkyl]_2-$, $—O—$, $—NR^a—$ or $—S—$;

"-----" represents an optional bond;
$R^a$ is hydrogen, $(C_1-C_6)$alkyl or halo$(C_1-C_6)$alkyl;
$R^2$ is independently selected from the group consisting of hydrogen, halogen, $(C_1-C_6)$alkyl, halo$(C_1-C_6)$alkyl, $(C_3-C_{10})$cycloalkyl, $(C_6-C_{10})$aryl, heteroaryl, heterocyclyl, $(C_6-C_{10})$aryl-$(C_1-C_6)$alkyl, $(C_1-C_6)$alkyl-$(C_6-C_{10})$aryl-, heterocyclyl-$(C_1-C_6)$alkyl-, $(C_1-C_6)$alkyl-heterocyclyl, heteroaryl-$(C_1-C_6)$alkyl-, $(C_1-C_6)$alkyl-heteroaryl-, cyano, $—C(O)NR^{10}R^{11}$, $—C(S)NR^{10}R^{11}$, $—S(O)_rR^{12}$ and $—C(O)R^{13}$;
$R^5$, $R^6$, $R^7$ and r are as defined above.

According to one embodiment, the present invention encompasses a compound of Formula (I); wherein:
$R^1$ and $R^2$ are combined together with one or two atoms of Ring A to form:
i) a 3- to 8-membered, partly saturated or saturated carbocycle; or
ii) a 3- to 8-membered, saturated heterocycle which contains 1, 2 or 3 heteroatoms independently selected from the group consisting of N, O and S;
wherein the said carbocycle or heterocycle can be unsubstituted or substituted with the one or more groups independently selected from $(C_1-C_6)$alkyl, halo$(C_1-C_6)$alkyl, $(C_1-C_6)$alkoxy, hydroxy, halogen, cyano, $(C_6-C_{10})$aryl, heteroaryl and heterocyclyl.

According to one embodiment, the present invention encompasses a compound of Formula (I), wherein Ring A is 6- to 10-membered aromatic carbocycle; a 5- or 6-membered heteroaryl; or a 5- or 6-membered heterocyclyl wherein the heteroaryl and heterocyclyl contain 1, 2 or 3 heteroatoms independently selected from the group consisting of N, O and S; wherein each of 6- to 10-membered aromatic carbocycle, heteroaryl or heterocyclyl is unsubstituted or substituted with one or more groups as described herein.

According to one embodiment, the present invention encompasses a compound of Formula (I), wherein Ring A is 6- to 10-membered aromatic carbocycle.

According to one embodiment, the present invention encompasses a compound of Formula (I), wherein Ring A is phenyl; wherein phenyl is unsubstituted or substituted with one or more groups as described herein.

According to one embodiment, the present invention encompasses a compound of Formula (I), wherein Ring A is a 5- or 6-membered heteroaryl containing 1, 2 or 3 heteroatoms independently selected from the group consisting of N, O and S; wherein the heteroaryl group is unsubstituted or substituted with one or more groups as described herein.

According to one embodiment, the present invention encompasses a compound of Formula (I), wherein Ring A is 5- or 6-membered heteroaryl selected from the group consisting of pyrrole, pyrazole, imidazole, pyrazine, furan, thiophene, oxazole, oxadiazole, thiazole, thiadiazole, pyridine, pyrimidine, and tetrazole; wherein each of the heteroaryl is unsubstituted or substituted with one or more groups as described herein.

According to one embodiment, the present invention encompasses a compound of Formula (I), wherein Ring A is pyridine, thiophene, thiazole, thiadiazole or pyrimidine; wherein each of pyridine, thiophene, thiadiazole, thiazole and pyrimidine is unsubstituted or substituted with one or more groups as described herein.

According to one embodiment, the present invention encompasses a compound of Formula (I), wherein Ring A is pyridine, thiophene or thiazole; wherein each of pyridine, thiophene and thiazole is unsubstituted or substituted with one or more groups as described herein.

According to one embodiment, the present invention encompasses a compound of Formula (I); wherein Ring B is $(C_6-C_{10})$aryl; wherein $(C_6-C_{10})$aryl is unsubstituted or substituted with one or more groups as described herein.

According to one embodiment, the present invention encompasses a compound of Formula (I), wherein Ring B is phenyl; wherein said phenyl is unsubstituted or substituted with one or more $R^3$ groups as described herein.

According to one embodiment, the present invention encompasses a compound of Formula (I), wherein Ring B is unsubstituted phenyl.

According to one embodiment, the present invention encompasses a compound of Formula (I), wherein Ring B is phenyl which is substituted with one to three $R^3$ groups; wherein $R^3$ group at each occurrence is independently selected from the group consisting of hydrogen, halogen, $(C_1-C_6)$alkyl, halo$(C_1-C_6)$alkyl, $(C_3-C_{10})$cycloalkyl, $(C_6-C_{10})$aryl, heteroaryl and heterocyclyl.

According to one embodiment, the present invention encompasses a compound of Formula (I), wherein Ring B is phenyl which is substituted with one $R^3$ selected from the group consisting of hydrogen, halogen, $(C_1-C_6)$alkyl, $(C_3-C_{10})$cycloalkyl and heterocyclyl.

According to one embodiment, the present invention encompasses a compound of Formula (I), wherein Ring B is phenyl which is unsubstituted or substituted with halogen.

According to one embodiment, the present invention encompasses a compound of Formula (I), wherein Ring B is phenyl which is unsubstituted or substituted with fluoro.

According to one embodiment, the present invention encompasses a compound of Formula (I); wherein Ring B is 6- to 10-membered heteroaryl which contains 1, 2 or 3 heteroatoms independently selected from N, O and S.

According to one embodiment, the present invention encompasses a compound of Formula (I), wherein Ring B is a 6-membered heteroaryl which contains 1, 2 or 3 N; wherein said heteroaryl is unsubstituted or substituted with one or more groups as described herein.

According to one embodiment, the present invention encompasses a compound of Formula (I), wherein Ring B is selected from the group consisting of pyridine, pyridazine, pyrimidine, pyrazine, 1,2,3-triazine, 1,2,4-triazine and 1,3,5-triazine; which are unsubstituted or substituted with one or more groups as described herein.

According to one embodiment, the present invention encompasses a compound of Formula (I), wherein Ring B is pyridine; which is unsubstituted or substituted with one or more groups as described herein.

According to one embodiment, the present invention encompasses a compound of Formula (I), wherein Ring B is pyridine which is unsubstituted or substituted with one $R^3$ selected from the group consisting of hydrogen, halogen, $(C_1-C_6)$alkyl, $(C_3-C_{10})$cycloalkyl and heterocyclyl.

According to one embodiment, the present invention encompasses a compound of Formula (I), wherein Ring B is pyridine which is unsubstituted or substituted with heterocyclyl.

According to one embodiment, the present invention encompasses a compound of Formula (I); wherein Ring B is $(C_6-C_{10})$aryl; or 6- to 10-membered heteroaryl which contains 1, 2 or 3 heteroatoms independently selected from N, O and S; and X is —$(CR^8R^9)_p$—O—, —$(CR^8R^9)_p$—S— or —$(CR^8R^9)_p$—N($R^{10}$)—; wherein $R^8$, $R^9$ and p are as defined above.

According to one embodiment, the present invention encompasses a compound of Formula (I); wherein: Ring C is 6- to 10-membered heteroaryl which contains 1, 2 or 3 heteroatoms independently selected from N, O and S.

According to one embodiment, the present invention encompasses a compound of Formula (I), wherein Ring C is a 6-membered heteroaryl which contains 1, 2 or 3 N; wherein said heteroaryl is unsubstituted or substituted with one or more groups as described herein.

According to one embodiment, the present invention encompasses a compound of Formula (I), wherein Ring C is selected from the group consisting of pyridine, pyridazine, pyrimidine, pyrazine, 1,2,3-triazine, 1,2,4-triazine and 1,3,5-triazine; which are unsubstituted or substituted with one or more groups as described herein.

According to one embodiment, the present invention encompasses a compound of Formula (I), wherein Ring C is pyridine; which is unsubstituted or substituted with one or more groups as described herein.

According to one embodiment, the present invention encompasses a compound of Formula (I); wherein Ring C is $(C_6-C_{10})$aryl; wherein $(C_6-C_{10})$ aryl is unsubstituted or substituted with one or more $R^4$ groups as described herein.

According to one embodiment, the present invention encompasses a compound of Formula (I), wherein Ring C is phenyl; wherein said phenyl is unsubstituted or substituted with one or more $R^4$ groups as described herein.

According to one embodiment, the present invention encompasses a compound of Formula (I), wherein Ring C is phenyl and $R^4$ is hydrogen.

According to one embodiment, the present invention encompasses a compound of Formula (I), wherein Ring C is phenyl which is substituted with one to three $R^4$ groups; wherein $R^4$ group at each occurrence is independently selected from the group consisting of hydrogen, halogen, $(C_1-C_6)$alkyl, halo$(C_1-C_6)$alkyl, $(C_1-C_6)$alkoxy, hydroxy, halogen, cyano, —$NR^{10}R^{11}$, —$S(O)_tR^{12}$ and —$C(O)R^{13}$; wherein $R^{10}$, $R^{11}$, $R^{12}$, $R^{13}$ and t are as defined above.

According to one embodiment, the present invention encompasses a compound of Formula (I), wherein Ring C is $(C_6-C_{10})$aryl; or 6- to 10-membered heteroaryl which contains 1, 2 or 3 heteroatoms independently selected from the group consisting of N, O and S; Y is —$(CR^{14}R^{15})_g$—; where $R^{14}$, $R^{15}$ and g are as defined; and Q is —$CO_2M$ or —$CONH_2$, where M is hydrogen, deuterium or $(C_1-C_6)$alkyl.

According to one embodiment, the present invention encompasses a compound of Formula (I), wherein Ring C is $(C_6-C_{10})$aryl; which is unsubstituted or substituted with one or more groups as described herein; and Y is —$(CR^{14}R^{15})_g$; wherein $R^{14}$ and $R^{15}$ are independently selected from hydrogen and $(C_1-C_6)$alkyl and g is as defined above; and Q is —$CO_2M$; where M is H or $(C_1-C_6)$alkyl.

According to one embodiment, the present invention encompasses a compound of Formula (I), wherein Ring C is $(C_6-C_{10})$aryl; which is unsubstituted or substituted with one or more groups as described herein; and Y is —$(CR^{14}R^{15})_g$; wherein $R^{14}$ and $R^{15}$ are combined together to form a 3- to 5-membered saturated carbocycle or 4- to 6-membered saturated heterocycle which optionally contains 1 or 2 heteroatoms independently selected from the group consisting of N, O and S; wherein said ring is unsubstituted or substituted with a substituent independently selected from the group consisting of $(C_1-C_6)$alkyl, halo$(C_1-C_6)$alkyl, $(C_1-C_6)$alkoxy, hydroxy, halogen, cyano, $(C_6-C_{10})$aryl, heteroaryl and heterocyclyl; and Q is —$CO_2M$; where M is H or $(C_1-C_6)$alkyl.

According to another embodiment, the present invention encompasses a compound of Formula (I), wherein X is —$(CR^8R^9)_p$—O—, wherein $R^8$, $R^9$ and p are as defined above.

According to another embodiment, the present invention encompasses a compound of Formula (I), wherein Y is —$(CR^{14}R^{15})_g$—; wherein $R^{14}$ and $R^{15}$ are independently hydrogen or $(C_1-C_6)$alkyl.

According to another embodiment, the present invention encompasses a compound of Formula (I), wherein Y is —$(CR^{14}R^{15})_g$—; wherein $R^{14}$ and $R^{15}$ are hydrogen.

According to another embodiment, the present invention encompasses a compound of Formula (I), wherein Y is —$(CR^{14}R^{15})_g$—; wherein $R^{14}$ and $R^{15}$ are hydrogen, and g is 2, 3 or 4.

According to another embodiment, the present invention encompasses a compound of Formula (I), wherein Y is —$(CR^{14}R^{15})_g$—; wherein $R^{14}$ and $R^{15}$ are hydrogen, and g is 3.

According to one embodiment, the present invention encompasses a compound of Formula (I), wherein Q is —$CO_2M$, wherein M is hydrogen, deuterium or $(C_1-C_6)$alkyl.

According to one embodiment, the present invention encompasses a compound of Formula (I), wherein Q is —$CO_2M$, wherein M is hydrogen.

According to an embodiment, the present invention encompasses a compound of Formula (I), wherein Ring B is represented as follows;

which can be selected from phenyl or a 6-membered heteroaryl; wherein each of the phenyl and heteroaryl is unsubstituted or substituted with one or more groups as described herein.

According to one embodiment, the present invention encompasses a compound of Formula (I), wherein Ring B is attached to Ring A in 1,2-disubstituted fashion with respect to variable X and is represented by the following structural formula:

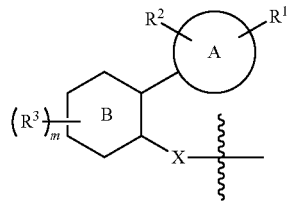

wherein,
⁁ is point of attachment of X with Ring C.
Ring A, ring B, $R_1$, $R_2$, $R_3$, X and m are as defined above.

According to one embodiment, the present invention encompasses a compound of Formula (I), wherein Ring B and Ring A are bonded to form the group selected from

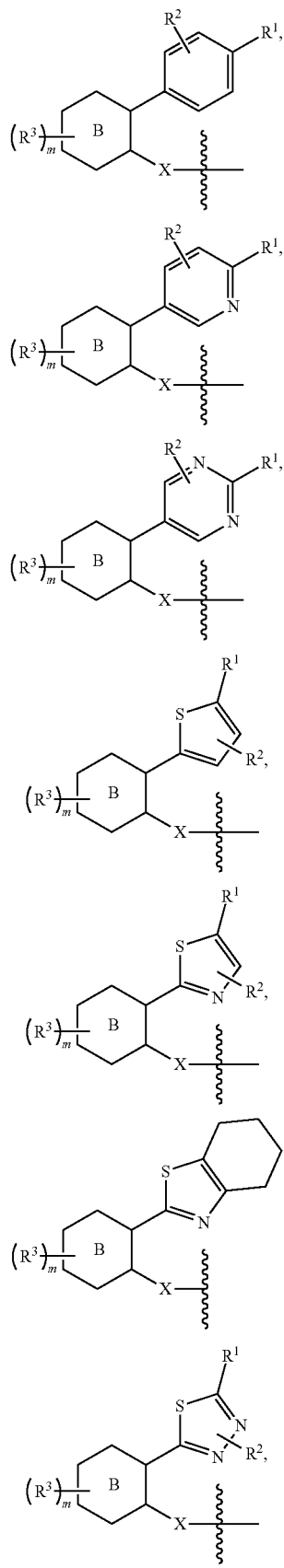

-continued

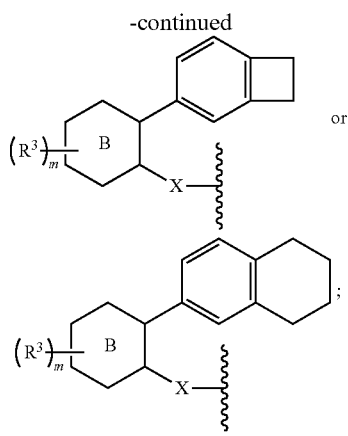

wherein,
⸹ is point of attachment of X with Ring C.
Ring B, $R_1$, $R_2$, $R_3$, X and m are as defined above.
According to one embodiment, the present invention encompasses a compound of Formula (I), wherein $R_1$ is

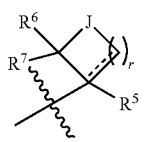

wherein
$R^5$ is hydrogen, $(C_1-C_6)$alkyl, halo$(C_1-C_6)$alkyl, hydroxy, cyano, —$NR^{10}R^{11}$, —$CONR^{10}R^{11}$, $(C_1-C_6)$alkoxy, halo$(C_1-C_6)$alkylene or —$C(O)R^{13}$;
$R^6$ and $R^7$ are independently selected from the group consisting of hydrogen, $(C_1-C_6)$alkyl and halogen;
⸹ is point of attachment of $R^1$ with Ring A;
J is —$CH_2$—, —CHF—, —$CF_2$—, —O—, —$NR^a$— or —S—;
"-----" is an optional bond;
$R^a$ is hydrogen or $(C_1-C_6)$alkyl;
r is 0, 1 or 2.
According to one embodiment, the present invention encompasses a compound of Formula (I), wherein $R^1$ is

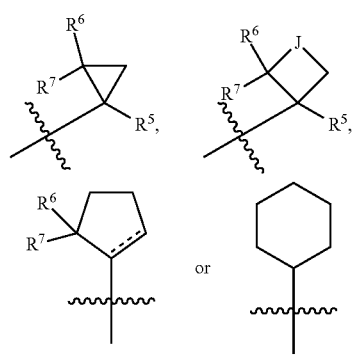

wherein
$R_5$ is hydrogen, $(C_1-C_6)$alkyl, $(C_1-C_6)$alkoxy, hydroxy, cyano, —$NR^{10}R^{11}$, or halo$(C_1-C_6)$alkyl;
J is —$CH_2$ or —O—;
$R^6$ and $R^7$ are independently selected from the group consisting of hydrogen and $(C_1-C_6)$alkyl; r is 1; and $R_2$ is hydrogen, halogen, $(C_1-C_6)$alkyl or cyano.

According to one embodiment, the present invention encompasses a compound of Formula (I), wherein $R^1$ and $R^2$ are combined together with one or two atoms of Ring A to form:
i) 4- to 6-membered saturated carbocycle or
ii) 5- to 6-membered saturated heterocycle which contains 1, 2 or 3 heteroatoms independently selected from the group consisting of N, O and S; wherein said ring is unsubstituted or substituted with one or more groups independently selected from the group consisting of $(C_1-C_6)$alkyl, halo$(C_1-C_6)$alkyl, $(C_1-C_6)$alkoxy, hydroxy, halogen, cyano, $(C_6-C_{10})$aryl, heteroaryl and heterocyclyl.

According to one embodiment, the present invention encompasses a compound of Formula (I), wherein $R^1$ and $R^2$ are combined together with one or two atoms of Ring A to form the following groups;

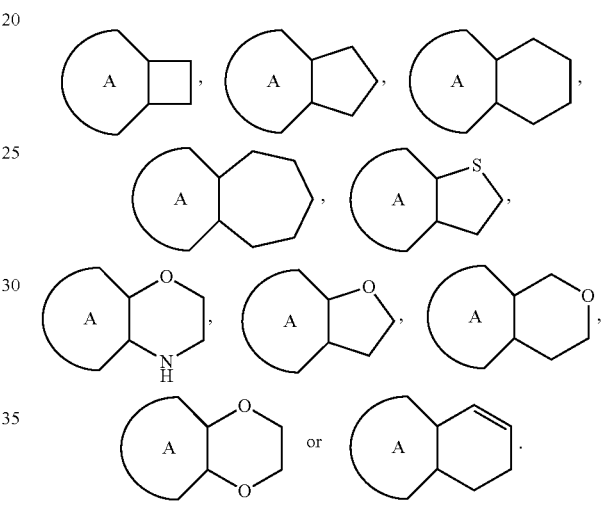

wherein the groups are unsubstituted or substituted with one or more groups independently selected from the group consisting of $(C_1-C_6)$alkenyl, $(C_1-C_6)$alkyl, halo$(C_1-C_6)$alkyl, $(C_1-C_6)$alkoxy, hydroxy, halogen, cyano, oxo, $(C_3-C_{10})$cycloalkyl, $(C_6-C_{10})$aryl, heteroaryl and heterocyclyl.

According to one embodiment, the present invention encompasses a compound of Formula (I), wherein the Ring B is represented as

and the Ring C is represented as

Accordingly, in one embodiment the compound of formula I of the present invention encompasses a compound of formula Ia;

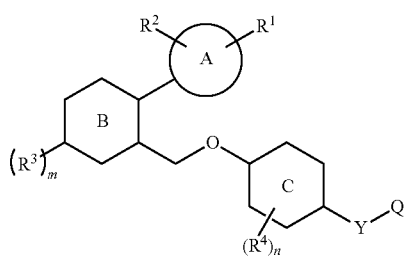

Formula (Ia)

wherein:

Ring A is saturated or unsaturated 4- to 6-membered carbocycle; or 5- to 6-membered heteroaryl; or saturated or partly saturated or unsaturated 5- to 10-membered heterocyclic ring which contains 1, 2, 3 or 4 heteroatoms independently selected from N, O and S;

Ring B is phenyl; or 6-membered heteroaryl which contains 1, 2 or 3 N atoms;

Ring C is phenyl; or 6-membered heteroaryl which contains 1, 2 or 3 N atoms;

Y is —$(CR^{14}R^{15})_g$—;

Q is —$CO_2M$, —$CONH_2$, —$CONH[(C_1-C_6)alkyl]$, —$CON[(C_1-C_6)alkyl]_2$ or —$CONHSO_2(C_1-C_6)alkyl$;

M is hydrogen, deuterium or $(C_1-C_6)alkyl$;

$R^1$ is

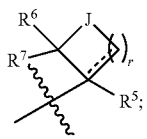

wherein

╎ is point of attachment;

J is —$CH_2$—, —CHF—, —$CF_2$—, —$CH[(C_1-C_6)alkyl]$, —$C[(C_1-C_6)alkyl]_2$, —O—, —$NR^a$— or —S—;

"-----" represents an optional bond;

$R^a$ is hydrogen, $(C_1-C_6)alkyl$ and halo$(C_1-C_6)alkyl$;

$R^2$ is selected from the group consisting of hydrogen, halogen, $(C_1-C_6)alkyl$, halo$(C_1-C_6)alkyl$, $(C_3-C_{10})$cycloalkyl, $(C_6-C_{10})aryl$, heteroaryl, heterocyclyl, $(C_6-C_{10})aryl-(C_1-C_6)alkyl$, $(C_1-C_6)alkyl-(C_6-C_{10})aryl$-, heterocyclyl-$(C_1-C_6)alkyl$-, $(C_1-C_6)alkyl$-heterocyclyl, heteroaryl-$(C_1-C_6)alkyl$-, $(C_1-C_6)alkyl$-heteroaryl-, cyano, —$C(O)NR^{10}R^{11}$, —$C(S)NR^{10}R^{11}$, —$S(O)_tR^{12}$ and —$C(O)R^{13}$; or $R^1$ and $R^2$ are combined together with one or two atoms of Ring A to form:

i) a 3- to 8-membered partly saturated or saturated carbocycle; or ii) a 3- to 8-membered saturated heterocycle which contains 1, 2 or 3 heteroatoms independently selected from the group consisting of N, O and S;

wherein the said carbocycle or the heterocycle can be unsubstituted or substituted with one or more groups independently selected from the group consisting of $(C_1-C_6)$ alkenyl, $(C_1-C_6)alkyl$, halo$(C_1-C_6)alkyl$, $(C_1-C_6)alkoxy$, hydroxy, halogen, cyano, oxo, $(C_3-C_{10})$cycloalkyl, $(C_6-C_{10})$ aryl, heteroaryl and heterocyclyl;

$R^3$, at each occurrence, is independently selected from the group consisting of hydrogen, halogen, $(C_1-C_6)alkyl$, halo$(C_1-C_6)alkyl$, $(C_3-C_{10})$cycloalkyl, $(C_6-C_{10})aryl$, heteroaryl, heterocyclyl, $(C_6-C_{10})aryl-(C_1-C_6)alkyl$, $(C_1-C_6)alkyl-(C_6-C_{10})aryl$, heterocyclyl-$(C_1-C_6)alkyl$, $(C_1-C_6)alkyl$-heterocyclyl, heteroaryl-$(C_1-C_6)alkyl$, $(C_1-C_6)alkyl$-heteroaryl, cyano, —$NR^{10}R^{11}$, —$C(O)NR^{10}R^{11}$, —$C(S)NR^{10}R^{11}$, —$S(O)_tR^{12}$ and —$C(O)R^{13}$;

$R^4$, at each occurrence, is independently selected from the group consisting of hydrogen, $(C_1-C_6)alkyl$, halo$(C_1-C_6)$ alkyl, halogen, $(C_3-C_{10})$cycloalkyl, $(C_6-C_{10})aryl$, heteroaryl, heterocyclyl, $(C_6-C_{10})aryl-(C_1-C_6)alkyl$, $(C_1-C_6)alkyl-(C_6-C_{10})aryl$, heterocyclyl-$(C_1-C_6)alkyl$, $(C_1-C_6)alkyl$-heterocyclyl, heteroaryl-$(C_1-C_6)alkyl$, $(C_1-C_6)alkyl$-heteroaryl, cyano, —$NR^{10}R^{11}$, —$S(O)_tR^{12}$ and —$C(O)R^{13}$;

$R^5$, at each occurrence, is independently selected from the group consisting of hydrogen, $(C_1-C_6)alkyl$, hydroxy, cyano, —$COR^{10}$, —$NR^{10}R^{11}$, —$CONR^{10}R^{11}$, $(C_1-C_6)alkylamino$, di$(C_1-C_6)alkylamino$, $(C_1-C_6)alkoxy$, halo$(C_1-C_6)alkyl$, —$S(O)_tR^{12}$ and —$C(O)R^{13}$;

$R^6$ and $R^7$ are independently selected from the group consisting of hydrogen, $(C_1-C_6)alkyl$, halo$(C_1-C_6)alkyl$ and halogen;

$R^8$ and $R^9$ are independently selected from the group consisting of hydrogen, deuterium, $(C_1-C_6)alkyl$, halo$(C_1-C_6)alkyl$ and halogen;

or $R^8$ and $R^9$ can combine together to form i) a 3- to 5-membered saturated carbocycle; or ii) a 3- to 5-membered saturated heterocycle which contains 1, 2 or 3 heteroatoms independently selected from the group consisting of N, O and S;

$R^{10}$ is hydrogen, hydroxy, $(C_1-C_6)alkyl$, halo$(C_1-C_6)$ alkyl, $(C_3-C_{10})$cycloalkyl, $(C_6-C_{10})aryl$, heterocyclyl, heteroaryl, $(C_6-C_{10})aryl-(C_1-C_6)alkylene$-, $(C_1-C_6)alkyl-(C_6-C_{10})arylene$-, heterocyclyl-$(C_1-C_6)alkyl$, $(C_1-C_6)alkyl$-heterocyclyl, heteroaryl-$(C_1-C_6)alkyl$ or $(C_1-C_6)alkyl$-heteroaryl;

$R^{11}$ is hydrogen, $(C_1-C_6)alkyl$, halo$(C_1-C_6)alkyl$, $(C_3-C_{10})$cycloalkyl, $(C_6-C_{10})aryl$, heterocyclyl, heteroaryl, $(C_6-C_{10})aryl-(C_1-C_6)alkyl$, $(C_1-C_6)alkyl-(C_6-C_{10})aryl$, heterocyclyl-$(C_1-C_6)alkyl$, $(C_1-C_6)alkyl$-heterocyclyl, heteroaryl-$(C_1-C_6)alkyl$, $(C_1-C_6)alkyl$-heteroaryl or —$S(O)_tR^{12}$;

or $R^{10}$ and $R^{11}$ are combined together to form 3- to 8-membered saturated or unsaturated ring which contains 1, 2 or 3 heteroatoms independently selected from N, O and S;

$R^{12}$ and $R^{13}$ are independently selected from the group consisting of hydrogen, $(C_1-C_6)alkyl$, halo$(C_1-C_6)alkyl$, $(C_3-C_{10})$cycloalkyl, $(C_6-C_{10})aryl$, heterocyclyl, heteroaryl, $(C_6-C_{10})aryl-(C_1-C_6)alkyl$, $(C_1-C_6)alkyl-(C_6-C_{10})aryl$, heterocyclyl-$(C_1-C_6)alkyl$, $(C_1-C_6)alkyl$-heterocyclyl, heteroaryl-$(C_1-C_6)alkyl$ and $(C_1-C_6)alkyl$-heteroaryl;

$R^{14}$ and $R^{15}$ are independently selected from hydrogen, $(C_1-C_6)alkyl$, halo$(C_1-C_6)alkyl$ and halogen; or $R^{14}$ and $R^{15}$ are combined together to form a 3- to 5-membered saturated or unsaturated ring which optionally contains 1 or 2 heteroatoms independently selected from N, O and S;

g is 2, 3, 4, 5 or 6;

m is 0, 1 or 2;

n is 0, 1 or 2;

p is 1, 2 or 3;

r is 0, 1, 2, 3 or 4;

t is 0, 1 or 2;

wherein $(C_1-C_6)alkyl$ is unsubstituted or substituted with one or more groups independently selected from the group consisting of $(C_1-C_6)alkyl$, halogen, halo$(C_1-C_6)alkyl$, hydroxy, $(C_1-C_6)alkoxy$, halo$(C_1-C_6)alkoxy$, $(C_3-C_{10})$cycloalkyl, $(C_6-C_{10})aryl$, $(C_6-C_{10})aryloxy$, heterocyclyl, heteroaryl, amino, cyano, nitro, —NH($C_1$-$C_6$)alkyl, —N[($C_1$-$C_6$)alkyl]$_2$, —C(O)($C_1$-$C_6$)alkyl, —C(O)O($C_1$-$C_6$)alkyl, —C(O)NH$_2$, —C(O)NH($C_1$-$C_6$)alkyl, —C(O)N[($C_1$-$C_6$)alkyl]$_2$ and —C(O)NHSO$_2$($C_1$-$C_6$)alkyl;

($C_3$-$C_{10}$)cycloalkyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, amino, cyano and nitro;

carbocycle is unsubstituted or substituted with one or more groups independently selected from the group consisting of ($C_1$-$C_6$)alkyl, halo($C_1$-$C_6$)alkyl, hydroxy, halogen, ($C_1$-$C_6$)alkoxy, halo($C_1$-$C_6$)alkoxy, ($C_6$-$C_{10}$)aryl, ($C_3$-$C_{10}$)cycloalkyl, heteroaryl, heterocyclyl, amino, cyano, nitro, —C(O)O($C_1$-$C_6$)alkyl, —C(O)NR$^{10}$R$^{11}$ and —S(O)$_t$R$^{12}$; wherein R$^{10}$, R$^{11}$, R$^{12}$ and t are as defined above;

($C_6$-$C_{10}$)aryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)O($C_1$-$C_6$)alkyl, —C(O)NR$^{10}$R$^{11}$ and —S(O)$_t$R$^{12}$; wherein R$^{10}$, R$^{11}$, R$^{12}$ and t are as defined above;

heterocyclyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)NR$^{10}$R$^{11}$ and —S(O)$_t$R$^{12}$; wherein R$^{10}$, R$^{11}$, R$^{12}$ and t are as defined above;

heteroaryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, heterocyclyl, heteroaryl, amino, cyano, nitro, —C(O)NR$^{10}$R$^{11}$ or —S(O)$_t$R$^{12}$; wherein R$^{10}$, R$^{11}$, R$^{12}$ and t are as defined above;

or a stereoisomer, a tautomer or a geometrical isomer thereof or a pharmaceutically acceptable salt, a pharmaceutically acceptable solvate, a prodrug, a polymorph, an N-oxide, a S-oxide or a carboxylic acid isostere thereof.

Representative compounds of Formula (I) encompassed in accordance with the present invention include:

4-(4-((2-(5-(1-Cyanocyclopropyl)thiophen-2-yl)-5-fluorobenzyl)oxy)phenyl)butanoic acid;
3-(4-((2-(5-(1-Cyanocyclopropyl)thiophen-2-yl)-5-fluorobenzyl)oxy)phenyl)propanoic acid;
4-(4-((4-Fluoro-4'-(1-methylcyclopropyl)-[1,1'-biphenyl]-2-yl)methoxy)phenyl)butanoic acid;
4-(4-((4'-(1-Cyanocyclopropyl)-4-fluoro-[1,1'-biphenyl]-2-yl)methoxy)phenyl)butanoic acid;
3-(4-((4'-(1-Cyanocyclopropyl)-4-fluoro-[1,1'-biphenyl]-2-yl)methoxy)phenyl)propanoic acid;
3-(4-((2-(6-(1-Cyanocyclopropyl)pyridin-3-yl)-5-fluorobenzyl)oxy)phenyl)propanoic acid;
4-(4-((4'-Cyclopropyl-4-fluoro-[1,1'-biphenyl]-2-yl)methoxy)phenyl)butanoic acid;
4-(4-((2-(2,3-Dihydro-1H-inden-5-yl)-5-fluorobenzyl)oxy)phenyl)butanoic acid;
4-(4-((5-Fluoro-2-(5,6,7,8-tetrahydronaphthalen-2-yl)benzyl)oxy)phenyl)butanoic acid;
4-(4-((2-(Bicyclo[4.2.0]octa-1(6),2,4-trien-3-yl)-5-fluorobenzyl)oxy)phenyl)butanoic acid;
4-(4-((2-(5-Cyclopropylthiophen-2-yl)-5-fluorobenzyl)oxy)phenyl)butanoic acid;
4-(4-((5-Fluoro-2-(5-(1-hydroxycyclobutyl)thiophen-2-yl)benzyl)oxy)phenyl)butanoic acid;
3-(4-((4-Fluoro-4'-(oxetan-3-yl)-[1,1'-biphenyl]-2-yl)methoxy)phenyl)propanoic acid;
3-(4-((4-Fluoro-4'-(1-hydroxycyclobutyl)-[1,1'-biphenyl]-2-yl)methoxy)phenyl)propanoic acid;
3-(4-((4'-(5,5-Dimethylcyclopent-1-en-1-yl)-4-fluoro-[1,1'-biphenyl]-2-yl)methoxy)phenyl)propanoic acid;
4-(4-((4'-Cyclohexyl-4-fluoro-[1,1'-biphenyl]-2-yl)methoxy)phenyl)butanoic acid;
3-(4-((5-Fluoro-2-(6-(oxetan-3-yl)pyridin-3-yl)benzyl)oxy)phenyl)propanoic acid;
3-(5-((4'-(1-Cyanocyclopropyl)-4-fluoro-[1,1'-biphenyl]-2-yl)methoxy)pyridin-2-yl)propanoic acid;
4-(4-((4-(4-(1-Cyanocyclopropyl)phenyl)pyridin-3-yl)methoxy)phenyl)butanoic acid;
3-(5-((2-(Bicyclo[4.2.0]octa-1(6),2,4-trien-3-yl)-5-fluorobenzyl)oxy)pyridin-2-yl)propanoic acid;
3-(4-((2-(4-(1-Cyanocyclopropyl)phenyl)pyridin-3-yl)methoxy)phenyl)propanoic acid;
4-(4-((2-(2,3-Dihydrobenzofuran-5-yl)-5-fluorobenzyl)oxy)phenyl)butanoic acid;
4-(4-((5-Fluoro-2-(4,5,6,7-tetrahydrobenzo[b]thiophen-2-yl)benzyl)oxy)phenyl)butanoic acid;
4-(4-((2-(6,7-Dihydro-5H-cyclopenta[b]pyridin-3-yl)-5-fluorobenzyl)oxy)phenyl)butanoic acid;
4-(4-((5-Fluoro-2-(7-methylene-4,5,6,7-tetrahydrobenzo[d]thiazol-2-yl)benzyl)oxy)phenyl)butanoic acid;
4-(4-((2-(Bicyclo[4.2.0]octa-1(6),2,4-trien-3-yl)benzyl)oxy)phenyl)butanoic acid;
4-(4-((2-(5,6,7,8-Tetrahydronaphthalen-2-yl)benzyl)oxy)phenyl)butanoic acid;
4-(4-((2-(5-Cyclobutylthiophen-2-yl)-5-fluorobenzyl)oxy)phenyl)butanoic acid;
4-(4-((4'-Cyclopropyl-4-fluoro-3'-methyl-[1,1'-biphenyl]-2-yl)methoxy)phenyl)butanoic acid;
4-(4-((2-(6-Cyclopropylpyridin-3-yl)-5-fluorobenzyl)oxy)phenyl)butanoic acid;
4-(4-((2-(2-Cyclopropylpyrimidin-5-yl)-5-fluorobenzyl)oxy)phenyl)butanoic acid;
4-(4-((2-(4-Cyclopropylthiazol-5-yl)-5-fluorobenzyl)oxy)phenyl)butanoic acid;
4-(4-((2-(2,3-Dihydro-1H-inden-5-yl)benzyl)oxy)phenyl)butanoic acid;
4-(4-((5-Fluoro-2-(5-oxo-5,6,7,8-tetrahydronaphthalen-2-yl)benzyl)oxy)phenyl)butanoic acid;
4-(4-((2-(7,8-Dihydronaphthalen-2-yl)-5-fluorobenzyl)oxy)phenyl)butanoic acid;
4-(4-((5-Fluoro-2-(5-methylene-5,6,7,8-tetrahydronaphthalen-2-yl)benzyl)oxy)phenyl)butanoic acid;
4-(4-((5-Fluoro-2-(5-methyl-7,8-dihydronaphthalen-2-yl)benzyl)oxy)phenyl)butanoic acid;
4-(4-((5-Fluoro-2-(5-methoxy-5,6,7,8-tetrahydronaphthalen-2-yl)benzyl)oxy)phenyl)butanoic acid;
4-(4-((5-Fluoro-2-(5-methoxy-5-methyl-5,6,7,8-tetrahydronaphthalen-2-yl)benzyl)oxy)phenyl)butanoic acid;
4-(4-((5-Fluoro-2-(5-(1-methylcyclopropyl)thiophen-2-yl)benzyl)oxy)phenyl)butanoic acid;
4-(4-((5-Fluoro-2-(5,6,7,8-tetrahydro-4H-cyclohepta[d]thiazol-2-yl)benzyl)oxy)phenyl)butanoic acid;
4-(4-((5-Fluoro-2-(5-(1-fluorocyclopropyl)thiophen-2-yl)benzyl)oxy)phenyl)butanoic acid;
4-(4-((4'-(2,2-Difluorocyclopropyl)-4-fluoro-[1,1'-biphenyl]-2-yl)methoxy)phenyl)butanoic acid;
4-(4-((2-(5-Cyclopropyl-1,3,4-thiadiazol-2-yl)-5-fluorobenzyl)oxy)phenyl)butanoic acid;
4-(4-((2-(5-Cyclopropylthiazol-2-yl)-5-fluorobenzyl)oxy)phenyl)butanoic acid;

4-(4-((5-Fluoro-2-(4,5,6,7-tetrahydrobenzo[d]thiazol-2-yl)benzyl)oxy)phenyl)butanoic acid;

4-(4-((2-(5,6-Dihydro-4H-cyclopenta[d]thiazol-2-yl)-5-fluorobenzyl)oxy)phenyl)butanoic acid;

4-(4-((2-(6,7-Dihydro-4H-pyrano[4,3-d]thiazol-2-yl)-5-fluorobenzyl)oxy)phenyl)butanoic acid;

4-(4-((2-(6,7-Dihydro-4H-pyrano[4,3-d]thiazol-2-yl)-5-fluorobenzyl)oxy)phenyl)butanoic acid;

4-(4-((2-(4-Cyclopropylthiazol-2-yl)-5-fluorobenzyl)oxy)phenyl)butanoic acid;

4-(5-((5-Fluoro-2-(5,6,7,8-tetrahydronaphthalen-2-yl)benzyl)oxy)pyridin-2-yl)butanoic acid;

4-(5-((2-(2,3-Dihydrobenzofuran-5-yl)-5-fluorobenzyl)oxy)pyridin-2-yl)butanoic acid;

4-(5-((5-Fluoro-2-(6-methoxypyridin-3-yl)benzyl)oxy)pyridin-2-yl)butanoic acid;

4-(5-((4'-Cyclopropyl-4-fluoro-[1,1'-biphenyl]-2-yl)methoxy)pyridin-2-yl)butanoic acid;

4-(5-((5-Fluoro-2-(5-methylthiophen-2-yl)benzyl)oxy)pyridin-2-yl)butanoic acid;

4-(5-((2-(Bicyclo[4.2.0]octa-1(6),2,4-trien-3-yl)-5-fluorobenzyl)oxy)pyridine-2-yl)butanoic acid;

4-(5-((4'-(1-cyanocyclopropyl)-4-fluoro-[1,1'-biphenyl]-2-yl)methoxy)pyridin-2-yl)butanoic acid;

4-(5-((5-fluoro-2-(4,5,6,7-tetrahydrobenzo[d]thiazol-2-yl)benzyl)oxy)pyridin-2-yl)butanoic acid;

4-(5-((5-fluoro-2-(5-(1-methylcyclopropyl)thiophen-2-yl)benzyl)oxy)pyridin-2-yl)butanoic acid; or 4-(5-((4-fluoro-2-(4,5,6,7-tetrahydrobenzo[d]thiazol-2-yl)benzyl)oxy)pyridin-2-yl)butanoic acid; and 4-(5-((2-(5-cyclopropylthiophen-2-yl)-4-fluorobenzyl)oxy)pyridin-2-yl)butanoic acid or a stereoisomer, a tautomer or a geometrical isomer thereof; or a pharmaceutically acceptable salt, a pharmaceutically acceptable solvate thereof.

The compounds of the present invention include all stereoisomeric and tautomeric forms and mixtures thereof in all ratios and their pharmaceutically acceptable salts, solvates, prodrugs, polymorphs, N-oxides, S-oxides and carboxylic acid isosteres.

According to another aspect of the present invention, there are provided processes for the preparation of the compounds of formula (I) or pharmaceutically acceptable salts thereof.

Thus, the compounds of formula (I) can be prepared by various methods including using methods well known to a person skilled in the art. Examples of processes for the preparation of a compound of formula I are described below and illustrated in the following scheme but are not limited thereto. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted. Clearly, such factors will also influence the choice of reagent such as bases, solvents, coupling agents to be used in the reaction steps.

The reagents, reactants and intermediates used in the following processes are either commercially available or can be prepared according to standard procedures known in the art, for instance those reported in the literature references.

In the following scheme and the description of general procedures for the preparation of the compounds of formula (I), for ease of reference the starting compounds and the intermediates used for the synthesis of the compounds of the present invention, are designated as compounds 1, 2, 3, 4, 5a, 5b and 6 respectively. In the following scheme general procedure followed for the synthesis of the compounds of formula (I) are referred to as procedure A, B, C and D respectively, for ease of reference.

Thus, the general procedure followed for the preparation of the compounds of formula I is depicted in the following Scheme-1 and Scheme-2.

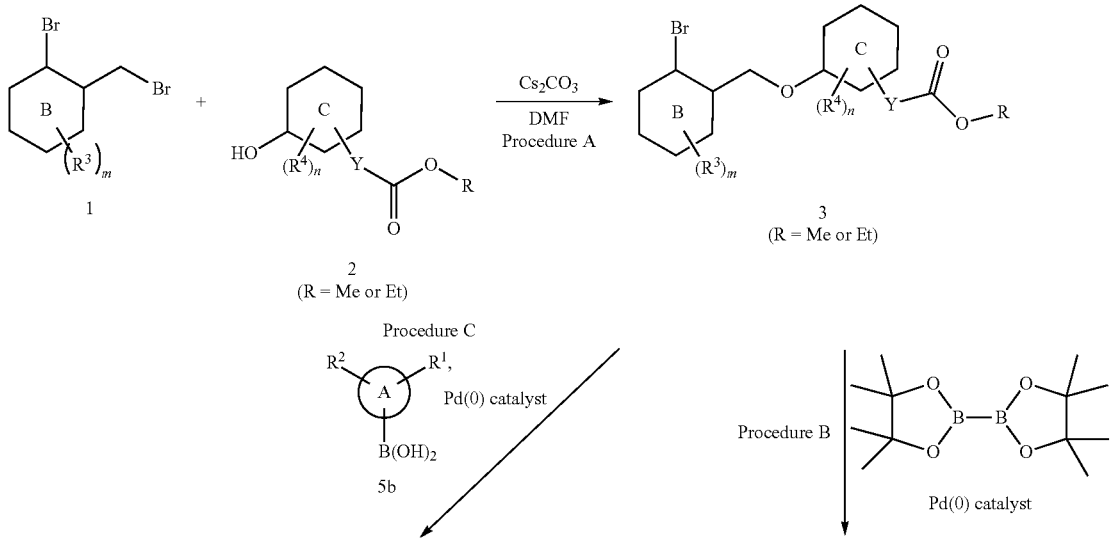

Scheme-1

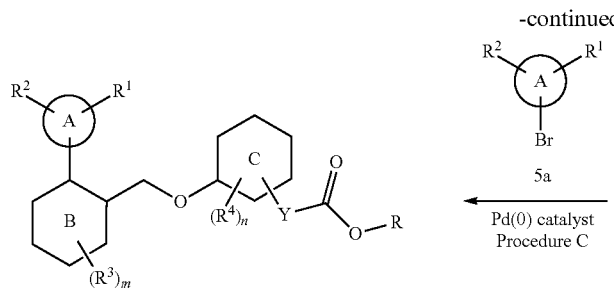

Compound of Formula (I)
(wherein R = Me or Et)

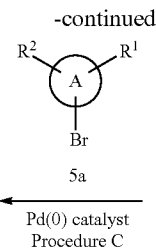

5a

Pd(0) catalyst
Procedure C

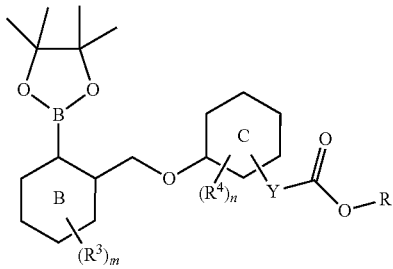

4
(R = Me or Et)

LiOH•H$_2$O  Procedure D

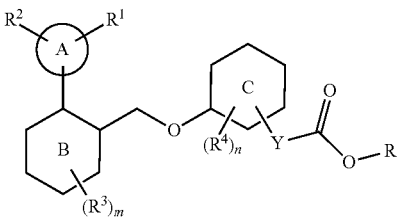

Compound of Formula (I)
(wherein R = H)

General Procedure A:

A mixture of compound 1 (wherein ring B, R$^3$ and m are as defined), compound 2 (wherein ring C, R$^4$, n and Y are as defined and R is methyl or ethyl), cesium carbonate and anhydrous dimethylfomamide (DMF) are stirred at room temperature for 3 h. The reaction mixture is quenched with ice cold water and extracted with ethyl acetate. The obtained organic layer is washed with a brine solution, dried over sodium sulphate, concentrated and purified by flash chromatography to obtain compound 3 (wherein ring B, ring C, R$^3$, R$^4$, m, n and Y are as defined and R is methyl or ethyl).

General Procedure B:

A mixture of the compound 3 as obtained from general Procedure A, bispinacolato diborane [commercially available], potassium acetate, [PdCl$_2$(dppf)]CH$_2$Cl$_2$ [commercially available] and 1,4-dioxane is taken in a round bottom flask and purged with argon for 15-20 mins. The resulting reaction mixture was heated to 80° C. overnight, then cooled to room temperature and filtered over Celite®. The filtrate is concentrated and the residue is dissolved in ethyl acetate. The organic layer is washed with water and with brine solution, dried over sodium sulphate, concentrated and purified by flash chromatography to obtain compound 4 (wherein ring B, ring C, R$^3$, R$^4$, m, n and Y are as defined and R is methyl or ethyl).

General Procedure C

A mixture of compound 5a (wherein ring A, R$^1$ and R$^2$ are as defined), the compound 4 as obtained from general Procedure B, potassium carbonate, a mixture of solvents such as 1,4-dioxane and water is taken in round bottom flask and purged with argon for about 5 mins. Then, tetrakis (triphenylphosphine)palladium(0) [commercially available] is added and purged with argon for about another 5 mins. The resulting reaction mixture is heated to 80° C. overnight, then cooled to room temperature and filtered over Celite®. The filtrate is concentrated and the residue is dissolved in ethyl acetate. The solution is washed with water and brine solution, dried over sodium sulphate, concentrated and purified by flash chromatography to obtain the compound of formula (I) (wherein ring A, ring B, ring C, R$^1$, R$^2$, R$^3$, R$^4$, m, n and Y are as defined and R is methyl or ethyl). The compound of formula (I) (wherein ring A, ring B, ring C, R$^1$, R$^2$, R$^3$, R$^4$, m, n and Y are as defined and R is methyl or ethyl) can also be produced from the compound 3 (obtained from general Procedure A) by direct treatment with compound 5b (wherein ring A, R$^1$ and R$^2$ are as defined), under similar reaction conditions.

General Procedure D

The compound of formula (I) (wherein ring A, ring B, ring C, R$^1$, R$^2$, R$^3$, R$^4$, m, n and Y are as defined and R is methyl or ethyl) obtained from general Procedure C is dissolved in tetrahydrofuran (THF) and methanol and then LiOH.H$_2$O (5 eqv.) in water (2 mL/mM) is added. The resulting reaction mixture is stirred at room temperature for 3 h. The reaction mixture is concentrated in vacuo, acidified with 1N HCl solution and extracted with ethyl acetate. The combined organic layer is washed with brine, dried over sodium sulphate and concentrated under vacuum to obtain compound of formula (I) (wherein ring A, ring B, ring C, R$^1$, R$^2$, R$^3$, R$^4$, m, n and Y are as defined and R is hydrogen).

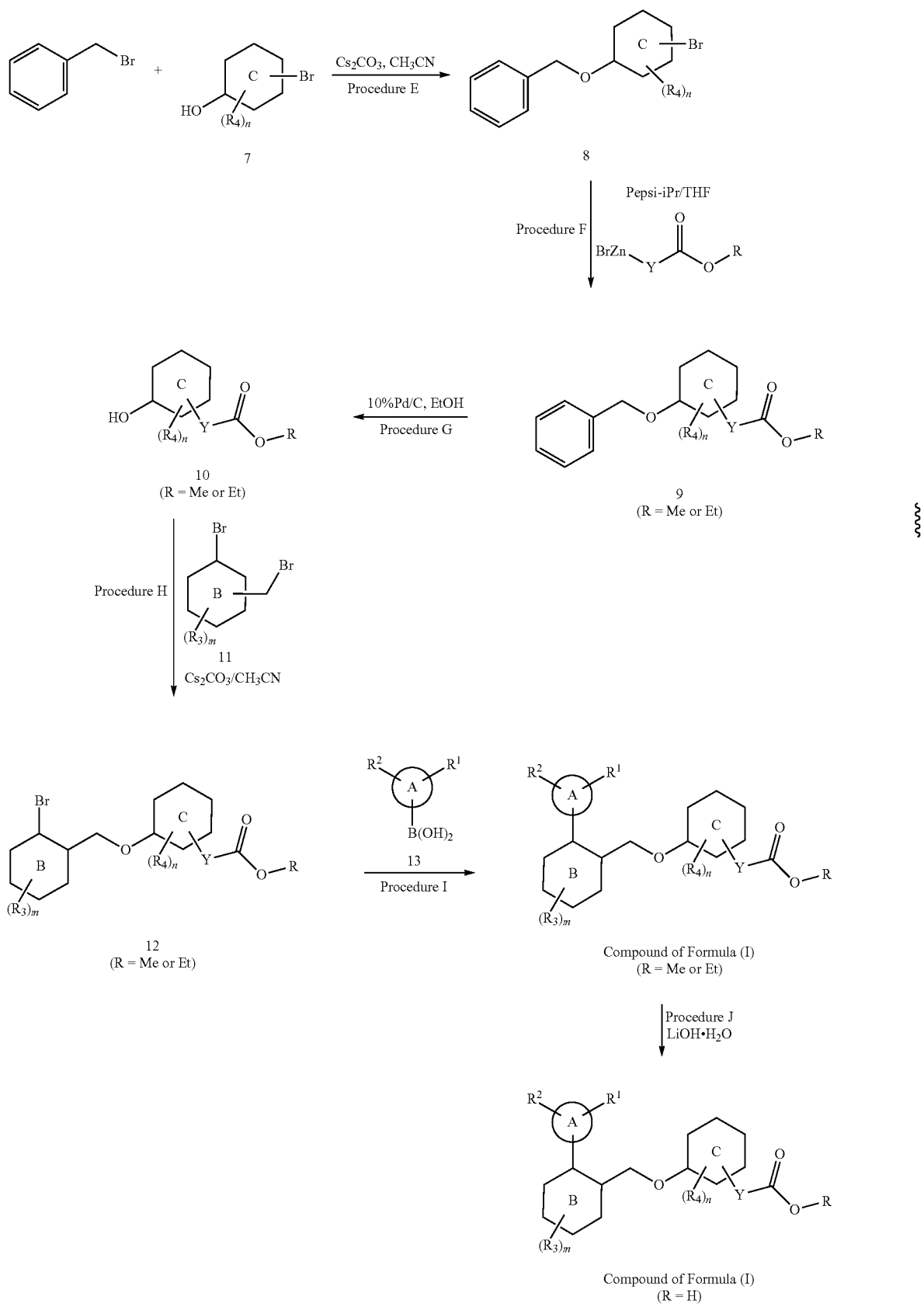
Scheme-2

General Procedure E:

A mixture of benzyl bromide, compound 7 (wherein ring C, $R^4$ and n are as defined), cesium carbonate and acetonitrile are stirred at room temperature for 3 h. The reaction mixture is filtered and washed with ethyl acetate. The combined organic layers are dried over sodium sulphate, concentrated to obtain compound 8 (wherein ring C, $R^4$ and n are as defined).

General Procedure F:

A mixture of the compound 8 as obtained from general Procedure E is stirred in dry THF under argon atmosphere. (4-Ethoxy-4-oxobutyl)zinc(II) bromide in THF is added followed by addition of Pepsi-iPr catalyst. The resulting reaction mixture is stirred overnight at RT. The reaction mixture is decomposed with saturated solution of ammonium chloride and then extracted with ethyl acetate. The organic layer is washed with brine solution, dried over sodium sulphate, concentrated and purified by column chromatography to obtain compound 9 (wherein ring C, $R^4$, n and Y are as defined and R is methyl or ethyl).

General Procedure G:

Compound 9 (wherein ring C, $R^4$, n and Y are as defined and R is methyl or ethyl), obtained from general Procedure F is stirred in dry ethanol. The reaction mixture is set for hydrogenation at 40 psi for 3 h in presence of palladium on carbon (10%) catalyst. The reaction mixture was filtered and concentrated to obtain the compound 10 (wherein ring C, $R^4$, n and Y are as defined and R is methyl or ethyl).

General Procedure H:

The compound 9 as obtained from general Procedure G and compound 11 (wherein $R^3$ and m are as defined) is stirred in acetonitrile. Cesium carbonate is added and reaction mixture is stirred overnight. The resulting reaction mixture is filtered and the residue is washed with ethyl acetate. The combined organic layers are concentrated and purified by flash column chromatography to obtain compound 12 (wherein ring B, ring C, $R^3$, $R^4$, m, n and Y are as defined and R is methyl or ethyl).

General Procedure I:

The compound 12 as obtained from general Procedure H, compound 13 (wherein ring A, $R^1$ and $R^2$ are as defined) and potassium carbonate is stirred in dioxane:water (4:1) mixture and purged with argon for 5 minutes. Palladium tetrakis is added and reaction mixture is stirred at 111° C. for 5 h. The resulting reaction mixture is diluted with ethyl acetate filtered through Celite®, concentrated and purified by flash column chromatography to obtain compound of formula (I) (wherein ring A, ring B, ring C, $R^1$, $R^2$, $R^3$, $R^4$, m, n and Y are as defined and R is methyl or ethyl).

General Procedure J:

The compound of formula (I) (wherein ring A, ring B, ring C, $R^1$, $R^2$, $R^3$, $R^4$, m, n and Y are as defined and R is methyl or ethyl) obtained from general Procedure I is dissolved in tetrahydrofuran (THF) and methanol and then $LiOH.H_2O$ (5 eqv.) in water (2 mL/mM) is added. The resulting reaction mixture is stirred at room temperature for 3 h. The reaction mixture is concentrated in vacuo, acidified with 1N HCl solution and extracted with ethyl acetate. The combined organic layer is washed with brine, dried over sodium sulphate and concentrated under vacuum to obtain compound of formula (I) (wherein ring A, ring B, ring C, $R^1$, $R^2$, $R^3$, $R^4$, m, n and Y are as defined and R is hydrogen).

The compounds of formula (I) can be converted into their pharmaceutically acceptable salts by following procedure known to persons skilled in the art.

The pharmaceutically acceptable salt of the compounds of Formula (I) are prepared with relatively non-toxic acids or bases, depending on the particular substituents found on the compound described herein. When the compounds of Formula (I) of the present invention contain an acidic group they can form an addition salt with a suitable base. For example, pharmaceutically acceptable base addition salts of the compounds of the present invention may include their alkali metal salts such as sodium, potassium, calcium, magnesium, ammonium or an organic base addition salt. Examples of pharmaceutically acceptable organic base addition salts of the compounds of the present invention include those derived from organic bases like lysine, arginine, guanidine, diethanolamine, metformin or other organic bases known to the person skilled in the art.

When the compounds of Formula (I) of the present invention contain one or more basic groups, they can form an addition salt with an inorganic or an organic acid. Examples of pharmaceutically acceptable acid addition salts include those derived from inorganic acids like boric acid, perchloric acid, hydrochloric acid, hydrobromic acid, hydrofluoric acid, hydriodic acid, nitric acid, carbonic acid, monohydrogencarbonic acid, phosphoric acid, monohydrogenphosphoric acid, dihydrogenphosphoric acid, monohydrogensulfuric acid, sulfuric acid, phosphorous acids or other inorganic acids known to the person skilled in the art. Furthermore, examples of pharmaceutically acceptable acid addition salts include the salts derived from organic acids such as acetic acid, propionic acid, isobutyric acid, oxalic acid, malic acid, tartaric acid, citric acid, ascorbic, maleic acid, malonic acid, benzoic acid, succinic acid, suberic acid, fumaric acid, mandelic acid, phthalic acid, benzenesulfonic acid, toluenesulfonic acid, methanesulfonic acid, glucuronic acid, galacturonic acid, naphthoic acid, camphoric acid or other organic acids known to the person skilled in the art. Certain specific compounds of the present invention contain both basic and acidic functionalities that allow the compounds to be converted into either base or acid addition salts.

The pharmaceutically acceptable salts of the present invention can be synthesized from the subject compound i.e. the compound of Formula (I) which contains a basic or acidic moiety by conventional chemical methods. Generally the salts are prepared by contacting the free base or acid with desired salt-forming inorganic or organic acid or a base in a suitable solvent or dispersant or by anion exchange or cation exchange with other salts. Suitable solvents are, for example, ethyl acetate, ethers, alcohols, acetone, or mixtures of these solvents.

Those skilled in the art will recognize that the compounds of Formula (I) of the present invention contain asymmetric or chiral centers, and therefore exist in different stereoisomeric forms, as racemic mixtures of enantiomers, mixtures of diastereomers or enantiomerically or optically pure compounds. The term "chiral" refers to molecules which have the property of non-superimposability of the mirror image cohort, while the term "achiral" refers to molecules which are superimposable on their mirror image partner. It is intended that all stereoisomeric forms of the compounds of the invention, including but not limited to, diastereomers and enantiomers, as well as mixtures thereof such as racemic mixtures, geometric isomers form part of the present invention.

When the compounds of Formula (I) of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation. Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%. When a compound of Formula (I) of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

The isotopically labeled forms of compounds of Formula (I), can be prepared by conventional techniques known to those skilled in the art or by processes analogous to those described above or in the subsequent section on examples by using a corresponding isotopically labeled reagent in place of the non-labeled reagent.

In one embodiment, the compounds of Formula (I) exists as tautomers, and it is intended to encompass all the tautomeric forms of the compounds within the scope of the present invention.

The present invention furthermore includes all the solvates of the compounds of Formula (I), for example, hydrates and the solvates formed with other solvents of crystallisation, selected from alcohols such as methanol, ethanol, 1-propanol or 2-propanol, ethers such as diethyl ether, isopropyl ether or tetrahydrofuran, esters such as methyl acetate or ethyl acetate, ketone such as acetone or their mixtures thereof. Certain compounds of the present invention can exist in unsolvated forms as well as solvated forms, including hydrated forms.

It is further intended to encompass various polymorphs of compounds of Formula (I) within the scope of the present invention. Various polymorphs of compounds of the present invention can be prepared by standard crystallisation procedures known in the art. The crystallisation technique employed can utilize various solvents or their mixtures, temperature conditions and various modes of cooling, ranging from very fast to very slow cooling. The presence of polymorphs can be determined by IR (Infra-red) spectroscopy, solid probe NMR (Nuclear Magnetic Resonance) spectroscopy, differential scanning calorimetry, powder X-ray diffraction or such other standard techniques.

Furthermore, the present invention also includes prodrugs of the compounds of Formula (I). The prodrugs of the compounds of the present invention are derivatives of the aforesaid compounds of the invention which upon administration to a subject in need thereof undergoes chemical conversion by metabolic or chemical processes to release the parent drug in vivo from which the prodrug is derived. The preferred prodrugs are pharmaceutically acceptable ester derivatives e.g., alkyl esters, cycloalkyl esters, alkenyl esters, benzyl esters, mono- or di-substituted alkyl esters convertible by solvolysis under physiological conditions to the parent carboxylic acid, and those conventionally used in the art.

The present invention further relates to carboxylic acid isosteres of the compounds of Formula (I).

The present invention also relates to N-oxide derivatives of the compounds of Formula (I).

The present invention also relates to S-oxide derivatives of the compounds of Formula (I).

In one aspect of the present invention, i.e. the compounds of Formula (I) are GPR120 agonists.

In an embodiment of the present invention, the compounds of Formula (I) find use in the treatment or prophylaxis of a disease or a disorder mediated by GPR120.

In another aspect, the present invention relates to a method for the treatment or prophylaxis of a disease or a disorder mediated by GPR120, comprising administering to a subject in need thereof, a therapeutically effective amount of a compound of Formula (I) or a stereoisomer, a tautomer or a geometrical isomer thereof or a pharmaceutically acceptable salt thereof.

In an embodiment, the present invention relates to use of the compound of Formula (I) or a stereoisomer or a tautomer or a pharmaceutically acceptable salt thereof for the treatment or prophylaxis of a disease or a disorder mediated by GPR120.

According to one embodiment, the present invention relates to use of the compounds of Formula (I) or a stereoisomer or a tautomer or a pharmaceutically acceptable salt thereof; in the manufacture of a medicament for the treatment or prophylaxis of a disease or a disorder mediated by GPR120.

As used herein, the term "a disease or a disorder mediated by GPR120" or "GPR120 mediated disease(s) or condition(s)" refers to a disease or a disorder or a condition characterized by inappropriate, for example, less than or greater than normal, GPR120 activity. A GPR120-mediated disease or disorder may be completely or partially mediated by inappropriate GPR120 activity.

In an embodiment of the invention, the disease or condition mediated by GPR120 is selected from the group consisting of diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, cardiovascular disease, atherosclerosis, kidney disease, polycystic ovary syndrome, ketoacidosis, thrombotic disorders, nephropathy, diabetic neuropathy, diabetic retinopathy, sexual dysfunction, fatty liver development, dermatopathy, dyspepsia, hypoglycemia, cancer, edema and a disorder related to glucose levels such as pancreatic beta cell regeneration.

In an embodiment of the invention, the disease or condition mediated by GPR120 is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic neuropathy, diabetic retinopathy, metabolic syndrome, hypertension and pancreatic beta cell degeneration.

In an embodiment of the invention, the disease or condition mediated by GPR120 is selected from the group consisting of diabetes, obesity, insulin resistance, hyperglycemia, glucose intolerance, metabolic syndrome and pancreatic beta cell degeneration.

In an embodiment, diabetes is Type 2 diabetes.

In an embodiment, the disease or disorder mediated by GPR120 is a metabolic disorder which refers to one or more diseases or conditions as identified above.

In an embodiment, the disease or disorder mediated by GPR120 is an inflammatory disorder.

Accordingly, the present invention relates to a method for the treatment or prophylaxis of a metabolic disorder, comprising administering to a subject in need thereof a therapeutically amount of a compound of Formula (I) or a stereoisomer or a tautomer or a pharmaceutically acceptable salt thereof.

In an embodiment, the present invention provides use of the compound of Formula (I) or a stereoisomer or a tautomer or a pharmaceutically acceptable salt thereof for the treatment or prophylaxis of a metabolic disorder.

According to one embodiment, the present invention relates to use of the compounds of Formula (I) or pharmaceutically acceptable salts thereof in the manufacture of a medicament, for the treatment or prophylaxis of a metabolic disorder.

The term "metabolic disorder" as used herein refers a disorder relating to abnormality of metabolism. Accordingly, in the context of the present invention all the disorders relating to abnormality of metabolism are encompassed in the term "metabolic disorders".

In one embodiment, the metabolic disorder is selected from the group consisting of diabetes, obesity, cardiovascular disease, hypertension, ketoacidosis, insulin resistance, glucose intolerance, hyperglycemia, hypertriglylceridemia, polycystic ovary syndrome, hypercholesterolemia, hyperlipoproteinemia, dyslipidemia, metabolic syndrome, hyperlipidemia, diabetic neuropathy, diabetic retinopathy, edema and related disorders associated with abnormal plasma lipoprotein, triglycerides and pancreatic beta cell degeneration.

The term "diabetes mellitus" or "diabetes" refers to a chronic disease or condition, which occurs when the pancreas does not produce enough insulin, or when the body cannot effectively use the insulin it produces. This leads to an increased concentration of glucose in the blood (hyperglycaemia). Two major forms of diabetes are Type 1 diabetes (Insulin-dependent diabetes mellitus) and Type 2 diabetes (Non-insulin dependent diabetes mellitus (NIDDM)). Type 1 diabetes is an autoimmune condition in which the insulin-producing β-cells of the pancreas are destroyed which generally results in an absolute deficiency of insulin, the hormone that regulates glucose utilization. Type 2 diabetes often occurs in the face of normal or even elevated levels of insulin and can result from the inability of tissues to respond appropriately to insulin. Other categories of diabetes include gestational diabetes (a state of hyperglycemia which develops during pregnancy) and "other" rarer causes (genetic syndromes, acquired processes such as pancreatitis, diseases such as cystic fibrosis, exposure to certain drugs, viruses, and unknown causes). In an embodiment, diabetes refers to Type 2 diabetes.

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

The term "cardiovascular disease" as used herein refers to any disease of the heart or blood vessels. One or more diseases of heart encompassed in the term "cardiovascular disease" is selected from, but not limited to, angina, arrhythmia, coronary artery disease (CAD), cardiomyopathy, myocardial infarction, heart failure, hypertrophic cardiomyopathy, mitral regurgitation, mitral valve prolapse, pulmonary stenosis, etc. The blood vessel disease encompassed in the term "cardiovascular diseases", is selected from, but not limited to, for example, peripheral vascular disease, artery disease, carotid artery disease, deep vein thrombosis, venous diseases, atherosclerosis and the like.

In an embodiment, the metabolic disorder is selected from the group consisting of diabetes, obesity, insulin resistance, hyperglycemia, glucose intolerance, hypercholesterolemia, hypertriglylceridemia, dyslipidemia, hyperlipoproteinemia, hyperinsulinemia, atherosclerosis, diabetic neuropathy, diabetic retinopathy, metabolic syndrome, hypertension and pancreatic beta cell degeneration.

In an embodiment, the metabolic disorder is selected from the group consisting of diabetes, obesity, insulin resistance, glucose intolerance, dyslipidemia, hyperinsulinemia, metabolic syndrome and pancreatic beta cell degeneration.

In an embodiment, the metabolic disorder is Type 2 diabetes.

Pharmaceutical Compositions

The present invention furthermore relates to pharmaceutical compositions that contain a therapeutically effective amount of at least one compound of Formula (I) or its pharmaceutically acceptable salt in addition to a customary pharmaceutically acceptable carrier, and to a process for the production of a pharmaceutical composition, which includes bringing at least one compound of Formula (I), into a suitable administration form using a pharmaceutically suitable and physiologically tolerable excipient and, if appropriate, further suitable active compounds, additives or auxiliaries.

According to one embodiment, the present invention relates to a pharmaceutical composition comprising the compounds of Formula (I) or pharmaceutically acceptable salts thereof and one or more pharmaceutically acceptable excipients; for use as GPR120 agonists and in the treatment or prophylaxis of a disease or a condition mediated by GPR120.

The term "pharmaceutically acceptable carrier" as used herein means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

It is further intended to include within the scope of the present invention the use of the compounds of Formula (I) or its pharmaceutically acceptable salts thereof in combination with at least one therapeutically active agent.

According to one embodiment, the present invention provides a pharmaceutical composition, comprising a therapeutically effective amount of a compound of Formula (I) or a pharmaceutically acceptable salt thereof and at least one further therapeutically active agent, together with a pharmaceutically acceptable carrier.

In an embodiment, the present invention relates to use of the compound of Formula (I) or a pharmaceutically acceptable salt thereof; in combination with a further therapeutically active compound, in the treatment or prophylaxis of a disease or a condition mediated by GPR120.

The therapeutically active agent used in combination with one or more of the compounds of Formula (I) can be selected from the compounds or active substances known to be used in the treatment of diabetes and other conditions such as obesity, insulin resistance, hyperglycemia, glucose intolerance, hypercholesterolemia, hypertriglylceridemia, dyslipidemia, hyperlipoproteinemia, hyperinsulinemia or atherosclerosis. According to the present invention, the therapeutically active agent, used in combination with the compounds of Formula (I) of the present invention can be selected from, but not limited to, insulin, sulfonylureas, biguanidines, meglitinides, oxadiazolidinediones, thiazolidinediones, glucosidase inhibitors, inhibitors of glycogen phosphorylase, glucagon antagonists, HMGCoA reductase inhibitor, GLP-1 (Glucogen-like peptide-1) agonists, potassium channel openers, inhibitors of dipeptidylpeptidase IV (DPP-IV), diglyceride acyltransferase (DGAT) inhibitor, insulin sensitizers, modulators of glucose uptake, modulators of glucose transport and modulators of glucose reabsorption, modulators of the sodium-dependent glucose transporter 1 or 2 (SGLT1, SGLT2), compounds which alter lipid metabolism such as antihyperlipidemic active ingredients and antilipidemic active ingredients, PPARgamma agonists and agents with combined PPARalpha and gamma activity and active ingredients which act on the ATP-dependent potassium channel of the beta cells.

In an embodiment, the compound of Formula (I) can be used in combination with a PPAR gamma agonist selected from rosiglitazone, pioglitazone, rivoglitazone and the like.

In an embodiment, the compound of Formula (I) can be used in combination with a HMGCoA reductase inhibitor selected from simvastatin, fluvastatin, pravastatin, lovastatin, atorvastatin, cerivastatin, rosuvastatin and the like.

In an embodiment, the compound of Formula (I) can be used in combination with a sulfonylurea selected from tolbutamide, glibenclamide, glipizide, glimepiride and the like.

In another embodiment, the compound of the Formula (I) can be used in combination with a meglitinide selected from repaglinide, nateglinide, mitiglinide and the like.

In another embodiment, the compound of the Formula (I) can be used in combination with GLP-1 agonist selected from exenatide, liraglutide, taspoglutide albiglutide, lixisenatide and the like.

In another embodiment, the compound of the Formula (I) can be used in combination with DPP-IV inhibitor selected from alogliptin, gemigliptin, linagliptin, saxagliptin, sitagliptin, vildagliptin and the like.

Accordingly, in an embodiment the further therapeutically active agent that can be used in combination with one or more compounds of Formula (I) encompassed in the present invention, can be selected from one or more of the agents including, but not limited to, insulin, rosiglitazone, pioglitazone, rivoglitazone, simvastatin, fluvastatin, pravastatin, lovastatin, atorvastatin, cerivastatin, rosuvastatin, tolbutamide, glibenclamide, glipizide, glimepiride, repaglinide, nateglinide, mitiglinide, exenatide, liraglutide, taspoglutide albiglutide, lixisenatide, alogliptin, gemigliptin, linagliptin, saxagliptin, sitagliptin, vildagliptin and the like.

The pharmaceutical compositions according to the present invention are prepared in a manner known and familiar to one skilled in the art. Pharmaceutically acceptable inert inorganic and/or organic carriers and/or additives can be used in addition to the compounds of Formula (I) and/or its pharmaceutically acceptable salts. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

Further, the pharmaceutical composition of the present invention also contains additives such as, for example, fillers, antioxidants, emulsifiers, preservatives, flavours, solubilisers or colourants. The pharmaceutical composition of the present invention may also contain two or more compounds of Formula (I) and/or its pharmaceutically acceptable salts, the pharmaceutical compositions can also contain one or more other therapeutically or prophylactically active ingredients.

The pharmaceutical compositions normally contain about 1 to 99%, for example, about 10 to 80%, by weight of the compounds of Formula (I) or their pharmaceutically acceptable salts.

The amount of the active ingredient, the compound of Formula (I) or its pharmaceutically acceptable salt in the pharmaceutical compositions can, for example, vary from about 1 to 500 mg. In case of higher body weight of the mammal in need of the treatment, the pharmaceutical composition may contain the compound of Formula (I) in an amount ranging from 5 mg to 1000 mg. The desirable dosage of the compounds of Formula (I) can be selected over a wide range. The daily dosage to be administered is selected to achieve the desired therapeutic effect in subjects being treated for metabolic disorders. A dosage of about 0.05 to 50 mg/kg/day of the compounds of Formula (I) or its pharmaceutically acceptable salt may be administered. In case of higher body weight of the mammal in need of the treatment, a dosage of about 0.1 to 100 mg/kg/day of the compound of Formula (I) or its pharmaceutically acceptable salt may be administered. If required, higher or lower daily dosages can also be administered. Actual dosage levels of the active ingredients in the pharmaceutical composition of this present invention can be varied so as to obtain an amount of the active ingredient, which is effective to achieve the desired therapeutic response for a particular patient, composition, and mode of administration without being toxic to the patient. The selected dosage level can be readily determined by a skilled medical practitioner in the light of the relevant circumstances, including the condition (diseases or disorder) to be treated, the chosen route of administration depending on a number of factors, such as age, weight and physical health and response of the individual patient, pharmacokinetics, severity of the disease and the like, factors known in the medical art.

The pharmaceutical compositions according to the present invention can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

It is understood that modifications that do not substantially affect the activity of the various embodiments of this invention are included within scope of the invention disclosed herein. Accordingly, the following examples are intended to illustrate but not to limit scope of the present invention.

The abbreviations and terms that are used herein:

LIST OF ABBREVIATIONS

| | | | |
|---|---|---|---|
| ATP | Adenosine triphosphate | mM | Millimolar |
| DCM | Dichloromethane | min(s) | Minute(s) |
| DMF | N,N-dimethyl formamide | nM | Nanomolar |
| DMSO | Dimethyl sulfoxide | nm | Nanometer |
| TFA | Trifluoroacetic acid | μl | Microlitre |
| NaOH | Sodium hydroxide | ml | Millilitre |
| EtOH | Ethanol | μM | Micromolar |
| PTSA | p-Toluenesulfonic acid | pM | Picomolar |
| eqv | Equivalent | NaH | Sodium hydride |
| g | gram | NaHCO$_3$ | Sodium bicarbonate |
| h | Hour(s) | Na$_2$CO$_3$ | Sodium carbonate |
| HCl | Hydrochloric acid | Na$_2$SO$_4$ | Sodium sulfate |
| IPA | Isopropyl alcohol | NH$_4$Cl | Ammonium chloride |
| K$_2$CO$_3$ | Potassium carbonate | THF | Tetrahydrofuran |
| l | litre | PET | Petroleum Ether |
| LiOH•H$_2$O | Lithium hydroxide monohydrate | PPh$_3$ | Triphenylphosphine |
| MeOH | Methanol | Tris HCl | Tris Hydrochloride |
| DMF•DMA | N,N-dimethyl formamide dimethyl acetal | | |
| TLC | Thin Layer Chromatography | | |
| PdCl$_2$(dppf)-CH$_2$Cl$_2$ | [1,1'-Bis(diphenylphosphino)ferrocene]dichloropalladium(II), complex with dichloromethane | | |
| DAST | Diethylaminosulfur trifluoride | | |
| POCl$_3$ | Phosphorous trichloride | | |
| MeMgBr | Methylmagnesium bromide | | |
| RT | Room temperature (20° C.-25° C.) | | |

Example 1

4-(4-((2-(5-(1-Cyanocyclopropyl)thiophen-2-yl)-5-fluorobenzyl)oxy)phenyl)butanoic acid Step 1a Synthesis of methyl-4-(4-((2-bromo-5-fluorobenzyl)oxy)phenyl)butanoate According to general procedure A (as described herein above), 1-bromo-2-(bromomethyl)-4-fluorobenzene (1 g, 3.73 mM), was coupled with methyl 4-(4-hydroxyphenyl) butanoate (0.797 g, 4.11 mM), to give the title compound, methyl 4-(4-((2-bromo-5-fluorobenzyl)oxy)phenyl)butanoate. Yield: 1.39 g, 3.65 mM, 98%; $^1$H NMR (CDCl$_3$, 500 MHz) δ 7.52-7.58 (m, 1H), 7.20-7.38 (m, 1H), 7.13 (d, J=8.5 Hz, 2H), 6.98-6.96 (m, 3H), 5.08 (s, 2H), 3.68 (s, 3H), 2.62 (t, J=8 Hz, 2H), 2.34 (t, J=7.5 Hz, 2H), 1.90-2.0 (m, 2H); MS (m/z); 404.2 [M+Na$^+$].

Step 1b

Synthesis of methyl 4-(4-((5-fluoro-2-(4,4,5,5-tetramethyl-1,3,2-dioxaborolan-2-yl)benzyl)oxy)phenyl)butanoate The compound obtained in step 1a, methyl 4-(4-((2-bromo-5-fluorobenzyl)oxy)phenyl)butanoate (1.5 g, 3.93 mM), was coupled with bis(pinacolato)diboron (1.49 g, 5.90 mM) in the presence of potassium acetate (1.16 g, 11.80 mM), PdCl$_2$(dppf)-CH$_2$Cl$_2$ adduct (0.064 g, 0.079 mM) and 1,4-dioxane according to the general procedure B (as described herein above), to give the title compound, methyl 4-(4-((5-fluoro-2-(4,4,5,5-tetramethyl-1,3,2-dioxaborolan-2-yl)benzyl)oxy)phenyl)butanoate. Yield: 1.6 g, 3.74 mM, 95%; $^1$H NMR (CDCl$_3$, 500 MHz) δ: 7.85 (t, J=7 Hz, 1H), 7.31 (d, J=10 Hz, 1H), 7.10 (d, J=8.5 Hz, 2H), 6.99 (m, 1H), 6.91 (d, J=8 Hz, 2H), 5.35 (s, 2H), 3.68 (s, 3H), 2.61 (t, J=7.5 Hz, 2H), 2.34 (t, J=7.5 Hz, 2H), 1.90-2.0 (m, 2H), 1.30 (m, 12H); MS (m/z) 451.2 [M+Na$^+$].

Step 1c

Synthesis of methyl 4-(4-((2-(5-(1-cyanocyclopropyl)thiophen-2-yl)-5-fluorobenzyl)oxy)phenyl)butanoate The compound obtained in step 1b, methyl 4-(4-((5-fluoro-2-(4,4,5,5-tetramethyl-1,3,2-dioxaborolan-2-yl)benzyl)oxy)phenyl)butanoate (0.150 g, 0.350 mM), was coupled with 1-(5-bromothiophen-2-yl)cyclopropanecarbonitrile (0.067 g, 0.292 mM) in the presence of potassium carbonate (0.121 g, 0.876 mM) 1,4-dioxane (5 mL), water (1.25 mL) and tetrakis(triphenylphosphine)palladium(0) (0.017 g, 0.015 mM), according to the general procedure C (as described herein above), to give the title compound, methyl 4-(4-((2-(5-(1-cyanocyclopropyl)thiophen-2-yl)-5-fluorobenzyl)oxy)phenyl)butanoate. Yield: 0.109 g, 0.242 mM, 83%; $^1$H NMR (CDCl$_3$, 500 MHz) δ 7.38-7.43 (m, 1H), 7.36 (d, J=9.0 Hz, 1H), 7.10 (d, J=8.5 Hz, 2H), 7.05-7.09 (m, 1H), 7.02 (d, J=4.0 Hz, 1H), 6.91 (d, J=3.5 Hz, 1H) 6.84 (d, J=8.5 Hz, 2H), 5.00 (s, 2H), 3.68 (s, 3H), 2.61 (t, J=7.5 Hz, 2H), 2.34 (t, J=7.5 Hz, 2H), 1.59-2.0 (m, 2H), 1.60-1.80 (m, 2H), 1.40-1.50 (m, 2H); MS m/z 472.3 [M+Na$^+$].

Step 1d

Synthesis of 4-(4-((2-(5-(1-Cyanocyclopropyl)thiophen-2-yl)-5-fluorobenzyl)oxy)phenyl)butanoic acid Methyl 4-(4-((2-(5-(1-cyanocyclopropyl)thiophen-2-yl)-5-fluorobenzyl)oxy)phenyl)butanoate (compound obtained in step 1c) (0.095 g, 0.211 mM) was hydrolysed by LiOH:H$_2$O (0.044 g, 1.057 mM), according to the general procedure D (as described herein above), to give the title compound, 4-(4-((2-(5-(1-cyanocyclopropyl)thiophen-2-yl)-5-fluorobenzyl)oxy)phenyl)butanoic acid. Yield: 0.076 g, 0.175 mM, 83%; $^1$H NMR (DMSO-d$_6$, 500 MHz) δ 12.04 (s, 1H), 7.52 (t, J=8.0 Hz, 1H), 7.42 (d, J=9.5 Hz, 1H), 7.25-7.35 (m, 1H), 7.05-7.15 (m, 4H), 6.88 (d, J=8.5 Hz, 2H), 5.03 (s, 2H), 2.50-2.70 (m, 2H), 2.19 (t, J=7.5 Hz, 2H), 1.80-1.85 (m, 2H), 1.70-1.79 (m, 2H), 1.48-1.53 (m, 2H); MS (m/z) 458.2 [M+Na$^+$].

Example 2

3-(4-((2-(5-(1-Cyanocyclopropyl)thiophen-2-yl)-5-fluorobenzyl)oxy)phenyl)propanoic acid Step 2a Synthesis of ethyl 3-(4-((2-bromo-5-fluorobenzyl)oxy)phenyl)propanoate According to general procedure A (as described herein above), 1-bromo-2-(bromomethyl)-4-fluorobenzene (1.517 g, 5.66 mM) was coupled with ethyl 3-(4-hydroxyphenyl)propanoate (1 g, 5.15 mM), to give the title compound, ethyl 3-(4-((2-bromo-5-fluorobenzyl)oxy)phenyl)propanoate. Yield: 1.6 g, 4.20 mM, 82%; $^1$H NMR (CDCl$_3$, 300 MHz) δ 7.50-7.60 (m, 1H), 7.30-7.38 (m, 1H), 7.1 (d, J=8.4 Hz, 2H), 6.80-7.00 (m, 3H), 5.07 (s, 2H), 4.13 (q, J=7.2 Hz, 2H), 2.92 (t, J=7.5 Hz, 2H), 2.60 (t, J=7.8 Hz, 2H), 1.25 (t, J=7.2 Hz, 3H); MS (m/z) 382.3 [M+H$^+$].

Step 2b

Synthesis of ethyl 3-(4-((5-fluoro-2-(4,4,5,5-tetramethyl-1,3,2-dioxaborolan-2-yl)benzyl)oxy)phenyl)propanoate The compound obtained in step 2a, ethyl 3-(4-((2-bromo-5-fluorobenzyl)oxy)phenyl)propanoate (1.5 g, 3.93 mM), was coupled with bis(pinacolato)diboron (1.499 g, 5.90 mM), potassium acetate (1.158 g, 11.80 mM), PdCl$_2$(dppf)-CH$_2$Cl$_2$ adduct (0.064 g, 0.079 mM) and 1,4-dioxane, according to the general procedure B (as described herein above), to give the title compound, ethyl 3-(4-((5-fluoro-2-(4,4,5,5-tetramethyl-1,3,2-dioxaborolan-2-yl)benzyl)oxy)phenyl)propanoate. Yield: 1.6 g, 3.74 mM, 95%; $^1$H NMR (CDCl$_3$, 300 MHz) δ 7.80-7.90 (m, 1H), 7.25-7.35 (m, 1H), 7.12 (d, J=8.4 Hz, 2H), 6.95-7.05 (m, 1H), 6.90 (d, J=8.4 Hz, 2H), 5.35 (s, 2H), 4.13 (q, J=6.9 Hz, 2H), 2.91 (t, J=7.8 Hz, 2H), 2.60 (t, J=8.1 Hz, 2H), 1.32 (s, 12H), 1.24 (t, J=7.2 Hz, 3H); MS m/z 429.2 [M+H$^+$].

Step 2c

Synthesis of ethyl 3-(4-((2-(5-(1-cyanocyclopropyl)thiophen-2-yl)-5-fluorobenzyl)oxy)phenyl)propanoate The title compound was prepared in an analogous manner as Example 1 involving the reaction of ethyl 3-(4-((5-fluoro-2-(4,4,5,5-tetramethyl-1,3,2-dioxaborolan-2-yl)benzyl)oxy)phenyl)propanoate (compound of step 2b) (0.150 g, 0.350 mM) with 1-(5-bromothiophen-2-yl)cyclopropanecarbonitrile (0.067 g, 0.292 mM), according to the general procedure C (as described herein above). Yield: 0.120 g, 0.267 mM, 91%; $^1$H NMR (CDCl$_3$, 500 MHz) δ 7.38-7.43 (m, 1H), 7.35 (d, J=10.0 Hz, 1H), 7.13 (d, J=8.0 Hz, 2H), 7.05-7.15 (m, 1H), 7.03 (d, J=4.0 Hz, 1H), 6.90 (d, J=3.0 Hz, 1H) 6.84 (d, J=8.5 Hz, 2H), 5.00 (s, 2H), 4.14 (q, J=7.0 Hz, 2H), 2.91 (t, J=8.0 Hz, 2H), 2.60 (t, J=8.0 Hz, 2H), 1.75-1.85 (m, 2H), 1.40-1.50 (m, 2H), 1.25 (t, J=7.0 Hz, 3H); MS (m/z) 472.3 [M+Na$^+$].

Step 2d 3-(4-((2-(5-(1-Cyanocyclopropyl)thiophen-2-yl)-5-fluorobenzyl)oxy)phenyl)propanoic acid The title compound was prepared in an analogous manner as Example 1 involving the reaction of ethyl 3-(4-((2-(5-(1-cyanocyclopropyl)thiophen-2-yl)-5-fluorobenzyl)oxy)phenyl)propanoate (compound obtained in step 2c) (0.100 g, 0.222 mM) with LiOH.H$_2$O (9.33 mg, 0.222 mM), according to the general procedure D (as described herein above). Yield: 0.082 g, 0.195 mM, 87%; $^1$H NMR (DMSO-d$_6$, 500 MHz) δ 12.09 (s, 1H), 7.45-7.55 (m, 1H), 7.47 (t, J=9.5 Hz, 1H), 7.25-7.35 (m, 1H), 7.14 (d, J=8.0 Hz, 2H), 7.05-7.10 (m, 2H), 6.87 (d, J=8.5 Hz, 2H), 5.03 (s, 2H), 2.75 (t, J=7.5 Hz, 2H), 2.45-2.50 (m, 2H), 1.75-1.85 (m, 2H), 1.45-1.55 (m, 2H); MS (m/z) 444.2 [M+Na$^+$].

Example 3

4-(4-((4-Fluoro-4'-(1-methylcyclopropyl)-[1,1'-biphenyl]-2-yl)methoxy)phenyl)butanoic acid Step 3a Synthesis of methyl 4-(4-((4-fluoro-4'-(1-methylcyclopropyl)-[1,1'-biphenyl]-2-yl)methoxy)phenyl)butanote The title compound was prepared in an analogous manner as Example 1 involving the reaction of 1-bromo-4-(1-methylcyclopropyl)benzene (0.049 g, 0.233 mM) was coupled with methyl 4-(4-((5-fluoro-2-(4,4,5,5-tetramethyl-1,3,2-dioxaborolan-2-yl)benzyl)oxy)phenyl)butanoate (compound obtained in step 1b of Example 1) (0.150 g, 0.350 mM), potassium carbonate (0.097 g, 0.700 mM), in presence of tetrakis(triphenyl)phosphine)palladium(0) (0.013 g, 0.012 mM), according to general procedure C (as described herein above). Yield: 0.050 g, 0.116 mM, 49.5%; $^1$H NMR (CDCl$_3$, 300 MHz) δ 7.30-7.38 (m, 1H), 7.20-7.30 (m, 5H), 7.00-7.10 (m, 3H), 6.78 (d, J=8.0 Hz, 2H), 4.91 (s, 2H), 3.66 (s, 3H), 2.58 (t, J=7.2 Hz, 2H), 2.31 (t, J=7.2 Hz, 2H), 1.85-1.95 (m, 2H), 1.45 (s, 3H), 0.91 (bt, J=6.3 Hz, 2H), 0.79 (bt, J=3.5 Hz, 2H); MS (m/z) 433.3 [M+H$^+$].

Step 3b

Synthesis of 4-(4-((4-fluoro-4'-(1-methylcyclopropyl)-[1,1'-biphenyl]-2-yl)methoxy)phenyl)butanoic acid The title compound was prepared in an analogous manner as Example 1 involving the reaction of methyl 4-(4-((4-fluoro-4'-(1-methylcyclopropyl)-[1,1'-biphenyl]-2-yl)methoxy)phenyl)butanoate (compound obtained in step 3a) (0.038 g, 0.088 mM), with LiOH.H$_2$O (0.018 g, 0.439 mM) according to general procedure D (as described herein above). Yield: 0.024 g, 0.057 mM, 65.3%; $^1$H NMR (DMSO-d$_6$, 300 MHz) δ: 12.03 (s, 1H), 7.36-7.45 (m, 2H), 7.20-7.35 (m, 5H), 7.05 (d, J=8.4 Hz, 2H), 6.79 (d, J=8.7 Hz, 2H), 4.91 (s, 2H), 2.45-2.50 (m, 2H), 2.16 (t, J=7.2 Hz, 2H), 1.65-1.80 (m, 2H), 1.38 (s, 3H), 0.85-0.90 (m, 2H), 0.70-0.80 (m, 2H); MS m/z 419.2 [M+H$^+$].

Example 4

4-(4-((4'-(1-Cyanocyclopropyl)-4-fluoro-[1,1'-biphenyl]-2-yl)methoxy)phenyl)butanoic acid Step 4a

Synthesis of methyl 4-(4-((4'-(1-cyanocyclopropyl)-4-fluoro-[1,1'-biphenyl]-2-yl)methoxy)phenyl)butanoate The title compound was prepared in an analogous manner as Example 1 involving the reaction of 1-(4-bromophenyl)cyclopropanecarbonitrile (0.045 g, 0.202 mM) with methyl 4-(4-((5-fluoro-2-(4,4,5,5-tetramethyl-1,3,2-dioxaborolan-2-yl)benzyl)oxy)phenyl)butanoate (compound obtained in step 1b of Example 1) (0.130 g, 0.304 mM) and potassium carbonate (0.084 g, 0.607 mM) in the presence of tetrakis(triphenylphosphine)palladium(0) (0.012 g, 10.12 μmol), according to general procedure C (as described herein above). Yield: 0.078 g, 0.176 mM, 87%; $^1$H NMR (CDCl$_3$, 300 MHz) δ 7.30-7.40 (m, 5H), 7.10-7.30 (m, 2H), 7.06 (d, J=8.4 Hz, 2H), 6.77 (d, J=8.1 Hz, 2H), 4.86 (s, 2H), 3.66 (s, 3H), 2.58 (t, J=7.5 Hz, 2H), 2.31 (t, J=7.5 Hz, 2H), 1.80-2.00 (m, 2H), 1.60-1.85 (m, 2H), 1.40-1.50 (m, 2H); MS (m/z) 466.3 [M+Na$^+$].

Step 4b

Synthesis of 4-(4-((4'-(1-cyanocyclopropyl)-4-fluoro-[1,1'-biphenyl]-2-yl)methoxy)phenyl)butanoic acid The title compound was prepared in an analogous manner as Example 1 involving the reaction of methyl 4-(4-((4'-(1-cyanocyclopropyl)-4-fluoro-[1,1'-biphenyl]-2-yl)methoxy)phenyl)butanoate (0.068 g, 0.153 mM) with LiOH.H$_2$O (0.032 g, 0.767 mM) in water (2 mL/mM), according to general procedure D (as described herein above). Yield: 0.055 g, 0.128 mM, 84%; $^1$H NMR (DMSO-d$_6$, 300 MHz) δ 12.03 (s, 1H), 7.20-7.50 (m, 7H), 7.05 (d, J=8.1 Hz, 2H), 6.78 (d, J=8.1 Hz, 2H), 4.90 (s, 2H), 2.40-2.50 (m, 2H), 2.16 (t, J=7.2 Hz, 2H), 1.65-1.80 (m, 4H), 1.45-1.55 (m, 2H); MS (m/z) 452.4 [M+Na$^+$].

Example 5

3-(4-((4'-(1-Cyanocyclopropyl)-4-fluoro-[1,1'-biphenyl]-2-yl)methoxy)phenyl)propanoic acid Step 5a

Synthesis of ethyl 3-(4-((4'-(1-cyanocyclopropyl)-4-fluoro-[1,1'-biphenyl]-2-yl)methoxy)phenyl)propanoate The title compound was prepared in an analogous manner as Example 1 involving the reaction of 1-(4-bromophenyl)cyclopropane carbonitrile (0.052 g, 0.233 mM) with ethyl 3-(4-((5-fluoro-2-(4,4,5,5-tetramethyl-1,3,2-dioxaborolan-2-yl)benzyl)oxy)phenyl)propanoate (0.150 g, 0.350 mM) in presence of K$_2$CO$_3$ (0.097 g, 0.700 mM) and Pd(PPh$_3$)$_4$ (0.013 g, 0.012 mM), according to general procedure C (as described herein above). Yield: 0.088 g, 0.198 mM, 85%; $^1$H NMR (CDCl$_3$, 300 MHz) δ 7.30-7.40 (m, 5H), 7.22-7.30 (m, 1H), 7.05-7.15 (m, 3H), 6.79 (d, J=8.7 Hz, 2H), 4.87 (s, 2H), 4.13 (q, J=6.9 Hz, 2H), 2.89 (t, J=7.5 Hz, 2H), 2.58 (t, J=8.1 Hz, 2H), 1.75-1.85 (m, 2H), 1.40-1.50 (m, 2H) 1.24 (t, J=7.2 Hz, 3H); MS m/z 466.3 [M+Na$^+$].

Step 5b

Synthesis of 3-(4-((4'-(1-cyanocyclopropyl)-4-fluoro-[1,1'-biphenyl]-2-yl)methoxy)phenyl)propanoic acid The title compound was prepared in an analogous manner as Example 2 involving the reaction of ethyl 3-(4-((4'-(1-cyanocyclopropyl)-4-fluoro-[1,1'-biphenyl]-2-yl)methoxy)phenyl)propanoate (0.078 g, 0.176 mM) with LiOH.H$_2$O (0.879 mM) in water (2 mL/mM), according to general procedure D (as described herein above). Yield: 0.060 g, 0.144 mM, 82%; $^1$H NMR (DMSO-d$_6$, 300 MHz) δ 12.08 (s, 1H), 7.20-7.50 (m, 7H), 7.10 (d, J=8.1 Hz, 2H), 6.78 (d, J=8.1 Hz, 2H), 4.90 (s, 2H), 2.72 (t, J=7.5 Hz, 2H), 2.40-2.50 (m, 2H), 1.70-1.85 (m, 2H), 1.50-1.60 (m, 2H); MS m/z 438.2 [M+Na$^+$].

Example 6

3-(4-((2-(6-(1-Cyanocyclopropyl)pyridin-3-yl)-5-fluorobenzyl)oxy)phenyl)propanoic acid Step 6a

Synthesis of ethyl 3-(4-((2-(6-(1-cyanocyclopropyl)pyridin-3-yl)-5-fluorobenzyl)oxy)phenyl)propanoate The title compound was prepared in an analogous manner as Example 2 involving the reaction of ethyl 3-(4-((5-fluoro-2-(4,4,5,5-tetramethyl-1,3,2-dioxaborolan-2-yl)benzyl)oxy)phenyl)propanoate (0.150 g, 0.350 mM) with 1-(5-bromopyridin-2-yl)cyclopropanecarbonitrile (0.052 g, 0.233 mM), in the presence of K$_2$CO$_3$ (0.097 g, 0.700 mM) and tetrakis(triphenyl)phosphine)palladium(0) (0.013 g, 0.012 mM), according to general procedure C (as described herein above). Yield: 0.066 g, 0.145 mM, 62.2%. $^1$H NMR (CDCl$_3$, 300 MHz) δ 8.34 (s, 1H), 7.65-7.75 (m, 2H), 7.37 (dd, J=9.6 Hz, 1H), 7.20-7.30 (m, 1H), 7.05-7.18 (m, 3H), 6.76 (d, J=8.7 Hz, 2H), 4.83 (s, 2H), 4.12 (q, J=7.2 Hz, 2H), 2.88 (t, J=7.5 Hz, 2H), 2.58 (t, J=8.1 Hz, 2H), 1.82-1.90 (m, 2H), 1.70-1.80 (m, 2H), 1.23 (t, J=7.2 Hz, 3H); MS m/z 445.3 [M+H$^+$].

Step 6b

Synthesis of 3-(4-((2-(6-(1-cyanocyclopropyl)pyridin-3-yl)-5-fluorobenzyl)oxy)phenyl)propanoic acid The title compound was prepared in an analogous manner as Example 2 involving the reaction of ethyl 3-(4-((2-(6-(1-cyanocyclopropyl)pyridin-3-yl)-5-fluorobenzyl)oxy)phenyl)propanoate (0.060 g, 0.135 mM) with LiOH.H$_2$O (5.67 mg, 0.135 mM) in water (2 mL/mM), according to general procedure D (as described herein above). Yield: 0.045 g, 0.108 mM, 80%; $^1$H NMR (DMSO-d$_6$, 300 MHz) δ 12.06 (s, 1H), 8.51 (s, 1H), 7.87 (dd, J=8.1 Hz, 1H), 7.55 (d, J=8.1 Hz, 1H), 7.25-7.50 (m, 3H), 7.09 (d, J=8.7 Hz, 2H), 6.76 (d, J=8.4 Hz, 2H), 4.91 (s, 2H), 2.71 (t, J=7.5 Hz, 2H), 2.35-2.60 (m, 2H), 1.75-1.90 (m, 2H), 1.65-1.70 (m, 2H); MS (m/z) 417.2 [M+H$^+$].

Example 7

4-(4-((4'-Cyclopropyl-4-fluoro-[1,1'-biphenyl]-2-yl)methoxy)phenyl)butanoic acid Step 7a Synthesis of methyl 4-(4-((4'-cyclopropyl-4-fluoro-[1,1'-biphenyl]-2-yl)methoxy)phenyl)butanoate The title compound was prepared in an analogous manner as Example 1 involving the reaction of 1-bromo-4-cyclopropylbenzene (0.032 g, 0.163 mM) with methyl-4-(4-((5-fluoro-2-(4,4,5,5-tetramethyl-1,3,2-dioxaborolan-2-yl)benzyl)oxy)phenyl)butanoate (0.07 g, 0.163 mM) and potassium carbonate (0.068 g, 0.49 mM) in the presence of tetrakis(triphenyl)phosphine palladium(0) (0.003 g, 0.008 mM), according to general procedure C (as described herein above). Yield: 0.035 g, 0.084 mM, 51%; $^1$H NMR (CDCl$_3$, 300 MHz) δ 7.32-7.35 (m, 2H), 7.21-7.24 (m, 2H), 7.04-7.12 (m, 5H), 6.77 (d, J=8.4 Hz, 2H) 4.90 (s, 2H), 3.66 (s, 3H), 2.50 (t, J=7.2 Hz, 2H), 2.31 (t, J=7.2 Hz 2H), 1.88-1.93 (m, 3H), 0.99-1.02 (m, 2H), 0.73-0.75 (m, 2H) LC-MS (m/z) 419.3 [M+H$^+$].

Step 7b

Synthesis of 4-(4-((4'-cyclopropyl-4-fluoro-[1,1'-biphenyl]-2-yl)methoxy)phenyl)butanoic acid The title compound was prepared in an analogous manner as Example 1 involving the reaction of methyl 4-(4-((4'-cyclopropyl-4-fluoro-[1,1'-biphenyl]-2-yl)methoxy)phenyl)butanoate (0.03 g, 0.071 mM) with LiOH.H$_2$O (0.015 g, 0.356 mM), general procedure D (as described herein above). Yield: 0.022 g, 0.054 mM, 76%; $^1$H NMR (DMSO d$_6$, 300 MHz) δ 12.03 (s, 1H), 7.31-7.40 (m, 2H), 7.26 (d, J=8.4 Hz, 3H), 7.04-7.12 (m, 4H), 6.79 (d, J=8.4 Hz, 2H) 4.89 (s, 2H), 2.52 (m, 2H), 2.17 (t, J=7.5 Hz, 2H), 1.93 (m, 1H), 1.70-1.75 (m, 2H), 0.93-0.94 (m, 2H), 0.67-0.69 (m, 2H); MS (m/z) 427.2 [M+Na$^+$].

Example 8

4-(4-((2-(2,3-Dihydro-1H-inden-5-yl)-5-fluorobenzyl)oxy)phenyl)butanoic acid Step 8a Synthesis of methyl 4-(4-((2-(2,3-dihydro-1H-inden-5-yl)-5-fluorobenzyl)oxy)phenyl)butanoate The title compound was prepared in an analogous manner as Example 1 involving the reaction of 5-bromo-2,3-dihydro-1H-indene (0.053 g, 0.269 mM) with methyl-4-(4-((5-fluoro-2-(4,4,5,5-tetramethyl-1,3,2-dioxaborolan-2-yl)benzyl)oxy)phenyl)butanoate (0.150 g, 0.350 mM) and potassium carbonate (0.112 g, 0.808 mM) in the presence of tetrakis(triphenyl)phosphine)palladium(0) (0.016 g, 0.013 mM), according to general procedure C (as described herein above). Yield: 0.098 g, 0.234 mM, 87%; $^1$H NMR (CDCl$_3$, 300 MHz) δ 7.32-7.38 (m, 1H), 7.28-7.31 (m, 1H), 7.18-7.28 (m, 2H), 7.00-7.12 (m, 4H), 6.78 (d, J=8.7 Hz, 2H), 4.92 (s, 2H), 3.66 (s, 3H), 2.93 (q, J=7.5 Hz, 4H), 2.57 (t, J=7.5 Hz, 2H), 2.31 (t, J=7.5 Hz, 2H), 2.05-2.20 (m, 2H), 1.80-2.00 (m, 2H); MS (m/z) 441.1 [M+Na$^+$].

Step 8b

Synthesis of 4-(4-((2-(2,3-dihydro-1H-inden-5-yl)-5-fluorobenzyl)oxy)phenyl)butanoic acid The title compound was prepared in an analogous manner as Example 1 involving the reaction of methyl 4-(4-((2-(2,3-dihydro-1H-inden-5-yl)-5-fluorobenzyl)oxy)phenyl)butanoate (0.080 g, 0.191 mM) with LiOH.H$_2$O (0.040 g, 0.956 mM), general procedure D (as described herein above). Yield: 0.050 g, 0.124 mM, 64.7%; $^1$H NMR (DMSO-d$_6$, 300 MHz) δ 12.03 (s, 1H), 7.30-7.50 (m, 2H), 7.18-7.28 (m, 3H), 7.12 (d, J=7.8 Hz, 1H), 7.05 (d, J=8.4 Hz, 2H), 6.79 (d, J=8.7 Hz, 2H), 4.89 (s, 2H), 2.75-2.85 (m, 4H), 2.40-2.50 (m, 2H), 2.16 (t, J=7.5 Hz, 2H), 1.95-2.05 (m, 2H), 1.65-1.85 (m, 2H); MS (m/z) 427.4 [M+Na$^+$].

Example 9

4-(4-((5-Fluoro-2-(5,6,7,8-tetrahydronaphthalen-2-yl)benzyl)oxy)phenyl)butanoic acid Step 9a Synthesis of methyl 4-(4-((5-fluoro-2-(5,6,7,8-tetrahydronaphthalen-2-yl)benzyl)oxy)phenyl)butanoate The title compound was prepared in an analogous manner as Example 1 involving the reaction of methyl 4-(4-((2-bromo-5-fluorobenzyl)oxy)phenyl)butanoate (0.50 g, 1.312 mM) with (5,6,7,8-tetrahydronaphthalen-2-yl)boronic acid (0.346 g, 1.967 mM) in presence of Tetrakis(triphenylphosphine)palladium(0) (0.076 g, 0.066 mM), according to general procedure C (as described herein above) Yield: 0.528 g, 1.221 mM, 93%; $^1$H NMR (CDCl$_3$, 300 MHz) δ 7.30-7.38 (m, 1H), 7.20-7.30 (m, 1H), 6.95-7.15 (m, 6H), 6.79 (d, J=8.7 Hz, 2H), 4.92 (s, 2H), 3.66 (s, 3H), 2.69-2.85 (m, 4H), 2.58 (t, J=7.5 Hz, 2H), 2.31 (t, J=7.5 Hz, 2H), 1.85-2.00 (m, 2H), 1.75-1.85 (m, 4H); MS m/z 455.1 [M+Na$^+$].

Step 9b

Synthesis of 4-(4-((5-fluoro-2-(5,6,7,8-tetrahydronaphthalen-2-yl)benzyl)oxy)phenyl)butanoic acid The title compound was prepared in an analogous manner as Example 1 involving the reaction of methyl 4-(4-((5-fluoro-2-(5,6,7,8-tetrahydronaphthalen-2-yl)benzyl)oxy)phenyl)butanoate (0.50 g, 1.156 mM) with LiOH.H$_2$O (0.243 g, 5.78 mM), according to general procedure D (as described herein above). Yield: 0.428 g, 1.023 mM, 88%; $^1$H NMR (DMSO-d$_6$, 300 MHz) δ 12.03 (s, 1H), 7.15-7.45 (m, 3H), 7.00-7.15 (m, 5H), 6.80 (d, J=8.4 Hz, 2H), 4.88 (s, 2H), 2.60-2.75 (m, 4H), 2.40-2.50 (m, 2H), 2.16 (t, J=7.2 Hz, 2H), 1.60-1.80 (m, 6H); MS (m/z) 441.1 [M+Na$^+$].

Example 10

4-(4-((2-(Bicyclo[4.2.0]octa-1(6),2,4-trien-3-yl)-5-fluorobenzyl)oxy)phenyl)butanoic acid Step 10a Synthesis of methyl 4-(4-((2-(bicyclo[4.2.0]octa-1(6),2,4-trien-3-yl)-5-fluorobenzyl)oxy)phenyl)butanoate The title compound was prepared in an analogous manner as Example 1 involving the reaction of bicyclo[4.2.0]octa- 1(6),2,4-trien-3-ylboronic acid (0.04 g, 0.275 mM) with methyl 4-(4-((2-bromo-5-fluorobenzyl)oxy)phenyl)butanoate (0.04 g, 0.184 mM) and potassium carbonate (0.076 g, 0.551 mM) in the presence of tetrakis(triphenylphosphine)palladium(0) (0.003 g, 0.009 mM), according to general procedure C (as described herein above). Yield: 0.068 g, 0.168 mM, 92%; $^1$H NMR (CDCl$_3$, 300 MHz) δ 7.36 (d, J=9.9 Hz, 1H), 7.01-7.251 (m, 7H), 6.78 (d, J=8.7 Hz, 2H), 4.90 (s, 2H), 3.66 (s, 3H), 3.22 (s, 4H), 2.56 (t, J=7.5 Hz, 2H), 2.28-2.31 (m, 2H), 1.93-1.96 (m, 2H); MS (m/z) 427.2 [M+Na$^+$].

Step 10b

Synthesis of 4-(4-((2-(bicyclo[4.2.0]octa-1(6),2,4-trien-3-yl)-5-fluorobenzyl)oxy)phenyl)butanoic acid The title compound was prepared in an analogous manner as Example 1 involving the reaction of methyl 4-(4-((2-(bicyclo[4.2.0]octa-1(6),2,4-trien-3-yl)-5-fluorobenzyl)oxy)phenyl)butanoate (0.06 g, 0.148 mM) with LiOH.H$_2$O (0.031 g, 0.956 mM), according to general procedure D (as described herein above). Yield: 0.040 g, 0.102 mM, 69.1%; $^1$H NMR (CDCl$_3$, 300 MHz) δ 7.35 (dd J=2.7, 9.9 Hz, 1H), 7.22-7.26 (m, 2H), 7.01-7.14 (m, 5H), 6.78 (d, J=8.4 Hz, 2H), 4.90 (s, 2H), 3.21 (s, 4H), 2.60 (t, J=7.5 Hz, 2H), 2.32-2.37 (m, 2H), 1.87-1.97 (m, 2H); MS (m/z) 413.2 [M+Na$^+$].

Example 11

4-(4-((2-(5-Cyclopropylthiophen-2-yl)-5-fluorobenzyl)oxy)phenyl)butanoic acid

Step 11a

Synthesis of methyl 4-(4-((2-(5-cyclopropylthiophen-2-yl)-5-fluorobenzyl)oxy)phenyl)butanoate The title compound was prepared in an analogous manner as Example 1 involving the reaction of methyl 4-(4-((5-fluoro-2-(4,4,5,5-tetramethyl-1,3,2-dioxaborolan-2-yl)benzyl)oxy)phenyl)butanoate (100 mg, 0.233 mM) with 2-bromo-5-cyclopropylthiophene (61.6 mg, 0.304 mM) and potassium carbonate (81 mg, 0.584 mM) in the presence of (tetrakistriphenylphosphine)palladium(0) (16.19 mg, 0.014 mM), according to general procedure C (as described herein above). Yield: 82.3 mg, 83%; $^1$H NMR (500 MHz, CDCl$_3$) δ: 7.42-7.39 (m, 1H), 7.35-7.34 (m, 1H), 7.09 (d, J=8.5 Hz, 2H), 7.06-7.03 (m, 1H), 6.86-6.84 (m, 3H), 6.73-6.72 (m, 1H), 5.05 (s, 2H), 3.68 (s, 3H), 2.60 (t, J=7.5 Hz, 2H), 2.33 (t, J=7.5 Hz, 2H), 2.15-2.02 (m, 1H), 1.97-1.91 (m, 2H), 1.02 (dd, J=7.00 Hz, 2H), 0.68 (dd, J=6.00 Hz, 2H); MS (E/Z): 425.1 (M+H), 447.1 (M+Na).

Step 11b

Synthesis of 4-(4-((2-(5-cyclopropylthiophen-2-yl)-5-fluorobenzyl)oxy)phenyl)butanoic acid The title compound was prepared in an analogous manner as Example 1 involving the reaction of methyl 4-(4-((2-(5-cyclopropylthiophen-2-yl)-5-fluorobenzyl)oxy)phenyl)butanoate (75 mg, 0.177 mM) with LiOH.H$_2$O (589 µl, 0.883 mM), according to general procedure D (as described herein above). Yield: 64.2 mg, 0.156 mM, 89%; $^1$H NMR (500 MHz, DMSO-d$_6$) δ: 12.04 (bs, 1H), 7.49-7.43 (m, 2H), 7.27-7.24 (m, 1H), 7.10 (d, J=8.0 Hz, 2H), 6.97 (d, J=3.5 Hz, 1H), 6.88 (d, J=8.5 Hz, 2H), 6.80 (d, J=3.0 Hz, 1H), 5.02 (s, 2H), 2.53-2.50 (m, 2H), 2.19 (t, J=7.0 Hz, 2H), 2.12-2.10 (m, 1H), 1.77-1.74 (m, 1H), 0.98 (dd, J=6.5 Hz, 2H), 0.66 (dd, J=7.0 Hz, 2H); MS (E/Z): 433.2 (M+Na).

Example 12

4-(4-((5-Fluoro-2-(5-(1-hydroxycyclobutyl)thiophen-2-yl)benzyl)oxy)phenyl)butanoic acid Step 12a Synthesis of 1-(5-bromothiophen-2-yl)cyclobutanol To a stirred solution of 2,5-dibromothiophene (949 mg, 3.92 mM) dissolved in dry THF at −78° C., n-butyllithium was added (2943 µl, 4.71 mM). The mixture was allowed to stir for 30 min and then cyclobutanone (550 mg, 7.85 mM) was slowly added for 2 min. After completion of reaction, the reaction mixture was quenched with ammonium chloride, extracted with ethyl acetate, dried over sodium sulphate and purified by column chromatography to give 1-(5-bromothiophen-2-yl)cyclobutanol. $^1$H NMR (300 MHz, CDCl$_3$) δ: 6.91 (d, J=3.9 Hz, 1H), 6.81 (d, J=3.9 Hz, 1H), 2.54-2.36 (m, 4H), 2.28 (bs, 1H), 2.01-1.88 (m, 1H), 1.80-1.65 (m, 1H), HPLC: 99.46%; MS (E/Z): 256.3 (M+Na).

Step 12b

Synthesis of methyl 4-(4-((5-fluoro-2-(5-(1-hydroxycyclobutyl)thiophen-2-yl)benzyl)oxy)phenyl)butanoate The title compound was prepared in an analogous manner as Example 1 involving the reaction of 1-(5-bromothiophen-2-yl)cyclobutanol (56.6 mg, 0.243 mM) with methyl-4-(4-((5-fluoro-2-(4,4,5,5-tetramethyl-1,3,2-dioxaborolan-2-yl)benzyl)oxy)phenyl)butanoate (compound obtained in step 1b of Example 1) (80 mg, 0.187 mM), potassium carbonate (64.5 mg, 0.467 mM), in the presence of tetrakis(triphenyl)phosphine)palladium(0) (12.95 mg, 0.011 mM) according to general procedure C (as described herein above). Yield: 63.7 mg, 0.119 mM, 63.8%; $^1$H NMR (500 MHz, CDCl$_3$) δ: 7.46-7.41 (m, 1H), 7.37-7.11 (m, 1H), 7.91 (d, J=8.7 Hz, 2H), 7.15 (d, J=3.6 Hz, 2H), 7.92 (d, J=3.6 Hz, 2H), 7.84 (d, J=8.7 Hz, 2H), 5.05 (s, 2H), 3.67 (s, 3H), 2.68-2.53 (m, 4H), 2.52-2.47 (m, 2H), 2.35-2.30 (m, 2H), 1.97-1.87 (m, 3H), 1.82-1.73 (m, 1H); MS (E/Z): 477.1 (M+Na).

Step 12c

Synthesis of 4-(4-((5-fluoro-2-(5-(1-hydroxycyclobutyl)thiophen-2-yl)benzyl)oxy)phenyl)butanoic acid The title compound was prepared in an analogous manner as Example 1 involving the reaction of methyl 4-(4-((5-fluoro-2-(5-(1-hydroxycyclobutyl)thiophen-2-yl)benzyl)oxy)phenyl)butanoate (82 mg, 0.180 mM) with LiOH.H$_2$O (37.8 mg, 0.902 mM) according to general procedure D (as described herein above). Yield: 67.8 mg, 0.153 mM, 85%; $^1$H NMR (300 MHz, DMSO-d$_6$) δ: 12.04 (bs, 1H), 7.58-7.43 (m, 2H), 7.30-7.24 (m, 1H), 7.10 (d, J=8.4 Hz, 2H), 7.03 (s, 2H), 7.87 (d, J=8.4 Hz, 2H), 7.92 (d, J=3.6 Hz, 2H), 7.84 (d, J=8.7 Hz, 2H), 5.96 (bs, 2H), 5.04 (s, 2H), 2.55-2.47 (m, 4H), 2.34-2.25 (m, 2H), 2.18 (t, J=7.5 Hz, 2H), 1.79-1.61 (m, 4H); MS (E/Z): 463.2 (M+Na).

Example 13

3-(4-((4-Fluoro-4'-(oxetan-3-yl)-[1,1'-biphenyl]-2-yl)methoxy)phenyl)propanoic acid Step 13a

Synthesis of 3-(4-bromophenyl)oxetane

To a solution of (4-bromophenyl)boronic acid (250 mg, 1.245 mM), trans-2-aminocyclohexanol hydrochloride (6.91 mg, 0.06 mM) and sodium hexamethyldisilazane (1.867 ml, 1.867 mM) was added nickel(II) iodide (18.75 mg, 0.06 mM) and the mixture was degassed with argon for 2-5 min. To the resulting solution isopropyl alcohol (2 ml) was added and the mixture was stirred under argon for 5-10 min and then 3-iodooxetane (183 mg, 0.996 mM) was added. The mixture was then allowed heat at 80° C. under microwave irradiation for 20-30 min. After completion of reaction, the mixture was quenched by adding saturated ammonium chloride, extracted with ethyl acetate, dried over sodium sulphate, concentrated and purified by column chromatography to get 3-(4-bromophenyl)oxetane. Yield: 80 mg, 0.320 mM, 25.7%; $^1$H NMR (300 MHz, DMSO-$d_6$): δ 7.52 (d, J=8.4 Hz, 2H), 7.31 (d, J=8.4 Hz, 2H), 5.15 (d, J=5.1 Hz, 2H), 5.15-5.07 (m, 2H), 4.84-4.81 (m, 1H)

Step 13b

Synthesis of ethyl 3-(4-((4-fluoro-4'-(oxetan-3-yl)-[1,1'-biphenyl]-2-yl)methoxy)phenyl)propanoate The title compound was prepared in an analogous manner as step-2c of Example 2 involving the reaction of ethyl 3-(4-((5-fluoro-2-(4,4,5,5-tetramethyl-1,3,2-dioxaborolan-2-yl)benzyl)oxy)phenyl)propanoate (120 mg, 0.279 mM) with 3-(4-bromophenyl)oxetane (71.3 mg, 0.334 mM), according to general procedure C (as described herein above). Yield: 77 mg, 0.175 mM, 62.7%; $^1$H NMR (300 MHz, CDCl$_3$) δ: 7.46-7.34 (m, 6H), 7.30-7.24 (m, 1H), 7.93 (d, J=8.4 Hz, 2H), 6.81 (d, J=8.7 Hz, 2H), 4.96-4.92 (m, 4H), 4.63 (d, J=6.3 Hz, 2H), 4.31-4.26 (m, 1H), 4.01 (q, J=7.2 Hz, 2H), 2.75 (t, J=7.5 Hz, 2H), 2.53 (t, J=7.5 Hz, 2H), 1.08 (t, J=6.3 Hz, 3H); MS (E/Z): 457.2 (M+Na).

Step 13c

Synthesis of 3-(4-((4-fluoro-4'-(oxetan-3-yl)-[1,1'-biphenyl]-2-yl)methoxy)phenyl)propanoic acid The title compound was prepared in an analogous manner as Example 2 involving the reaction of ethyl 3-(4-((4-fluoro-4'-(oxetan-3-yl)-[1,1'-biphenyl]-2-yl)methoxy)phenyl)propanoate (45 mg, 0.104 mM) with LiOH.H$_2$O (21.84 mg, 0.518 mM), according to general procedure D (as described herein above). Yield: 39.8 mg, 0.090 mM, 87.3%; $^1$H NMR (300 MHz, DMSO-$d_6$) δ: 12.07 (bs, 1H), 7.43-7.34 (m, 6H), 7.30-7.24 (m, 1H), 7.97 (d, J=8.7 Hz, 2H), 6.78 (d, J=8.7 Hz, 2H), 4.96-4.92 (m, 4H), 4.64 (d, J=6.3 Hz, 2H), 4.33-4.26 (m, 1H), 2.72 (t, J=7.8 Hz, 2H), 2.46 (t, J=7.5 Hz, 2H); MS (E/Z): 407.1 (M+H), 405.0 (M−H).

Example 14

3-(4-((4-Fluoro-4'-(1-hydroxycyclobutyl)-[1,1'-biphenyl]-2-yl)methoxy)phenyl)propanoic acid Step 14a

Synthesis of 1-(4-bromophenyl)cyclobutanol

The title compound was prepared in an analogous manner as step-15a of Example 15 involving the reaction of 1,4-dibromobenzene (1.683 g, 7.13 mM) with cyclobutanone (1 g, 14.27 mM). Yield: 2.74 g, 12.06 mM, 84.5%; $^1$H NMR (300 MHz, CDCl$_3$) δ: 7.51 (d, J=8.4 Hz, 2H), 7.33 (d, J=8.4 Hz, 1H), 5.55 (bs, 1H), 2.38-2.20 (m, 4H), 1.98-1.85 (m, 1H), 1.70-1.58 (m, 1H); MS (E/Z): 226.2 (M−1).

Step 14b

Synthesis of ethyl 3-(4-((4-fluoro-4'-(1-hydroxycyclobutyl)-[1,1'-biphenyl]-2-yl)methoxy)phenyl)propanoate The title compound was prepared in an analogous manner as step-2c of Example 2 involving the reaction of ethyl 3-(4-((5-fluoro-2-(4,4,5,5-tetramethyl-1,3,2-dioxaborolan-2-yl)benzyl)oxy)phenyl)propanoate (165 mg, 0.385 mM) with 1-(4-bromophenyl)cyclobutanol (105 mg, 0.462 mM), according to general procedure C (as described herein above). Yield: 120 mg, 0.265 mM, 68.7%; $^1$H NMR (300 MHz, CDCl$_3$) δ: 7.56 (d, J=8.4 Hz, 2H), 7.36 (d, J=8.4 Hz, 2H), 7.30-7.27 (m, 1H), 7.11-7.05 (m, 4H), 6.79 (d, J=8.4 Hz, 2H), 4.92 (s, 2H), 4.13 (q, J=7.2 Hz, 2H), 2.89 (t, J=7.8 Hz, 2H), 2.67-2.55 (m, 4H), 2.46-2.37 (m, 2H), 2.12-2.00 (m, 3H), 1.26 (t, J=6.3 Hz, 3H); MS (E/Z): 471.3 (M+Na).

Step 14c

Synthesis of 3-(4-((4-fluoro-4'-(1-hydroxycyclobutyl)-[1,1'-biphenyl]-2-yl)methoxy)phenyl)propanoic acid The title compound was prepared in an analogous manner as Example 2 involving the reaction of ethyl 3-(4-((4-fluoro-4'-(1-hydroxycyclobutyl)-[1,1'-biphenyl]-2-yl)methoxy)phenyl)propanoate (60 mg, 0.134 mM) with LiOH.H$_2$O (28.14 mg, 0.669 mM) according to general procedure D (as described herein above). Yield: 50.9 mg, 0.112 mM, 83.8%; $^1$H NMR (300 MHz, DMSO-$d_6$) δ: 12.07 (bs, 1H), 7.53 (d, J=8.1 Hz, 2H), 7.41-7.35 (m, 4H), 7.29-7.27 (m, 1H), 7.10 (d, J=8.1 Hz, 2H), 6.78 (d, J=8.4 Hz, 2H), 5.52 (bs, 1H), 4.92 (s, 2H), 2.72 (t, J=7.5 Hz, 2H), 2.49-2.36 (m, 4H), 2.31-2.22 (m, 2H), 2.12-2.00 (m, 2H); MS (E/Z): 421.3 (M+H).

Example 15

3-(4-((4'-(5,5-Dimethylcyclopent-1-en-1-yl)-4-fluoro-[1,1'-biphenyl]-2-yl)methoxy)phenyl)propanoic acid Step 15a

Synthesis of 1-(4-bromophenyl)-2,2-dimethylcyclopentanol

The title compound was prepared in an analogous manner as step-15a of Example 15 involving the reaction of 1,4-dibromobenzene (1577 mg, 6.69 mM) with 2,2-dimethylcyclopentanone (500 mg, 4.46 mM). Yield: 1077 mg, 4.00 mM, 89.8%; $^1$H NMR (300 MHz, CDCl$_3$) δ: 7.49-7.39 (m, 4H), 4.37 (bs, 1H), 2.60-2.54 (m, 1H), 1.89-1.70 (m, 4H), 1.49-1.43 (m, 1H), 0.84 (s, 3H), 0.53 (s, 3H); MS (E/Z): 270.1 (M+1).

Step 15b

Synthesis of ethyl 3-(4-((4-fluoro-4'-(1-hydroxy-2,2-dimethylcyclopentyl)-[1,1'-biphenyl]-2-yl)methoxy)phenyl)propanoate The title compound was prepared in an analogous manner as step-2c of Example 2 involving the reaction of ethyl 3-(4-((5-fluoro-2-(4,4,5,5-tetramethyl-1,3,2-dioxaborolan-2-yl)benzyl)oxy)phenyl)propanoate (159 mg, 0.372 mM) with 1-(4-bromophenyl)-2,2-dimethylcyclopentanol (100 mg, 0.372 mM), according to general procedure C (as described herein above). Yield: 125 mg, 0.237 mM, 63.8%; $^1$H NMR (300 MHz, CDCl$_3$) δ: 7.31 (d, J=4.2 Hz, 2H), 7.30-7.27 (m, 3H), 7.10-7.04 (m, 4H), 6.77 (d, J=8.4 Hz, 2H), 4.92 (s, 2H), 4.13 (q, J=6.9 Hz, 2H), 2.91-2.84 (m, 2H), 2.60-2.53 (m, 2H), 2.00-2.81 (m, 4H), 1.68-1.59 (m, 2H), 1.24 (t, J=7.2 Hz, 3H), 1.03 (s, 3H), 0.68 (s, 3H); MS (E/Z): 513.2 (M+Na).

Step 15c

Synthesis of ethyl 3-(4-((4'-(5,5-dimethylcyclopent-1-en-1-yl)-4-fluoro-[1,1'-biphenyl]-2-yl)methoxy)phenyl)propanoate To a stirred solution of ethyl-3-(4-((4-fluoro-4'-(1-hydroxy-2,2-dimethylcyclopentyl)-[1,1'-biphenyl]-2-yl)methoxy)phenyl)propanoate (95 mg, 0.194 mM) dissolved in Toluene (5 ml), 4-methylbenzenesulfonic acid (33.3 mg, 0.194 mM) was added and the mixture was allowed to reflux at 110° C. for 30 min. After completion of reaction, the mixture was quenched with water and extracted with ethyl acetate and purified by column chromatography. Yield: 70.0 mg, 0.139 mM, 72%; $^1$H NMR (300 MHz, CDCl$_3$) δ: 7.40 (d, J=8.4 Hz, 2H), 7.330-7.26 (m, 3H), 7.10-7.06 (m, 4H), 6.80-6.76 (m, 2H), 5.84 (t, J=7.5 Hz, 1H), 4.94 (s, 2H), 4.13 (q, J=6.9 Hz, 2H), 2.88 (t, J=7.5 Hz, 2H), 2.58 (t, J=7.5 Hz, 2H), 2.43-2.38 (m, 3H), 1.89 (t, J=6.9 Hz, 2H), 1.58 (s, 3H), 1.52 (t, J=6.9 Hz, 2H), 1.24 (s, 3H); MS (E/Z): 495.2 (M+Na).

Step 15d

Synthesis of 3-(4-((4'-(5,5-dimethylcyclopent-1-en-1-yl)-4-fluoro-[1,1'-biphenyl]-2-yl)methoxy)phenyl)propanoic acid The title compound was prepared in an analogous manner as Example 2 involving the reaction of ethyl 3-(4-((4'-(5,5-dimethylcyclopent-1-en-1-yl)-4-fluoro-[1,1'-biphenyl]-2-yl)methoxy)phenyl)propanoate (60 mg, 0.127 mM) with LiOH.H$_2$O (26.6 mg, 0.635 mM), according to general procedure D (as described herein above). Yield: 50.1 mg, 0.113 mM, 88.7%; $^1$H NMR (300 MHz, DMSO-d$_6$) δ: 12.07 (bs, 1H), 7.40 (d, J=8.4 Hz, 2H), 7.30-7.25 (m, 3H), 7.11-7.06 (m, 4H), 6.81-6.77 (m, 2H), 5.84 (t, J=7.5 Hz, 1H), 2.90 (t, J=7.5 Hz, 2H), 2.64 (t, J=7.5 Hz, 2H), 2.58 (t, J=7.5 Hz, 2H), 2.43-2.37 (m, 2H), 1.89 (t, J=6.9 Hz, 2H), 1.27 (s, 6H); MS (E/Z): 445.2 (M+1), 443.2 (M−1).

Example 16

4-(4-((4'-Cyclohexyl-4-fluoro-[1,1'-biphenyl]-2-yl)methoxy)phenyl)butanoic acid Step 16a

Synthesis of methyl 4-(4-((4'-cyclohexyl-4-fluoro-[1,1'-biphenyl]-2-yl)methoxy)phenyl)butanoate The title compound was prepared in an analogous manner as step-1c of Example 1 involving the reaction of (4-cyclohexylphenyl)boronic acid (92 mg, 0.449 mM) with methyl 4-(4-((2-bromo-5-fluorobenzyl)oxy)phenyl)butanoate (114 mg, 0.299 mM), and potassium carbonate (104 mg, 0.748 mM) in presence of tetrakis(triphenyl)phosphine palladium (0) (20.73 mg, 0.018 mM), according to general procedure C (as described herein above). Yield: 91.3 mg, 0.198 mM, 66.3%; $^1$H NMR (300 MHz, CDCl$_3$) δ: 7.36-7.31 (m, 2H), 7.29-7.25 (m, 4H), 7.11-7.04 (m, 3H), 7.78 (t, J=8.4 Hz, 2H), 4.92 (s, 2H), 3.66 (s, 3H), 2.58 (t, J=7.8 Hz, 4H), 2.31 (t, J=7.5 Hz, 2H), 1.96-1.88 (m, 6H), 1.48-1.34 (m, 3H); MS (E/Z): 483.3 (M+Na).

Step 16b

Synthesis of 4-(4-((4'-cyclohexyl-4-fluoro-[1,1'-biphenyl]-2-yl)methoxy)phenyl)butanoic acid The title compound was prepared in an analogous manner as Example 1 involving the reaction of methyl 4-(4-((4'-cyclohexyl-4-fluoro-[1,1'-biphenyl]-2-yl)methoxy)phenyl)butanoate (80 mg, 0.174 mM) with LiOH.H$_2$O (36.5 mg, 0.868 mM), according to general procedure D (as described herein above). Yield: (70 mg, 0.151 mM, 87%; $^1$H NMR (300 MHz, DMSO-d$_6$) δ: 12.04 (bs, 1H), 7.41-7.32 (m, 2H), 7.29-7.22 (m, 5H), 7.55 (t, J=8.4 Hz, 2H), 6.78 (t, J=8.4 Hz, 2H), 4.90 (s, 2H), 2.49-2.46 (m, 4H), 2.16 (t, J=7.2 Hz, 2H), 1.79-1.67 (m, 6H), 1.42-1.33 (m, 3H), 1.30-1.23 (m, 2H); MS (E/Z): 444.8 (M+1), 469.2 (M+Na).

Example 17

3-(4-((5-Fluoro-2-(6-(oxetan-3-yl)pyridin-3-yl)benzyl)oxy)phenyl)propanoic acid Step 17a

Synthesis of ethyl 3-(4-((5-fluoro-2-(pyridin-3-yl)benzyl)oxy)phenyl)propanoate The title compound was prepared in an analogous manner as step 2b of Example 2 involving the reaction of ethyl-3-(4-((2-bromo-5-fluorobenzyl)oxy)phenyl)propanoate (100 mg, 0.262 mM) with pyridin-3-ylboronic acid (64.5 mg, 0.525 mM), according to general procedure C (as described herein above). Yield: (64.1 mg, 0.167 mM, 63.8%); $^1$H NMR (300 MHz, DMSO-d$_6$) δ: 12.01 (bs, 1H), 8.62 (s, 1H), 7.80 (d, J=6.3 Hz, 2H), 7.45-7.32 (m, 3H), 6.92 (d, J=8.1 Hz, 2H), 6.78 (d, J=8.1 Hz, 2H), 4.92 (s, 1H), 4.89-4.69 (m, 4H), 4.42-4.38 (m, 1H), 2.72 (t, J=7.5 Hz, 2H), 2.46 (t, J=7.5 Hz, 2H); MS (E/Z): 408.2 (M+1).

Step 17b

Synthesis of ethyl 3-(4-((5-fluoro-2-(6-(oxetan-3-yl)pyridin-3-yl)benzyl)oxy)phenyl)propanoate The title compound was prepared according to the literature procedure (*J. Org. Chem.*, 74 (16), 2009, pp. 6354-6357) involving the reaction of ethyl-3-(4-((5-fluoro-2-(pyridin-3-yl)benzyl)oxy)phenyl)propanoate (200 mg, 0.527 mM), concentrated sulphuric acid (103 mg, 1.054 mM), 3-iodooxetane (145 mg, 0.791 mM) and iron (II) sulphate heptahydrate (68.9 mg, 0.158 mM) in DMSO (10 mL), hydrogen peroxide (23.31 mg, 0.685 mM) (30% in water) was added drop wise over 1-2 min at room temperature. After 1-2 min, further portion of iron (II) sulphate heptahydrate (0.3 mol) was added and the mixture was stirred for 30 min. Further iron (II) sulphate heptahydrate (0.3 mol) was added, and the mixture was stirred for 15 min. After completion of reaction, the mixture was poured into 0.2 m solution of sodium hydroxide and extracted with ethyl acetate, concentrated. The crude product was used as it is for further reaction without any purification.

Step 17c

Synthesis of 3-(4-((5-fluoro-2-(6-(oxetan-3-yl)pyridin-3-yl)benzyl)oxy)phenyl)propanoic acid The title compound was prepared in an analogous manner as Example 2 involving the reaction of ethyl 3-(4-((5-fluoro-2-(6-(oxetan-3-yl)pyridin-3-yl)benzyl)oxy)phenyl)propanoate (40 mg, 0.092 mM) with LiOH.H$_2$O (19.3 mg, 0.459 mM), according to general procedure D (as described herein above). Yield: 32.6 mg, 0.071 mM, 77.8%; $^1$H NMR (300 MHz, DMSO-d$_6$) δ: 12.01 (bs, 1H), 8.62 (s, 1H), 7.80 (d, J=6.3 Hz, 2H), 7.45-7.32 (m, 3H), 6.92 (d, J=8.1 Hz, 2H), 6.78 (d, J=8.1 Hz, 2H), 4.92 (s, 1H), 4.89-4.69 (m, 4H), 4.42-4.38 (m, 1H), 2.72 (t, J=7.5 Hz, 2H), 2.46 (t, J=7.5 Hz, 2H); MS (E/Z): 408.2 (M+1).

Example 18

3-(5-((4'-(1-Cyanocyclopropyl)-4-fluoro-[1,1'-biphenyl]-2-yl)methoxy)pyridin-2-yl)propanoic acid Step 18a

Synthesis of 5-((2-bromo-5-fluorobenzyl)oxy)picolinaldehyde

To a stirred solution of 2-(2-(bromomethyl)-4-fluorophenyl)-5-methylthiophene (0.200 g, 1.625 mM) and 5-hydroxypicolinaldehyde (0.435 g, 1.625) in dry acetonitrile, cesium carbonate (0.794 g, 2.43 mM) was added and stirred overnight. The mixture was filtered and residue was washed with acetonitrile. The filtrate was concentrated to give 5-((2-bromo-5-fluorobenzyl)oxy)picolinaldehyde. Yield: 0.38 g, 76%; $^1$H NMR (300 MHz, DMSO-d$_6$) δ: 9.90 (s, 1H), 8.62-8.61 (d, J=8.7 Hz, 1H), 7.99-7.96 (d, J=9.3 Hz, 1H), 7.77-7.70 (m, 2H), 7.57-7.53 (dd, J=3, 9.3 Hz, 1H), 7.28-7.22 (m, 1H), 5.31 (s, 2H); MS (E/Z): 311.9 (M+1).

Step 18b

Synthesis of (E)-ethyl 3-(5-((2-bromo-5-fluorobenzyl)oxy)pyridin-2-yl)acrylate To a stirred solution of 5-((2-bromo-5-fluorobenzyl)oxy) picolinaldehyde (0.500 g, 1.612 mM) and ethyl 2-(diethoxyphosphoryl) acetate (0.434 g, 1.93 5 mM) in dry THF at 0° C., sodium hydride (0.077 g, 1.935 mM) was added and stirred at RT for overnight. The mixture was diluted with ethyl acetate and washed with brine. The organic layer was dried over sodium sulfate and concentrated to give the title compound. Yield: 0.360 g, 58.7%; $^1$H NMR (300 MHz, DMSO-d$_6$) δ: 8.46-8.45 (d, J=2.7 Hz, 1H), 7.78-7.71 (m, 2H), 7.65-7.60 (d, T=15.6 Hz, 1H), 7.58-7.50 (m, 2H), 7.27-7.21 (m, 1H), 6.76-6.71 (d, T=15.6 Hz, 1H), 5.23 (s, 2H), 4.22-4.15 (m, 2H), 1.27-1.22 (t, 3H); MS (E/Z): 382.6 (M+1).

Step 18c

Synthesis of (E)-ethyl 3-(5-((4'-(1-cyanocyclopropyl)-4-fluoro-[1,1'-biphenyl]-2-yl)methoxy)pyridin-2-yl)acrylate The mixture of (E)-ethyl 3-(5-((2-bromo-5-fluorobenzyl) oxy)pyridin-2-yl)acrylate (0.150 g, 0.345 mM), (4-(1-cyano cyclopropyl)phenyl)boronic acid (0.081 g, 0.431 mM), sodium carbonate (0.136 g, 0.986 mM) and bistriphenylphosphine palladium dichloride (0.023 g, 0.020 mM) was stirred in microwave at 111° C. for 15 min. The mixture was cooled, diluted with ethyl acetate and filtered through Celite®. The filtrate was concentrated, purified over silica gel using ethyl acetate or PET as eluent to give the title compound. Yield: 0.078 g, 44.7%; $^1$H NMR (300 MHz, DMSO-d$_6$) δ: 8.30 (s, 1H), 7.71-7.69 (d, J=8.1 Hz, 1H), 7.62-7.57 (d, J=15.9 Hz, 1H), 7.51-7.47 (m, 1H), 7.43-7.29 (m, 7H), 6.63-6.68 (d, J=15.9 Hz, 1H) 5.07 (s, 2H), 4.21-4.14 (m, 2H), 1.78-1.74 (q, 2H), 1.54-1.49 (m, 2H), 1.27-1.22 (t, 3H); MS (E/Z): 443.3 (M+1).

Step 18d

Synthesis of ethyl 3-(5-((4'-(1-cyanocyclopropyl)-4-fluoro-[1,1'-biphenyl]-2-yl)methoxy)pyridin-2-yl)propanoate To a stirred solution of (E)-ethyl 3-(5-((4'-(1-cyanocyclopropyl)-4-fluoro-[1,1'-biphenyl]-2-yl)methoxy)pyridin-2-yl)acrylate (0.090 g, 0.203 mM) in methanol (5 ml), nickel chloride hexahydrate (0.015 g g, 0.061 mM) was added at room temperature. The mixture was cooled and sodium borohydride (0.015 g, 0.407 mM) was added to it. The mixture was allowed to stand at room temperature and stirred for 2 h. The mixture was then filtered through Celite® and purified over silica gel using methanol/chloroform as eluent to the tilte compound. Yield: 0.080 g, 88%; $^1$H NMR (300 MHz, DMSO-d$_6$) δ: 8.10 (s, 1H), 7.40-7.37 (m, 6H), 7.21-7.17 (m, 3H), s4.98 (s, 2H), 4.00 (q, 2H), 2.90 (t, 2H), 2.65 (t, 2H), 1.76 (t, 2H), 1.53 (t, 2H), 1.12 (t, 3H); MS (E/Z): 445.5 (M+1).

Step 18e

Synthesis of 3-(5-((4'-(1-cyanocyclopropyl)-4-fluoro-[1,1'-biphenyl]-2-yl)methoxy)pyridin-2-yl)propanoic acid The title compound was prepared in an analogous manner as Example 2 involving the reaction of ethyl 3-(5-((4'-(1-cyanocyclopropyl)-4-fluoro-[1,1'-biphenyl]-2-yl)methoxy) pyridin-2-yl)propanoate (0.080 g, 0.180 mM) with LiOH.H$_2$O (1.080 mM), according to general procedure D (as described herein above). Yield: 0.051 g, 68%; $^1$H NMR (300 MHz, DMSO-d$_6$) δ: 8.11 (s, 1H), 7.38-7.21 (m, 6H), 7.21-7.15 (m, 3H), 4.99 (s, 2H), 2.87 (t, 2H), 2.58 (t, 2H), 1.76 (t, 2H), 1.54 (t, 2H); MS (E/Z): 417.5 (M+1).

Example 19

4-(4-((4-(4-(1-Cyanocyclopropyl)phenyl)pyridin-3-yl)methoxy)phenyl)butanoic acid Step 19a

Synthesis of 1-(4-(3-formylpyridin-4-yl)phenyl)cyclopropanecarbonitrile

The title compound was prepared in an analogous manner as general procedure C involving the reaction of 4-bromonicotinaldehyde (0.200 g, 1.075 mM) with (4-(1-cyanocyclopropyl)phenyl)boronic acid (0.302 g, 1.613 mM) in the presence of tetrakis(triphenylphosphine)palladium(0) (0.062 g, 0.054 mM). Yield: 0.175 g (65.6%); $^1$H NMR (300 MHz, DMSO-d$_6$) δ: 10.06 (s, 1H), 9.18 (s, 1H), 8.85 (d, J=6 Hz, 2H), 7.47-7.26 (m, 4H), 1.87-1.85 (m, 2H), 1.53-1.49 (m, 2H). MASS: MS (e/z): 249 (M+1).

Step 19b

Synthesis of 1-(4-(3-(hydroxymethyl)pyridin-4-yl)phenyl)cyclopropanecarbonitrile 1-(4-(3-formylpyridin-4-yl)phenyl)cyclopropanecarbonitrile (0.170 g, 0.685 mM) was dissolved in MeOH (10 ml), the mixture was cooled to 0° C. Then sodium(I)tetrahydroborate salt (0.031 g, 0.822 mM) was added slowly dropwise under inert atmosphere. The reaction mass was allowed to stand to room temperature and stirred for 1 h. The solvent was removed under vacuum, quenched with water and extracted using ethyl acetate (25 ml×4). The organic layers were combined, dried over anhydrous sodium sulphate, concentrated and purified by column chromatography (50% ethyl acetate:PET ether) to give the title compound. Yield: 0.146 g, 85%; $^1$H NMR (300 MHz, DMSO-$d_6$) δ: 8.76 (s, 1H), 8.60 (d, J=5.1 Hz, 1H), 7.46-7.38 (m, 4H), 7.22 (d, J=4.8 Hz, 1H), 4.66 (s, 2H), 1.83-1.79 (m, 2H), 1.50-1.46 (m, 2H); MS (E/Z): 251 (M+1).

Step 19c

Synthesis of 1-(4-(3-(chloromethyl)pyridin-4-yl)phenyl)cyclopropanecarbonitrile 1-(4-(3-(hydroxymethyl)pyridin-4-yl)phenyl)cyclopropanecarbonitrile (0.140 g, 0.559 mM) was dissolved in DCM (2 ml) and the reaction mass was cooled at 0° C. Thionyl chloride (0.041 ml, 0.559 mM) was added slowly to the mixture. The ice bath was removed, the mixture was brought to room temperature and stirred reaction mass for 1 h. The reaction mass was quenched with water and extracted with DCM (10 ml×4). The organic layers were combined and washed with sodium bicarbonate solution (10 ml×2). The organic layers were dried over anhydrous sodium sulphate, concentrated to give the title compound. Yield: 0.140 g, 93%.

Step 19d

Synthesis of methyl 4-(4-((4-(4-(1-cyanocyclopropyl)phenyl)pyridin-3-yl)methoxy)phenyl)butanoate 1-(4-(3-(chloromethyl)pyridin-4-yl)phenyl)cyclopropanecarbonitrile (0.140 g, 0.521 mM) was dissolved in acetonitrile (5 ml). cesium carbonate (0.509 g, 1.563 mM), followed by methyl 4-(4-hydroxyphenyl)butanoate (0.111 g, 0.573 mM) was added, and reaction mass was stirred at room temperature for overnight. The reaction mass was diluted with ethyl acetate and quenched with water. The aqueous layer was extracted with ethyl acetate (10 ml×4). The organic layer was combined, dried over anhydrous sodium sulphate, concentrated and purified by column chromatography (50% ethyl acetate:PET ether) to give title compound. Yield: 0.115 g, 51.5%. $^1$H NMR (300 MHz, DMSO-$d_6$) δ: 8.82 (s, 1H), 8.66 (d, J=5.1 Hz, 1H), 7.46 (d, J=8.4 Hz, 2H), 7.38-7.35 (d, J=8.4 Hz, 2H), 7.28 (m, 2H), 7.12-7.09 (d, J=8.4 Hz, 2H), 6.84-6.81 (d, J=8.7 Hz, 1H), 4.92 (s, 2H), 3.68 (s, 3H), 2.64-2.59 (m, 2H), 2.36-2.31 (m, 2H), 1.99-1.89 (m, 2H), 1.82-1.78 (m, 2H), 1.49-1.45 (m, 2H); MS (E/Z): 427 (M+1)

Step 19e

Synthesis of 4-(4-((4-(4-(1-cyanocyclopropyl)phenyl)pyridin-3-yl)methoxy)phenyl)butanoic acid The title compound was prepared in an analogous manner as Example 1 involving the reaction of methyl 4-(4-((4-(4-(1-cyanocyclopropyl)phenyl)pyridin-3-yl)methoxy)phenyl)butanoate (0.100 g, 0.234 mM) with LiOH.H$_2$O (0.938 ml, 1.5M), according to general procedure D (as described herein above). Yield: 0.078 g, 81%; $^1$H NMR (300 MHz, DMSO-$d_6$) δ: 8.79 (s, 1H), 8.65 (d, J=5.1 Hz, 1H), 7.46 (d, J=8.1 Hz, 2H), 7.37 (d, =8.1 Hz, 2H), 7.12-7.09 (d, J=8.4 Hz, 2H), 6.83-6.80 (d, J=8.7 Hz, 2H), 4.91 (s, 2H), 2.66-2.61 (m, 2H), 2.39-2.34 (m, 2H), 1.98-1.93 (m, 2H), 1.81-1.77 (m, 2H), 1.48-1.44 (m, 2H); MS (E/Z): 413 (M+1).

Example 20

3-(5-((2-(Bicyclo[4.2.0]octa-1(6),2,4-trien-3-yl)-5-fluorobenzyl)oxy)pyridin-2-yl)propanoic acid Step 20a

Synthesis of ethyl 3-(5-((2-(bicyclo[4.2.0]octa-1(6),2,4-trien-3-yl)-5-fluorobenzyl)oxy)pyridin-2-yl)propanoate A mixture of (E)-ethyl 3-(5-((5-fluoro-2-(4,4,5,5-tetramethyl-1,3,2-dioxaborolan-2-yl)benzyl)oxy)pyridin-2-yl)acrylate (0.150 g, 0.351 mM), 3-bromobicyclo[4.2.0]octa-1(6),2,4-triene (0.096 g, 0.527 mM), K$_2$CO$_3$ (0.121 g, 0.878 mM) was dissolved in dioxane:water (8:2 ml). The mixture was degassed using argon for 5 min. Triphenylphosphine (0.201 g, 0.246 mM) was added and the reaction mixture was degassed for 5 min. Then, palladium salt (0.020 g) was added, and degassed for further for 5 min. The reaction was heated at 80° C. for 4 h, reaction was monitored by TLC (20% ethyl acetate:PET ether). The dioxane was removed under high vacuum, diluted with water, aqueous layer was extracted with ethyl acetate, dried over sodium sulfate and purified with column chromatography to give the title compound. Yield: 0.097 g, 0.240 mM, 68.5%. $^1$H NMR (300 MHz, DMSO-$d_6$) δ: 8.30 (s, 1H), 7.70 (d, J=8.4, 1H), 7.62 (d, J=15.6, 1H), 7.46 (d, J=9.6 Hz, 1H), 7.36-7.27 (m, 3H), 7.17-7.08 (m, 2H), 6.73 (d, J=15.6 Hz, 1H), 5.05 (s, 2H), 4.17 (q, J=7.2 Hz, 2H), 3.13 (s, 4H), 1.25 (t, J=7.2 Hz, 3H); MS (E/Z): 404 (M+1).

Step 20b

Synthesis of 3-(5-((2-(bicyclo[4.2.0]octa-1(6),2,4-trien-3-yl)-5-fluorobenzyl)oxy)pyridin-2-yl)propanoic acid The title compound was prepared in an analogous manner as Example 2 involving the reaction of ethyl-3-(5-((2-(bicyclo[4.2.0]octa-1(6),2,4-trien-3-yl)-5-fluorobenzyl)oxy)pyridin-2-yl)propanoate (0.085 g, 0.210 mM) with LiOH.H$_2$O (0.839 ml, 1.5M), according to general procedure D (as described herein above). Yield: 54%; $^1$H NMR (300 MHz, DMSO-$d_6$) δ: 12.08 (s, 1H), 8.11 (d, J=2.7 Hz, 1H), 7.43-7.39 (m, 1H), 7.34-7.29 (m, 2H), 7.25-7.07 (m, 5H), 4.96 (s, 2H), 3.14 (s, 4H), 2.87 (t, J=7.2 Hz, 2H), 2.58 (t, J=7.5 Hz, 2H); MS (E/Z): 378 (M+1).

Example 21

3-(4-((2-(4-(1-Cyanocyclopropyl)phenyl)pyridin-3-yl)methoxy)phenyl)propanoic acid Step 21a

Synthesis of methyl 3-(4-((2-bromopyridin-3-yl)methoxy)phenyl)propanoate

A mixture of (2-bromopyridin-3-yl)methanol (0.500 g, 2.66 mM), methyl 3-(4-hydroxyphenyl)propanoate (0.479 g, 2.66 mM), PPh₃ (0.697 g, 2.66 mM) was dissolved in THF (5 ml), cooled to 0° C. (E)-diethyl diazene-1,2-dicarboxylate (0.463 g, 2.66 mM) was added slowly into the reaction mixture. The reaction mixture was stirred at RT for overnight and THF was removed under vacuum and then reaction mass was quenched with water. The aqueous layer was extracted by ethyl acetate, combined the organic layer, dried over Na₂SO₄, concentrated and purified by column chromatography to give the title compound. Yield: 0.60 g, 64%; ¹H (DMSOd₆, 300 MHz): δ 8.36-8.34 (m, 1H), 7.95 (d, J=6 Hz, 1H), 7.49 (q, J=4.5 Hz, J=7.2 Hz, 1H), 7.16 (d, J=8.7 Hz, 2H), 6.65 (d, J=8.4 Hz, 2H), 5.07 (s, 2H), 3.56 (s, 3H), 2.77 (t, J=7.5 Hz, J=15 Hz, 2H), 2.55 (t, J=7.5 Hz, J=14.1 Hz, 2H). MS (e/z): 352 [M+2].

Step 21b

Synthesis of ethyl 3-(4-((2-(4-(1-cyanocyclopropyl)phenyl)pyridin-3-yl)methoxy)phenyl)propanoate Methyl 3-(4-((2-bromopyridin-3-yl)methoxy)phenyl)propanoate (0.150 g, 0.428 mM) and (4-(1-cyanocyclopropyl)phenyl)boronic acid (0.096 g, 0.514 mM) were dissolved in dioxane:water (4:1) and K₂CO₃ (0.148 g, 1.07 mM) was added into it. The reaction mixture was degassed under argon, followed by the addition of triphenylphosphine palladium salt (0.006 g, 0.021 mM) and irradiated at 120° C. for 20 min in microwave. The dioxane was removed under high vacuum, diluted with water, aqueous layer was extracted with ethyl acetate, dried over sodium sulfate and purified with column chromatography to give the title compound. Yield: 0.14 g, 77%; ¹H NMR (300 MHz, DMSO-d₆) δ: 8.66-8.65 (d, J=4.5 Hz, 1H), 8.12-8.00 (m, 1H), 7.65-7.63 (m, 2H), 7.41-7.39 (m, 3H), 7.13-7.11 (m, 2H), 6.85-6.83 (m, 2H), 5.01 (s, 2H), 3.57 (s, 3H), 2.77-2.75 (m, 2H), 2.59-2.58 (m, 2H), 1.79 (s, 2H), 1.58 (s, 2H); MS (E/Z): 413 (M+1).

Step 21c

Synthesis of 3-(4-((2-(4-(1-cyanocyclopropyl)phenyl)pyridin-3-yl)methoxy)phenyl)propanoic acid The title compound was prepared in an analogous manner as Example 2 involving the reaction of ethyl-3-(4-((2-(4-(1-cyanocyclopropyl)phenyl)pyridin-3-yl)methoxy)phenyl)propanoate (0.130 g, 0.315 mM) with LiOH.H₂O (1.261 ml, 1.5M) according to general procedure D (as described herein above). Yield: 88%; ¹H NMR (300 MHz, DMSO-d₆) δ: 12.08 (s, 1H), 8.67-8.66 (d, J=4.5 Hz, 1H), 7.65-7.64 (m, 3H), 7.41-7.40 (m, 2H), 7.14-7.12 (m, 2H), 6.85-6.83 (m, 2H), 5.02 (s, 2H), 2.74-2.72 (m, 2H), 2.50-2.48 (m, 2H), 1.79 (s, 2H), 1.58 (s, 2H); MS (E/Z): 378 (M+1), 399 (M+1).

Example 22

4-(4-((2-(2,3-Dihydrobenzofuran-5-yl)-5-fluorobenzyl)oxy)phenyl)butanoic acid Step 22a

Synthesis of methyl 4-(4-((2-(2,3-dihydrobenzofuran-5-yl)-5-fluorobenzyl)oxy)phenyl)butanoate The title compound was prepared in an analogous manner as step 12a of Example 12 involving the reaction of methyl-4-(4-((2-bromo-5-fluorobenzyl)oxy)phenyl)butanoate (compound of step 1a of Example 1) (120 mg, 0.315 mM) with (2,3-dihydrobenzofuran-5-yl)boronic acid (103 mg, 0.630 mM), according to general procedure C (as described herein above). Yield: 90 mg, 0.206 mM, 65.5%; ¹H NMR (300 MHz, CDCl₃) δ: 7.40-7.31 (m, 1H), 7.26-7.23 (m, 1H), 7.15 (s, 1H), 7.07-7.01 (m, 4H), 6.82-6.77 (m, 3H), 4.89 (s, 2H), 4.61 (t, J=8.7 Hz, 2H), 3.66 (s, 3H), 3.21 (t, J=8.7 Hz, 2H), 2.58 (t, J=7.2 Hz, 2H), 2.31 (t, J=7.5 Hz, 2H), 1.96-1.86 (m, 2H); MS (E/Z): 443.2 (M+Na).

Step 22b

Synthesis of 4-(4-((2-(2,3-Dihydrobenzofuran-5-yl)-5-fluorobenzyl)oxy)phenyl)butanoic acid The title compound was prepared in an analogous manner as Example 1 involving the reaction of methyl 4-(4-((2-(2,3-dihydrobenzofuran-5-yl)-5-fluorobenzyl)oxy)phenyl)butanoate (75 mg, 0.178 mM) with LiOH.H₂O (37.4 mg, 0.892 mM), according to general procedure D (as described herein above). Yield: 62 mg, 0.153 mM, 86%; ¹H NMR (300 MHz, DMSO-d₆) δ: 12.02 (bs, 1H), 7.38-7.29 (m, 2H), 7.23-7.19 (m, 2H), 7.09-7.04 (m, 3H), 6.81-6.76 (m, 3H), 4.90 (s, 2H), 4.53 (t, J=8.7 Hz, 2H), 3.14 (t, J=8.7 Hz, 2H), 2.44-2.48 (m, 2H), 2.16 (t, J=7.2 Hz, 2H), 1.77-1.70 (m, 2H); MS (E/Z): 429.0 (M+Na).

Example 23

4-(4-((5-Fluoro-2-(4,5,6,7-tetrahydrobenzo[b]thiophen-2-yl)benzyl)oxy)phenyl)butanoic acid Step 23a

Synthesis of methyl 4-(4-((5-fluoro-2-(4,5,6,7-tetrahydrobenzo[b]thiophen-2-yl)benzyl)oxy)phenyl)butanoate The title compound was prepared in an analogous manner as Example 1 involving the reaction of 2-bromo-4,5,6,7-tetrahydrobenzo[b]thiophene (73.0 g, 336 mM) with methyl-4-(4-((5-fluoro-2-(4,4,5,5-tetramethyl-1,3,2-dioxaborolan-2-yl)benzyl)oxy)phenyl)butanoate (120 mg, 280 mM) and potassium carbonate (97 mg, 700 mM) in presence of tetrakis(triphenyl)phosphine palladium(0) (19.4 mg, 16.81 mM), according to general procedure C (as described herein above). Yield: 78.2 mg, 178 mM, 63.5%; ¹H NMR (300 MHz, CDCl₃) δ: 7.42-7.32 (m, 2H), 7.10-7.00 (m, 3H), 6.85 (d, J=8.4 Hz, 2H), 6.68 (s, 1H), 5.08 (s, 2H), 3.66 (s, 3H), 2.78 (t, J=7.5 Hz, 2H), 2.59 (t, J=7.2 Hz, 4H), 2.32 (t, J=7.2 Hz, 2H), 1.97-1.84 (m, 6H); MS (E/Z): 439.8 (M+H).

Step 23b

Synthesis of 4-(4-((5-fluoro-2-(4,5,6,7-tetrahydrobenzo[b]thiophen-2-yl)benzyl)oxy)phenyl)butanoic acid The title compound was prepared in an analogous manner as Example 1 involving the reaction of methyl 4-(4-((5-fluoro-2-(4,5,6,7-tetrahydrobenzo[b]thiophen-2-yl)benzyl)oxy)phenyl)butanoate (80 mg, 0.182 mM) with LiOH.H₂O (38.2 mg, 0.912 mM), according to general procedure D (as described herein above). Yield: 63.2 mg, 0.148 mM, 81%; ¹H NMR (300 MHz, CDCl₃) δ: 12.04 (bs, 1H), 7.47-7.40 (m, 2H), 7.27-7.24 (m, 1H), 7.10 (d, J=8.1 Hz, 2H), 6.88-6.84 (m, 3H), 5.04 (s, 2H), 2.69 (t, J=7.5 Hz, 2H), 2.54-2.45 (m, 4H), 2.17 (t, J=7.2 Hz, 2H), 1.78-1.68 (m, 6H); MS (E/Z): 425.1 (M+H), 422.9 (M−H).

Example 24

4-(4-((2-(6,7-Dihydro-5H-cyclopenta[b]pyridin-3-yl)-5-fluorobenzyl)oxy)phenyl)butanoic acid Step 24a

Synthesis of methyl 4-(4-((2-(6,7-dihydro-5H-cyclopenta[b]pyridin-3-yl)-5-fluorobenzyl)oxy)phenyl)butanoate The title compound was prepared in an analogous manner as Example 1 involving the reaction of 3-bromo-6,7-dihydro-5H-cyclopenta[b]pyridine (78 mg, 0.395 mM) with methyl-4-(4-((5-fluoro-2-(4,4,5,5-tetramethyl-1,3,2-dioxaborolan-2-yl)benzyl)oxy)phenyl)butanoate (130 mg, 0.304 mM) and potassium carbonate (105 mg, 0.759 mM) in presence of tetrakis(triphenyl)phosphine palladium(0) (21.04 mg, 0.018 mM) according to general procedure C (as described herein above). Yield: 87.8 mg, 0.209 mM, 69.0%; $^1$H NMR (300 MHz, CDCl$_3$) δ: 7.43-7.23 (m, 5H), 7.55 (d, J=8.4 Hz, 2H), 7.78 (d, J=8.4 Hz, 2H), 4.90 (s, 2H), 3.66 (s, 3H), 3.05 (t, J=7.8 Hz, 2H), 2.93 (t, J=7.2 Hz, 2H), 2.58 (t, J=7.5 Hz, 2H), 2.31 (t, J=7.5 Hz, 2H), 2.20-2.15 (m, 2H), 1.93-1.88 (m, 2H); MS (E/Z): 420.5 (M+H).

Step 24b

Synthesis of 4-(4-((2-(6,7-dihydro-5H-cyclopenta[b]pyridin-3-yl)-5-fluorobenzyl)oxy)phenyl)butanoic acid The title compound was prepared in an analogous manner as Example 1 involving the reaction of methyl 4-(4-((2-(6,7-dihydro-5H-cyclopenta[b]pyridin-3-yl)-5-fluorobenzyl)oxy)phenyl)butanoate (47 mg, 0.112 mM) with LiOH.H$_2$O (23.5 mg, 0.560 mM), according to general procedure D (as described herein above). Yield: 40.4 mg, 0.099 mM, 88%; $^1$H NMR (300 MHz, DMSO-d$_6$) δ: 12.03 (bs, 1H), 8.27 (s, 1H), 7.62 (s, 1H), 7.47-7.26 (m, 3H), 7.06 (d, J=8.4 Hz, 2H), 6.80 (d, J=8.7 Hz, 2H), 4.89 (s, 2H), 2.92-2.83 (m, 4H), 2.16 (t, J=7.2 Hz, 2H), 2.07 (t, J=7.5 Hz, 2H), 2.10-2.02 (m, 2H), 1.74-1.69 (m, 2H); MS (E/Z): 406.5 (M+H).

Example 25

4-(4-((5-Fluoro-2-(7-methylene-4,5,6,7-tetrahydrobenzo[d]thiazol-2-yl)benzyl)oxy)phenyl)butanoic acid Step 25a

Synthesis of 2-bromo-7-methylene-4,5,6,7-tetrahydrobenzo[d]thiazole

To a stirred solution of 1,1'-biphenyl compound with bromo(methylene)(phenyl)phosphorane (1:1) (400 mg, 1.120 mM) dissolved in dry THF (10 ml), n-butyllithium was added (646 μl, 1.034 mM) at −78° C. and allowed to stir for 30-40 min. 2-bromo-5,6-dihydrobenzo[d]thiazol-7(4H)-one (200 mg, 0.862 mM) was slowly added to the mixture and the mixture was allowed to stir at room temperature for 3-5 h. After completion of reaction, the mixture was quenched with ammonium chloride, extracted with ethyl acetate, concentrated and purified by column chromatography to give the title compound. Yield: 120 mg, 0.521 mM, 60.5%; $^1$H NMR (300 MHz, CDCl$_3$) δ: 5.00 (s, 1H), 4.93 (s, 1H), 2.84 (t, J=6.3 Hz, 2H), 2.51-2.47 (m, 2H), 1.96-1.88 (m, 2H); HPLC: 73.96%; MS (E/Z): 229.9 (M$^+$).

Step 25b

Synthesis of methyl 4-(4-((5-fluoro-2-(7-methylene-4,5,6,7-tetrahydrobenzo[d]thiazol-2-yl)benzyl)oxy)phenyl)butanoate The title compound was prepared in an analogous manner as Example 1 involving the reaction of 2-bromo-7-methylene-4,5,6,7-tetrahydrobenzo[d]thiazole (56.4 mg, 0.245 mM) with methyl 4-(4-((5-fluoro-2-(4,4,5,5-tetramethyl-1,3,2-dioxaborolan-2-yl)benzyl)oxy)phenyl)butanoate (70 mg, 0.163 mM) and potassium carbonate (70.6 mg, 0.511 mM) in presence of tetrakis(triphenyl)phosphine palladium (0) (14.16 mg, 0.012 mM), according to general procedure C (as described herein above). Yield: 62 mg, 0.135 mM, 66.0%; $^1$H NMR (300 MHz, CDCl$_3$) δ: 7.73-7.68 (m, 1H), 7.49-7.47 (m, 1H), 7.10-7.02 (m, 3H), 6.87 (d, J=8.7 Hz, 2H), 5.46 (s, 2H), 5.13 (s, 1H), 4.95 (s, 1H), 3.66 (s, 3H), 2.89 (t, J=6.00 Hz, 2H), 2.62-2.53 (m, 4H), 2.32 (t, J=7.5 Hz, 2H), 2.02-1.87 (m, 4H); MS (E/Z): 452.5 (M+H).

Step 25c

Synthesis of 4-(4-((5-fluoro-2-(7-methylene-4,5,6,7-tetrahydrobenzo[d]thiazol-2-yl)benzyl)oxy)phenyl)butanoic acid The title compound was prepared in an analogous manner as Example 1 involving the reaction of methyl-4-(4-((5-fluoro-2-(7-methylene-4,5,6,7-tetrahydrobenzo[d]thiazol-2-yl)benzyl)oxy)phenyl)butanoate (55 mg, 0.122 mM) with LiOH.H$_2$O (25.6 mg, 0.183 mM), according to general procedure D (as described herein above). Yield: 40.4 mg, 0.099 mM, 88%; $^1$H NMR (300 MHz, DMSO-d$_6$) δ: 12.02 (bs, 1H), 7.86-7.82 (m, 1H), 7.50-7.47 (m, 1H), 7.34-7.29 (m, 1H), 7.09 (d, J=8.4 Hz, 2H), 6.85 (d, J=8.1 Hz, 2H), 5.41 (s, 2H), 5.01 (d, J=7.5 Hz, 2H), 2.76 (t, J=5.7 Hz, 2H), 2.52-2.45 (m, 4H), 2.17 (t, J=7.2 Hz, 2H), 1.86-1.84 (m, 2H), 1.78-1.71 (m, 2H); MS (E/Z): 438.3 (M+H).

Example 26

4-(4-((2-(Bicyclo[4.2.0]octa-1(6),2,4-trien-3-yl)benzyl)oxy)phenyl)butanoic acid Step 26a

Synthesis of methyl 4-(4-((2-(bicyclo[4.2.0]octa-1(6),2,4-trien-3-yl)benzyl)oxy)phenyl)butanoate The title compound was prepared in an analogous manner as step 12a of Example 12 involving the reaction of methyl 4-(4-((2-bromo-5-fluorobenzyl)oxy)phenyl)butanoate (compound of step 1a of Example 1) (100 mg, 0.275 mM) with bicyclo[4.2.0]octa-1(6),2,4-trien-3-ylboronic acid (61.1 mg, 0.413 mM), according to general procedure C (as described herein above). Yield: 85 mg, 0.22 mM, 80%; $^1$H NMR (300 MHz, CDCl$_3$) 7.60-7.63 (m, 1H), 7.33-7.40 (m, 2H), 7.27-7.32 (m, 1H), 7.21 (d, J=8.1 Hz, 1H), 7.06 (t, J=8.1 Hz, 4H), 6.81 (d, J=8.7 Hz, 2H), 4.98 (s, 2H), 3.66 (s, 3H), 3.21 (s, 4H), 2.60 (t, J=7.5 Hz, 2H), 2.34 (t, J=7.5 Hz, 2H), 1.89-1.96 (m, 2H); MS m/z 387.3 [M+1].

Step 26b

Synthesis of 4-(4-((2-(bicyclo[4.2.0]octa-1(6),2,4-trien-3-yl)benzyl)oxy)phenyl)butanoic acid The title compound was prepared in an analogous manner as Example 1 involving the reaction of methyl 4-(4-((2-

(bicyclo[4.2.0]octa-1(6),2,4-trien-3-yl)benzyl)oxy)phenyl) butanoate (80 mg, 0.207 mM) with LiOH.H$_2$O (43.4 mg, 1.03 mM), according to general procedure D (as described herein above). Yield: 55 mg, 0.148 mM, 71.3%; $^1$H NMR (300 MHz, DMSO-d$_6$) δ 12.03 (s, 1H), 7.54-7.57 (m, 1H), 7.40 (t, J=3.9 Hz, 2H), 7.24-7.27 (m, 1H), 7.19 (d, J=7.8 Hz, 1H), 7.03-7.10 (m, 4H), 6.79 (d, J=7.8 Hz, 2H), 4.88 (s, 2H), 3.13 (s, 4H), 2.48 (m, 2H), 2.16 (t, J=7.2 Hz, 2H), 1.69-1.76 (m, 2H); MS, m/z 370.8 [M−1].

Example 27

4-(4-((2-(5,6,7,8-tetrahydronaphthalen-2-yl)benzyl) oxy)phenyl)butanoic acid

Step 27a

Synthesis of methyl 4-(4-((2-(5,6,7,8-tetrahydronaphthalen-2-yl)benzyl)oxy)phenyl)butanoate The title compound was prepared in an analogous manner as step 12a of Example 12 involving the reaction of methyl 4-(4-((2-bromo-5-fluorobenzyl)oxy)phenyl)butanoate (compound of step 1a of Example 1) (100 mg, 0.275 mM) with (5,6,7,8-tetrahydronaphthalen-2-yl)boronic acid (72.7 mg, 0.413 mM), according to general procedure C (as described herein above). Yield: 95 mg, 0.229 mM, 83%; $^1$H NMR (300 MHz, CDCl$_3$) δ 7.59-7.60 (m, 1H), 7.32-7.39 (m, 3H), 7.04-7.13 (m, 5H), 6.83 (d, J=8.4 Hz, 2H), 4.93 (s, 2H), 3.66 (s, 3H), 2.72 (m, 4H), 2.58 (t, J=7.8 Hz, 2H), 2.31 (t, J=7.8 Hz, 2H), 1.86-1.96 (m, 2H), 1.77-1.81 (m, 4H); MS m/z 437.0 [M+Na$^+$]

Step 27b

Synthesis of 4-(4-((2-(5,6,7,8-tetrahydronaphthalen-2-yl)benzyl)oxy)phenyl)butanoic acid The title compound was prepared in an analogous manner as Example 1 involving the reaction of methyl-4-(4-((2-(5,6,7,8-tetrahydronaphthalen-2-yl)benzyl)oxy)phenyl)butanoate [90 mg, 0.217 m mol] with LiOH.H$_2$O [46 mg, 1.08 mM], according to general procedure D (as described above). Yield: 60 mg, 0.150 m mol, 69.0%; $^1$H NMR (300 MHz, DMSO-d$_6$) δ 12.03 (s, 1H), 7.55-7.57 (m, 1H), 7.30-7.39 (m, 3H), 7.04-7.07 (m, 5H), 6.81 (d, J=8.4 Hz, 2H), 4.88 (s, 2H), 2.60-2.70 (m, 4H), 2.47-2.49 (m, 2H), 2.16 (t, J=7.2 Hz, 2H), 1.69-1.72 (m, 6H); MS m/z 398.8 [M−1].

Example 28

4-(4-((2-(5-Cyclobutylthiophen-2-yl)-5-fluorobenzyl)oxy)phenyl)butanoic acid

Step 28a

Synthesis of methyl 4-(4-((2-(5-cyclobutylthiophen-2-yl)-5-fluorobenzyl)oxy)phenyl)butanoate The title compound was prepared in an analogous manner as step 1c of Example 1 involving the reaction of methyl 4-(4-((5-fluoro-2-(4,4,5,5-tetramethyl-1,3-dioxolan-2-yl) benzyl)oxy)phenyl)butanoate (compound of step 1a of Example 1) [100 mg, 0.232 mM] with 2-bromo-5-cyclobutylthiophene [76 mg, 0.348 mM] according to general procedure C (as described herein above). Yield: 40 mg, 0.091 mM, 39.3%; $^1$H NMR (CDCl$_3$, 300 MHz) δ 7.32-7.44 (m, 2H), 7.01-7.10 (m, 3H), 6.83-6.87 (m, 3H), 6.76 (d, J=3.3 Hz, 1H), 5.06 (s, 2H), 3.66 (s, 3H), 2.59 (t, J=7.5 Hz, 2H), 2.41-2.44 (m, 2H), 2.20 (t, J=9.3 Hz, 2H), 2.14-2.16 (m, 2H), 2.01-2.04 (m, 2H), 1.90-1.98 (m, 3H); MS m/z 439.0 [M+1].

Step 28b

Synthesis of 4-(4-((2-(5-cyclobutylthiophen-2-yl)-5-fluorobenzyl)oxy)phenyl)butanoic acid The title compound was prepared in an analogous manner as Example 1 involving the reaction of methyl 4-(4-((2-(5-cyclobutylthiophen-2-yl)-5-fluorobenzyl)oxy)phenyl)butanoate [40 mg, 0.091 mM] with LiOH.H$_2$O [19.14 mg, 0.45 mM], according to general procedure D (as described herein above). Yield: 20 mg, 0.047 mM, 51.7%; $^1$H NMR (DMSO d$_6$, 300 MHz) δ 12.02 (s, 1H), 7.42-7.51 (m, 2H), 7.23-7.29 (m, 1H), 7.10 (d, J=8.4 Hz, 2H), 7.08 (d, J=3.6 Hz, 1H), 6.84-6.88 (m, 3H), 5.02 (s, 2H), 3.64-3.70 (m, 1H), 2.48 (m, 2H), 2.32-2.35 (m, 2H), 2.15-2.20 (t, J=7.2 Hz, 2H), 1.71-1.97 (m, 4H), 1.16-1.22 (m, 2H); MS m/z 446.8 [M+Na$^+$].

Example 29

4-(4-((4'-cyclopropyl-4-fluoro-3'-methyl-[1,1'-biphenyl]-2-yl)methoxy)phenyl)butanoic acid Step 29a Synthesis of methyl 4-(4-((4'-cyclopropyl-4-fluoro-3'-methyl-[1,1'-biphenyl]-2-yl)methoxy)phenyl)butanoate The title compound was prepared in an analogous manner as step 1c of Example 1 involving the reaction of methyl 4-(4-((5-fluoro-2-(4,4,5,5-tetramethyl-1,3-dioxolan-2-yl) benzyl)oxy)phenyl)butanoate (compound of step 1a of Example 1) [100 mg, 0.232 mM] with 4-bromo-1-cyclopropyl-2-methylbenzene [73.9 mg, 0.350 mM] according to general procedure C (as described herein above). Yield: 55 mg, 0.127 mM, 54.5%; $^1$H NMR (300 MHz, CDCl$_3$) δ: 7.35 (d, J=7.2 Hz, 1H), 6.90-7.18 (m, 7H), 6.79 (d, J=8.7 Hz, 2H), 4.90 (s, 2H), 3.36 (s, 3H), 2.60 (t, J=7.5 Hz, 2H), 2.42 (s, 3H), 2.28-2.36 (m, 3H), 1.88-1.96 (m, 2H), 0.93-0.99 (m, 2H), 0.67-0.70 (m, 2H); MS m/z 433.4 [M+1].

Step 29b 4-(4-((4'-cyclopropyl-4-fluoro-3'-methyl-[1,1'-biphenyl]-2-yl)methoxy)phenyl)butanoic acid The title compound was prepared in an analogous manner as Example 1 involving the reaction of methyl 4-(4-((4'-cyclopropyl-4-fluoro-3'-methyl-[1,1'-biphenyl]-2-yl) methoxy)phenyl)butanoate [50 mg, 0.116 mM] with LiOH.H$_2$O [24.2 mg, 0.578 mM] according to general procedure D (as described herein above). Yield: 15 mg, 0.036 mM, 31.0%; $^1$H NMR (300 MHz, DMSO-d$_6$) δ: 12.02 (s, 1H), 7.27-7.40 (m, 2H), 6.93-7.16 (m, 4H), 6.93-6.96 (d, J=8.1 Hz, 2H), 6.77-6.80 (d, J=8.4 Hz, 2H), 4.88 (s, 2H), 3.32 (s, 3H), 2.32 (s, 2H), 2.16 (t, J=7.2 Hz, 2H), 1.89 (m, 1H), 1.72-1.74 (m, 2H), 0.86-0.92 (m, 2H), 0.60-0.61 (m, 2H); MS m/z 416.9 [M−1].

Example 30

4-(4-((2-(6-Cyclopropylpyridin-3-yl)-5-fluorobenzyl)oxy)phenyl)butanoic acid

Step 30a

Synthesis of methyl 4-(4-((2-(6-cyclopropylpyridin-3-yl)-5-fluorobenzyl)oxy)phenyl)butanoate The title compound was prepared in an analogous manner as step 1c of Example 1 involving the reaction of methyl 4-(4-((5-fluoro-2-(4,4,5,5-tetramethyl-1,3-dioxolan-2-yl) benzyl)oxy)phenyl)butanoate (compound of step 1a of Example 1) [100 mg, 0.232 mM] with 5-bromo-2-cyclopropylpyridine [69.4 mg, 0.350 mM], according to general procedure C (as described herein above). Yield: 55 mg, 0.131 m mol, 56.2%; $^1$H NMR (300 MHz, CDCl$_3$) δ: 8.42 (s, 1H), 7.56 (d, J=7.8 Hz, 1H), 7.35 (d, J=9.6 Hz, 1H), 7.00-7.17 (m, 5H), 6.76 (d, J=8.4 Hz, 2H), 4.87 (s, 2H), 3.67 (s, 3H), 2.61 (t, J=7.2 Hz, 2H), 2.34 (t, J=7.2 Hz, 2H), 2.08-2.10 (m, 1H), 1.89-1.94 (m, 2H), 1.05 (d, J=8.1 Hz, 4H); MS m/z 420.5 [M+1].

Step 30b

Synthesis of 4-(4-((2-(6-cyclopropylpyridin-3-yl)-5-fluorobenzyl)oxy)phenyl)butanoic acid The title compound was prepared in an analogous manner as Example 1 involving the reaction of methyl 4-(4-((2-(6-cyclopropylpyridin-3-yl)-5-fluorobenzyl)oxy)phenyl)butanoate [50 mg, 0.119 mM] with LiOH.H$_2$O [25 mg, 0.59 mM], according to general procedure D (as described herein above). Yield: 30 mg, 0.074 mM, 62.1%; $^1$H NMR (DMSO d$_6$, 300 MHz) δ: 11.94 (s, 1H), 8.55 (s, 1H), 7.33-7.50 (m, 3H), 6.98-7.07 (m, 3H), 6.79 (d, J=8.1 Hz, 2H), 6.72 (d, J=8.1 Hz, 1H), 4.95 (s, 2H), 2.26 (s, 1H), 2.15-2.17 (m, 3H), 1.70-1.75 (m, 3H), 1.05-1.15 (m, 4H); MS, m/z 407.4 [M+2].

Example 31

4-(4-((2-(2-Cyclopropylpyrimidin-5-yl)-5-fluorobenzyl)oxy)phenyl)butanoic acid Step 31a

Synthesis of methyl 4-(4-((2-(2-cyclopropylpyrimidin-5-yl)-5-fluorobenzyl)oxy)phenyl)butanoate The title compound was prepared in an analogous manner as step 1c of Example 1 involving the reaction of methyl 4-(4-((5-fluoro-2-(4,4,5,5-tetramethyl-1,3-dioxolan-2-yl) benzyl)oxy)phenyl)butanoate (compound of step 1a of Example 1) [100 mg, 0.232 m mol] with 5-bromo-2-cyclopropylpyrimidine (69.7 mg, 0.350 mM), according to general procedure C (as described herein above). Yield: 55 mg, 0.131 mM, 56.0%; $^1$H NMR (300 MHz, CDCl$_3$) δ: 8.58 (s, 2H), 7.40 (d, J=6.9 Hz, 1H), 7.06-7.23 (m, 2H), 7.13 (d, J=8.4 Hz, 2H), 6.79 (d, J=8.4 Hz, 2H), 4.85 (s, 2H), 3.67 (s, 3H), 2.61 (t, J=7.5 Hz, 2H), 2.26-2.34 (m, 3H), 1.86-1.96 (m, 2H), 1.11-1.17 (m, 4H); MS m/z 421.5 [M+1].

Step 31b

Synthesis of 4-(4-((2-(2-cyclopropylpyrimidin-5-yl)-5-fluorobenzyl)oxy)phenyl)butanoic acid The title compound was prepared in an analogous manner as Example 1 involving the reaction of methyl-4-(4-((2-(2-cyclopropylpyrimidin-5-yl)-5-fluorobenzyl)oxy)phenyl)butanoate [50 mg, 0.119 mM] with LiOH.H$_2$O [25 mg, 0.59 mM], according to general procedure D (as described herein above). Yield: 32 mg, 0.079 mM, 66.2%; $^1$H NMR (300 MHz, DMSO-d$_6$) δ: 12.02 (s, 1H), 8.66 (s, 2H), 7.33-7.51 (m, 3H), 7.05-7.07 (d, J=7.8 Hz, 2H), 6.81 (d, J=8.1 Hz, 2H), 4.94 (s, 2H), 2.49 (m, 2H), 2.15-2.17 (m, 3H), 1.70-1.75 (m, 2H), 0.99-1.03 (m, 4H); MS m/z 406.6 [M$^+$].

Example 32

4-(4-((2-(4-Cyclopropylthiazol-5-yl)-5-fluorobenzyl) oxy)phenyl)butanoic acid Step 32a

Synthesis of methyl 4-(4-((2-(4-cyclopropylthiazol-5-yl)-5-fluorobenzyl)oxy)phenyl)butanoate The title compound was prepared in an analogous manner as step 1c of Example 1 involving the reaction of methyl 4-(4-((5-fluoro-2-(4,4,5,5-tetramethyl-1,3-dioxolan-2-yl) benzyl)oxy)phenyl)butanoate (compound of step 1a of Example 1) [100 mg, 0.232 mM] with 5-bromo-4-cyclopropylthiazole (71.5 mg, 0.350 mM), according to general procedure C (as described herein above). Yield: 57 mg, 0.134 mM, 57.4%; $^1$H NMR (300 MHz, CDCl$_3$) δ: 7.62-7.65 (m, 1H), 7.47-7.55 (m, 2H), 7.01-7.10 (m, 3H), 6.89 (d, J=8.4 Hz, 2H), 5.42 (s, 2H), 3.67 (s, 3H), 2.61 (t, J=7.2 Hz, 2H), 2.34 (t, J=7.5 Hz, 2H), 2.05-2.12 (m, 1H), 1.87-1.97 (m, 2H), 1.05-1.21 (m, 2H), 0.76-0.81 (m, 2H); LCMS m/z 425.9 [M+1].

Step 32b

Synthesis of 4-(4-((2-(4-cyclopropylthiazol-5-yl)-5-fluorobenzyl)oxy)phenyl)butanoic acid The title compound was prepared in an analogous manner as Example 1 involving the reaction of methyl 4-(4-((2-(4-cyclopropylthiazol-5-yl)-5-fluorobenzyl)oxy)phenyl)butanoate [50 mg, 0.118 m mol] with LiOH.H$_2$O [24.6 mg, 0.58 mM], according to general procedure D (as described herein above). Yield: 20 mg, 0.049 mM, 41.4%; $^1$H NMR (300 MHz, DMSO-d$_6$) δ: 12.02 (s, 1H), 8.97 (s, 1H), 7.45-7.45 (m, 1H), 7.30-7.31 (m, 2H), 6.98-7.07 (m, 2H), 6.79 (d, J=8.1 Hz, 1H), 6.72 (d, J=8.1 Hz, 1H), 4.90 (s, 2H), 2.49 (m, 2H), 2.14-2.16 (m, 2H), 1.69-1.745 (m, 3H), 0.87-1.23 (m, 4H); MS m/z 412.5 [M+1].

Example 33

4-(4-((2-(2,3-Dihydro-1H-inden-5-yl)benzyl)oxy) phenyl)butanoic acid

Step 33a

Synthesis of methyl 4-(4-((2-(2,3-dihydro-1H-inden-5-yl)benzyl)oxy)phenyl)butanoate The title compound was prepared in an analogous manner as step 12a of Example 12 involving the reaction of methyl-4-(4-((2-bromo-5-fluorobenzyl)oxy)phenyl)butanoate (compound of step 1a of Example 1) (70 mg, 0.171 mM) with (2,3-dihydro-1H-inden-5-yl)boronic acid (50.4 mg, 0.256 mM), according to general procedure C (as described herein above). Yield: 45 mg, 0.112 mM, 65.9%; $^1$H NMR (CDCl$_3$, 300 MHz) δ: 7.59-7.62 (m, 1H), 7.31-7.39 (m, 3H), 7.23-7.26 (m, 2H), 7.16 (d, J=8.1 Hz, 1H), 7.06 (d, J=8.1 Hz, 2H), 6.81 (d, J=8.1 Hz, 2H), 4.93 (s, 2H), 3.66 (s, 3H), 2.87-2.96 (m, 4H), 2.57 (t, J=7.5 Hz, 2H), 2.31 (t, J=7.5 Hz, 2H), 2.02-2.15 (m, 2H), 1.86-1.96 (m, 2H); MS m/z: 423.2 [M+Na].

Step 33b

Synthesis of 4-(4-((2-(2,3-dihydro-1H-inden-5-yl) benzyl)oxy)phenyl)butanoic acid The title compound was prepared in an analogous manner as Example 1 involving the reaction of methyl 4-(4-((2-(2, 3-dihydro-1H-inden-5-yl)benzyl)oxy)phenyl)butanoate [40 mg, 0.100 mM] with LiOH.H$_2$O (20.96 mg, 0.499 mM), according to general procedure D (as described herein above). Yield: 25 mg, 0.065 mM, 64.8%; $^1$H NMR (DMSO d$_6$, 300 MHz) δ 12.01 (s, 1H), 7.54-7.57 (m, 1H), 7.38-7.39 (m, 2H), 7.23-7.30 (m, 3H), 7.14 (d, J=7.8 Hz, 1H), 7.06 (d, J=8.4 Hz, 2H), 6.79 (d, J=8.4 Hz, 2H), 4.87 (s, 2H), 2.87 (m, 4H), 2.49 (m, 2H), 2.18 (t, J=7.2 Hz, 2H), 1.89-2.02 (m, 2H), 1.16-1.38 (m, 2H); MS m/z 409.0 [M+Na].

Example 34

4-(4-((5-Fluoro-2-(5-oxo-5,6,7,8-tetrahydronaphthalen-2-yl)benzyl)oxy)phenyl)butanoic acid Step 34a Synthesis of methyl 4-(4-((5-fluoro-2-(5-oxo-5,6,7,8-tetrahydronaphthalen-2-yl)benzyl)oxy)phenyl)butanoate The title compound was prepared in an analogous manner as step 1c of Example 1 involving the general procedure C (as described herein above), methyl 4-(4-((5-fluoro-2-(4,4,5,5-tetramethyl-1,3,2-dioxaborolan-2-yl)benzyl)oxy)phenyl)butanoate (150 mg, 0.35 mM) was coupled with 6-bromo-3,4-dihydronaphthalen-1(2H)-one (92 mg, 0.44 mM). Yield: 102 mg, 51.93%; $^1$H NMR (CDCl$_3$, 500 MHz): δ 8.07 (d, J=8.1 Hz, 1H), 7.39-7.35 (m, 1H), 7.31-7.28 (m, 2H), 7.26-7.24 (m, 1H), 7.13-7.04 (m, 3H) 6.78 (d, J=8.7 Hz, 2H), 4.86 (s, 2H), 3.66 (s, 3H), 2.92 (t, J=5.7, 6.0 Hz, 2H), 2.68 (t, J=6.9 Hz, 2H), 2.58 (t, J=7.8 Hz, 2H), 2.31 (t, J=7.5 Hz, 2H), 2.18-2.13 (m, 2H), 1.96-1.86 (m, 2H); MS (m/z): 469.2 [M+Na].

Step 34b

Synthesis of 4-(4-((5-fluoro-2-(5-oxo-5,6,7,8-tetrahydronaphthalen-2-yl)benzyl)oxy)phenyl)butanoic acid The title compound was prepared in an analogous manner as Example 1 involving the reaction of methyl 4-(4-((5-fluoro-2-(5-oxo-5,6,7,8-tetrahydronaphthalen-2-yl)benzyl)oxy)phenyl)butanoate (95 mg, 0.21 mM) with LiOH.H$_2$O (44.6 mg, 1.06 mM), according to general procedure D (as described herein above). Yield: 80 mg, 86.9%; $^1$H NMR (300 MHz, DMSO-d$_6$): δ 12.10 (br, m, 1H), 7.87 (d, J=8.7 Hz, 1H), 7.47-7.27 (m, 5H), 7.06 (d, J=8.4 Hz, 2H), 6.80 (d, J=8.7 Hz, 2H), 4.90 (s, 2H), 2.85 (t, J=5.4, 5.7 Hz, 2H), 2.58 (t, J=6.0, 6.3 Hz, 2H), 2.48-2.45 (m, 2H), 2.15 (t, J=7.2, 7.5 Hz, 2H), 2.02-1.97 (m, 2H), 1.76-1.69 (m, 2H); MS (m/z) 455.1 [M+Na].

Example 35

4-(4-((2-(7,8-Dihydronaphthalen-2-yl)-5-fluorobenzyl)oxy)phenyl)butanoic acid

Step 35a

Synthesis of methyl 4-(4-((2-(7,8-dihydronaphthalen-2-yl)-5-fluorobenzyl)oxy)phenyl)butanoate The title compound was prepared in an analogous manner as step 1c of Example 1 involving the general procedure C (as described herein above) by using methyl 4-(4-((5-fluoro-2-(4,4,5,5-tetramethyl-1,3,2-dioxaborolan-2-yl)benzyl)oxy)phenyl)butanoate (150 mg, 0.35 mM) with 7-bromo-1,2-dihydronaphthalene (49 mg, 0.23 mM). Yield: 51 mg, 50.8%; $^1$H NMR (300 MHz, CDCl$_3$): δ 7.37 (d, J=9.5 Hz, 1H), 7.31-7.28 (m, 1H), 7.14 (d, J=7.5 Hz, 1H), 7.09-7.06 (m, 5H), 6.81 (d, J=8.5 Hz, 2H), 6.52 (d, J=8.5 Hz, 1H), 6.09-6.06 (m, 1H), 4.93 (s, 2H), 3.67 (s, 3H), 2.79 (t, J=8.0 Hz, 2H), 2.59 (t, J=7.5 Hz, 2H), 2.34-2.31 (m, 4H), 1.95-1.89 (m, 2H), MS (m/z) 453.2 [M+Na].

Step 35b

Synthesis of 4-(4-((2-(7,8-dihydronaphthalen-2-yl)-5-fluorobenzyl)oxy)phenyl)butanoic acid The title compound was prepared in an analogous manner as Example 1 involving the reaction of methyl 4-(4-((2-(7,8-dihydronaphthalen-2-yl)-5-fluorobenzyl)oxy)phenyl)butanoate (45 mg, 0.10 mM) with LiOH.H$_2$O (21.9 mg, 0.52 mM), according to general procedure D (as described herein above). Yield: 35 mg, 80.4%; $^1$H NMR (500 MHz, DMSO-d$_6$): δ 12.03 (br, m, 1H), 7.43-7.36 (m, 2H), 7.28-7.25 (m, 1H), 7.18-7.14 (m, 2H), 7.09-7.06 (m, 3H), 6.82 (d, J=8.0 Hz, 2H), 6.52 (d, J=9.5 Hz, 1H), 6.07-6.05 (m, 1H), 4.91 (s, 2H), 2.68 (t, J=8.5, 8.0 Hz, 2H), 2.47-2.50 (m, 2H), 2.23-2.24 (m, 2H), 2.17 (t, J=7.0, 7.5 Hz, 2H), 1.75-1.72 (m, 2H); MS (m/z) 439.2 [M+Na].

Example 36

4-(4-((5-Fluoro-2-(5-methylene-5,6,7,8-tetrahydronaphthalen-2-yl)benzyl)oxy)phenyl)butanoic acid Step 36a Synthesis of methyl 4-(4-((5-fluoro-2-(5-methylene-5,6,7,8-tetrahydronaphthalen-2-yl)benzyl)oxy)phenyl)butanoate The title compound was prepared in an analogous manner as step 1c of Example 1 involving the reaction of methyl 4-(4-((5-fluoro-2-(4,4,5,5-tetramethyl-1,3,2-dioxaborolan-2-yl)benzyl)oxy)phenyl)butanoate (150 mg, 0.35 mM) with 6-bromo-1-methylene-1,2,3,4-tetrahydronaphthalene (51 mg, 0.23 mM), general procedure C (as described herein above). Yield: 90 mg, 89.0%); $^1$H NMR (500 MHz, CDCl$_3$): δ 7.70 (d, J=8.5 Hz, 1H), 7.37 (d, J=9.5 Hz, 1H), 7.31-7.28 (m, 1H), 7.15 (d, J=8.0 Hz, 1H), 7.08 (t, J=8.0 Hz, 4H), 6.81 (d, J=8.0 Hz, 2H), 5.57 (s, 1H), 5.01 (s, 1H), 4.93 (s, 2H), 3.67 (s, 3H), 2.83 (t, J=6.0 Hz, 2H), 2.61-2.58 (m, 4H), 2.32 (t, J=7.5 Hz, 2H), 1.95-1.89 (m, 4H); MS (m/z) 445.2 [M+H].

Step 36b

Synthesis of 4-(4-((5-fluoro-2-(5-methylene-5,6,7,8-tetrahydronaphthalen-2-yl)benzyl)oxy)phenyl)butanoic acid The title compound was prepared in an analogous manner as Example 1 involving the reaction of methyl 4-(4-((5-fluoro-2-(5-methylene-5,6,7,8-tetrahydronaphthalen-2-yl)benzyl)oxy)phenyl)butanoate (80 mg, 0.18 mM) with LiOH.H$_2$O (37.7 mg, 0.89 mM), according to general procedure D (as described herein above). Yield: 65 mg, 83.9%; $^1$H NMR (500 MHz, DMSO-d$_6$): δ 12.03 (br m, 1H), 7.71 (d, J=8.0 Hz, 1H), 7.43-7.36 (m, 2H), 7.29-7.26 (m, 1H), 7.20-7.11 (m, 2H), 7.08 (d, J=8.5 Hz, 2H), 6.83 (d, J=8.0 Hz, 2H), 5.57 (s, 1H), 4.98 (s, 1H), 4.91 (s, 2H), 2.72 (t, J=6.0

Hz, 2H), 2.47-2.50 (m, 4H), 2.17 (t, J=7.0, 7.5 Hz, 2H), 1.76-1.72 (m, 4H); MS (m/z) 431.2 [M+H].

Example 37

4-(4-(5-Fluoro-2-(5-methyl-7,8-dihydronaphthalen-2-yl)benzyl)oxy)phenyl)butanoic acid Step 37a Synthesis of 6-bromo-1-methyl-1,2,3,4-tetrahydronaphthalen-1-ol To a stirred solution of 6-bromo-3,4-dihydronaphthalen-1(2H)-one (200 mg, 0.89 mM) in THF (5 ml) at 0° C., MeMgBr (954 mg, 8.0 mM) was added and the reaction mixture was allowed to stir at RT for 5 h. The reaction mixture was quenched with saturated ammonium chloride solution, extracted with ethyl acetate, dried over anhydrous sodium sulphate and concentrated. It was further purified to give the title compound. Yield: 51.3%; $^1$H NMR (DMSO, 300 MHz): δ 7.46 (d, J=8.4 Hz, 1H), 7.32-7.29 (m, 1H), 7.23 (s, 1H), 4.94 (s, 1H), 2.68-2.66 (m, 2H), 1.78-1.67 (m, 4H), 1.34 (s, 3H); MS (e/z): 242.1 [M+H].

Step 37b

Synthesis of 7-bromo-4-methyl-1,2-dihydronaphthalene

To a stirred solution of 6-bromo-1-methyl-1,2,3,4-tetrahydronaphthalen-1-ol (110 mg, 0.45 mM) in benzene (5 ml), PTSA (3.47 mg, 0.018 mM) was added and the reaction mixture was allowed to reflux for 1.5 h with azeotropic removal of water using Dean-Stark apparatus. The reaction mixture was cooled to RT, then water (4.5 ml) was added, organic layer was separated washed with saturated sodium bicarbonate solution, dried over anhydrous sodium sulphate and concentrated. It was further purified to give the title compound. Yield: 80 mg, 78.66%; $^1$H NMR (CDCl$_3$, 300 MHz): δ 7.33-7.30 (m, 2H), 7.09 (d, J=8.4 Hz, 1H), 5.86-5.87 (m, 1H), 2.74 (t, J=7.8 Hz, 2H), 2.24-2.18 (m, 2H), 2.03 (d, J=1.5 Hz, 3H); MS (e/z) 246.6 [M+Na].

Step 37c

Synthesis of methyl 4-(4-((5-fluoro-2-(5-methyl-7,8-dihydronaphthalene-2-yl)benzyl)oxy)phenyl)butanoate The title compound was prepared in an analogous manner as step 1c of Example 1 involving the reaction of methyl 4-(4-((5-fluoro-2-(4,4,5,5-tetramethyl-1,3,2-dioxaborolan-2-yl)benzyl)oxy)phenyl)butanoate (115 mg, 0.27 mM) with 7-bromo-4-methyl-1,2-dihydronaphthalene (40 mg, 0.18 mM) as per the general procedure C (as described herein above). Yield: 55 mg (69.0%); $^1$H NMR (300 MHz, CDCl$_3$): δ 7.37-7.29 (m, 2H), 7.27-7.24 (m, 1H), 7.18-7.16 (m, 1H), 7.11-7.04 (m, 4H), 6.81 (d, J=8.4 Hz, 2H), 5.88-5.89 (m, 1H), 4.93 (s, 2H), 3.66 (s, 3H), 2.74 (t, J=8.1 Hz, 2H), 2.58 (t, J=7.5 Hz, 2H), 2.33-2.28 (m, 4H), 2.08 (s, 3H), 1.96-1.88 (m, 2H); MS (m/z) 445.2 [M+H].

Step 37d

Synthesis of 4-(4-((5-fluoro-2-(5-methyl-7,8-dihydronaphthalen-2-yl)benzyl)oxy)phenyl)butanoic acid The title compound was prepared in an analogous manner as Example 1 involving the reaction of methyl 4-(4-((5-fluoro-2-(5-methyl-7,8-dihydronaphthalene-2-yl)benzyl)oxy)phenyl)butanoate (50 mg, 0.11 mM) with LiOH.H$_2$O (23.6 mg, 0.56 mM), according to general procedure D (as described herein above). Yield: 44 mg, 90.9%; $^1$H NMR (300 MHz, DMSO-d$_6$): δ 12.03 (br m, 1H), 7.43-7.35 (m, 2H), 7.29-7.22 (m, 3H), 7.17 (s, 1H), 7.07 (d, J=8.7 Hz, 2H), 6.82 (d, J=8.7 Hz, 2H), 5.85-5.86 (m, 1H), 4.90 (s, 2H), 2.62 (t, J=7.8, 8.1 Hz, 2H), 2.47-2.52 (m, 2H), 2.16 (t, J=7.2 Hz, 4H), 2.00 (s, 3H), 1.77-1.69 (m, 2H); MS (m/z) 431.2 [M+H].

Example 38

4-(4-((5-Fluoro-2-(5-methoxy-5,6,7,8-tetrahydronaphthalen-2-yl)benzyl)oxy)phenyl)butanoic acid Step 38a Synthesis of 6-bromo-1-methoxy-1,2,3,4-tetrahydronaphthalene To a stirred suspension of NaH (11.51 mg, 0.480 mM) (60% in mineral oil) in THF (3 ml) at 0° C., 6-bromo-1,2,3,4-tetrahydronaphthalen-1-ol (90 mg, 0.396 mM) in THF (3 ml) was added and the reaction mixture was allowed to stir at 0° C. for 30 min. Then, MeI (0.030 ml, 0.480 mM) was added and the reaction mixture was allowed to stir at 0° C. for 1 h and RT for 2 h. After the completion of the reaction, the reaction mixture was quenched with ice cubes and concentrated. It was dissolved in ethyl acetate and washed with water dried over anhydrous sodium sulphate and concentrated. It was further purified to give the title compound. Yield: 70 mg, 73.29%; $^1$H NMR (CDCl$_3$, 300 MHz): δ 7.31-7.28 (m, 1H), 7.26-7.21 (m, 2H), 4.26 (t, J=4.2 Hz, 1H), 3.43 (s, 3H), 2.83-2.63 (m, 2H), 2.02-1.82 (m, 3H), 1.76-1.69 (m, 1H). MS (e/z): 242.1 [M+H].

Step 38b

Synthesis of methyl 4-(4-((5-fluoro-2-(5-methoxy-5,6,7,8-tetrahydronaphthalen-2-yl)benzyl)oxy)phenyl)butanoate The title compound was prepared in an analogous manner as step 1c of Example 1 involving the reaction of methyl 4-(4-((5-fluoro-2-(4,4,5,5-tetramethyl-1,3,2-dioxaborolan-2-yl)benzyl)oxy)phenyl)butanoate (213 mg, 0.49 mM) with 6-bromo-1-methoxy-1,2,3,4-tetrahydronaphthalene (80 mg, 0.33 mM). Yield: 90 mg, 58.6%. $^1$H NMR (300 MHz, CDCl$_3$): δ 7.41-7.32 (m, 2H), 7.25-7.23 (m, 1H), 7.16-7.14 (m, 1H), 7.07-7.04 (m, 4H), 6.79 (d, J=8.7 Hz, 2H), 4.90 (s, 2H), 4.33-4.35 (m, 1H), 3.66 (s, 3H), 3.48 (s, 3H), 2.83-2.69 (m, 2H), 2.57 (t, J=7.5 Hz, 2H), 2.31 (t, J=7.5 Hz, 2H), 2.01-1.95 (m, 2H), 1.93-1.86 (m, 3H), 1.77-1.73 (m, 1H); MS (m/z) 485.5 [M+Na].

Step 38c

Synthesis of 4-(4-((5-fluoro-2-(5-methoxy-5,6,7,8-tetrahydronaphthalen-2-yl)benzyl)oxy)phenyl)butanoic acid The title compound was prepared in an analogous manner as Example 1 involving the reaction of methyl-4-(4-((5-fluoro-2-(5-methoxy-5,6,7,8-tetrahydronaphthalen-2-yl)benzyl)oxy)phenyl)butanoate (80 mg, 0.16 mM) with LiOH.H$_2$O (36.3 mg, 0.86 mM), according to general procedure D (as described herein above). Yield: 63 mg, 81.2%; $^1$H NMR (300 MHz, DMSO-d$_6$) δ: 12.03 (br m, 1H), 7.42-7.22 (m, 4H), 7.17-7.15 (m, 1H), 7.09-7.04 (m, 3H), 6.81 (d, J=8.4 Hz, 2H), 4.87 (s, 2H), 4.25-4.26 (m, 1H), 3.32 (s, 3H), 2.63-2.59 (m, 2H), 2.48-2.45 (m, 2H), 2.15 (t, J=7.2, 7.5 Hz, 2H), 1.89-1.63 (m, 6H); MS (m/z) 471.1 [M+Na].

Example 39

4-(4-((5-Fluoro-2-(5-methoxy-5-methyl-5,6,7,8-tetrahydronaphthalen-2-yl)benzyl)oxy)phenyl)butanoic acid Step 39a Synthesis of 6-bromo-1-methoxy-1-methyl-1,2,3,4-tetrahydronaphthalene To a stirred suspension of NaH (11.94 mg, 0.498 mM) in dry THF (5 ml) at 0° C. under nitrogen was added 6-bromo-1-methyl-1,2,3,4-tetrahydronaphthalen-1-ol (100 mg, 0.415 mM) in THF and the reaction mixture was allowed to stir at 0° C. for 0.5 h. Then MeI (0.031 ml, 0.498 mM) was added dropwise and the reaction mixture was allowed to stir at RT for 2 h. After the completion of the reaction, the reaction mixture was quenched with ice-cubes and concentrated, extracted with ethyl acetate and washed with water, brine dried over anhydrous sodium sulphate and concentrated. Then it was purified to give the title compound. Yield: 41 mg 38.75%; $^1$H NMR (CDCl$_3$, 300 MHz): δ 7.31-7.32 (m, 2H), 7.23 (s, 1H), 3.06 (s, 3H), 2.83-2.66 (m, 2H), 2.16-2.08 (m, 1H), 1.95-1.92 (m, 1H), 1.85-1.70 (m, 2H), 1.46 (s, 3H); MS (e/z): 254.1 [M−H].

Step 39b

Synthesis of methyl 4-(4-((5-fluoro-2-(5-methoxy-5-methyl-5,6,7,8-tetrahydronaphthalen-2-yl)benzyl)oxy)phenyl)butanoate The title compound was prepared in an analogous manner as step 1c of Example 1 involving the reaction of methyl 4-(4-((5-fluoro-2-(4,4,5,5-tetramethyl-1,3,2-dioxaborolan-2-yl)benzyl)oxy)phenyl)butanoate (88 mg, 0.20 mM) with 6-bromo-1-methoxy-1-methyl-1,2,3,4-tetrahydronaphthalene (35 mg, 0.14 mM). Yield: 48 mg, 72.9%; $^1$H NMR (CDCl$_3$, 300 MHz): δ 7.49 (d, J=7.8 Hz, 1H), 7.36-7.27 (m, 2H), 7.17-7.14 (m, 1H), 7.09-7.04 (m, 4H), 6.79 (d, J=8.7 Hz, 2H), 4.92 (s, 2H), 3.66 (s, 3H), 3.12 (s, 3H), 2.76-2.71 (m, 2H), 2.58 (t, J=7.8 Hz, 2H), 2.31 (t, J=7.5 Hz, 2H), 2.20-2.16 (m, 1H), 1.96-1.86 (m, 3H), 1.79-1.76 (m, 2H), 1.53 (s, 3H); MS (m/z) 499.6 [M+Na].

Step 39c

Synthesis of 4-(4-((5-fluoro-2-(5-methoxy-5-methyl-5,6,7,8-tetrahydronaphthalen-2-yl)benzyl)oxy)phenyl)butanoic acid The title compound was prepared in an analogous manner as Example 1 involving the reaction of methyl 4-(4-((5-fluoro-2-(5-methoxy-5-methyl-5,6,7,8-tetrahydronaphthalen-2-yl)benzyl)oxy)phenyl)butanoate (40 mg, 0.084 mM) with LiOH.H$_2$O 17.5 mg, 0.41 mM), according to general procedure D (as described herein above), to give 4-(4-((5-fluoro-2-(5-methoxy-5-methyl-5,6,7,8-tetrahydronaphthalen-2-yl)benzyl)oxy)phenyl)butanoic acid. Yield: 32 mg, 82.4%; $^1$H NMR (500 MHz, DMSO-d$_6$) δ 11.88 (br m, 1H), 7.42-7.36 (m, 3H), 7.28-7.25 (m, 1H), 7.21 (d, J=7.5 Hz, 1H), 7.09 (s, 1H), 7.07 (d, T=8.5 Hz, 2H), 6.79 (d, J=8.5 Hz, 2H), 4.90 (s, 2H), 2.94 (s, 3H), 2.65-2.58 (m, 2H), 2.50-2.48 (m, 2H), 2.17 (t, J=7.5 Hz, 2H), 2.07-2.02 (m, 1H), 1.83-1.85 (m, 1H), 1.76-1.70 (m, 3H), 1.66-1.62 (m, 1H), 1.40 (s, 3H); MS (m/z): 485.5 [M+Na].

Example 40

4-(4-((5-Fluoro-2-(5-(1-methylcyclopropyl)thiophen-2-yl)benzyl)oxy)phenyl)butanoic acid Step 40a Synthesis of 2-bromo-5-(prop-1-en-2-yl)thiophene To a stirred suspension of methyltriphenylphosphonium bromide (6.27 g, 17.55 mM) in THF (60 ml) at −78° C., n-butyllithium (10.97 ml, 17.55 mM) was added dropwise. The reaction mixture was allow to stir at RT for 2 h, then a solution of 1-(5-bromothiophen-2-yl)ethanone (3.0 g, 14.63 mM) in THF was added and allowed for stirring for overnight. The reaction mixture was quenched with saturated ammonium chloride solution extracted with ethyl acetate, organic layer was washed with brine solution, dried, concentrated and purified by column to give the title compound. Yield: 2.1 g, 10.34 mM, 70.7%; $^1$H NMR (CDCl$_3$, 500 MHz) δ 6.94 (d, J=4.0 Hz, 1H), 6.78 (d, J=3.5 Hz, 1H), 5.29 (s, 1H), 4.97 (s, 1H), 2.11 (s, 3H); MS (e/z) 204.1 [M+H].

Step 40b

Synthesis of 2-bromo-5-(1-methylcyclopropyl)thiophene

To a stirred solution of diethylzinc (6.40 ml, 6.40 mM) in DCM at 0° C., TFA (0.493 ml, 6.40 mM) was slowly added and the mixture was allowed to stir for 20 min. Then, diiodomethane (0.516 ml, 6.40 mM) was added and stirred for 20 min. A solution of 2-bromo-5-(prop-1-en-2-yl)thiophene (0.650 g, 3.20 mM) in DCM was added and the reaction mixture was stirred for overnight. Then, the reaction mixture was washed with saturated sodium bicarbonate solution, brine solution, dried over Na$_2$SO$_4$, concentrated and purified to give the title compound. Yield: 0.564 g, 2.60 mM, 81%; $^1$H NMR (CDCl$_3$, 300 MHz) δ 6.81 (d, J=3.90 Hz, 1H), 6.51 (d, J=3.6 Hz, 1H), 1.43 (s, 3H), 0.87-0.92 (m, 2H), 0.79-0.84 (m, 2H).

Step 40c

Synthesis of methyl 4-(4-((5-fluoro-2-(5-(1-methylcyclopropyl)thiophen-2-yl)benzyl)oxy)phenyl)butanoate The title compound was prepared in an analogous manner as step 1c of Example 1 involving the reaction of 2-bromo-5-(1-methylcyclopropyl)thiophene (0.051 g, 0.235 mM), methyl 4-(4-((5-fluoro-2-(4,4,5,5-tetramethyl-1,3,2-dioxaborolan-2-yl)benzyl)oxy)phenyl)butanoate (0.150 g, 0.350 mM), and K$_2$CO$_3$ (0.097 g, 0.700 mM) in presence of tetrakis(triphenylphosphine)palladium(0) (0.013 g, 0.012 mM) according to general procedure C (as described herein above). Yield: 0.084 g, 0.192 mM, 82%; $^1$H NMR (CDCl$_3$, 300 MHz) δ 7.32-7.42 (m, 2H), 7.03-7.10 (m, 3H), 6.82-6.85 (m, 3H), 6.70 (d, J=3.3 Hz, 1H), 5.05 (s, 2H), 3.66 (s, 3H), 2.59 (t, J=7.2 Hz, 2H), 2.32 (t, J=7.5 Hz, 2H), 1.90-1.95 (m, 2H), 1.49 (s, 3H), 0.90-1.00 (m, 2H), 0.80-0.90 (m, 2H); MS m/z 438.4 [M$^+$].

Step 40d

Synthesis of 4-(4-((5-fluoro-2-(5-(1-methylcyclopropyl)thiophen-2-yl)benzyl)oxy)phenyl)butanoic acid The title compound was prepared in an analogous manner as Example 1 involving the reaction of methyl 4-(4-((5-fluoro-2-(5-(1-methylcyclopropyl)thiophen-2-yl)benzyl)oxy)phenyl)butanoate (0.075 g, 0.171 mM) with LiOH.H$_2$O (0.036 g, 0.855 mM), according to general procedure D (as described herein above). Yield: 0.056 g, 0.132 mM, 77%; $^1$H NMR (300 MHz, DMSO-d$_6$) δ 12.03 (s, 1H), 7.40-7.52 (m, 2H), 7.09 (d, J=8.1 Hz, 2H), 6.96 (bs, 1H), 6.8 (d, J=8.4 Hz, 2H), 6.79 (d, J=3.6 Hz, 1H), 5.01 (s, 2H), 2.40-2.55 (m, 2H), 2.18 (t, J=7.2 Hz, 2H), 1.71-1.76 (m, 2H), 1.40 (s, 3H), 0.86 (s, 4H); MS: m/z 425.5 [M+H$^+$].

Example 41

4-(4-((5-Fluoro-2-(5,6,7,8-tetrahydro-4H-cyclohepta[d]thiazol-2-yl)benzyl)oxy)phenyl)butanoic acid Step 41a

Synthesis of methyl 4-(4-((5-fluoro-2-(5,6,7,8-tetrahydro-4H-cyclohepta[d]thiazol-2-yl)benzyl)oxy)phenyl)butanoate The title compound was prepared in an analogous manner as step 1c of Example 1 involving the reaction of 2-bromo-5,6,7,8-tetrahydro-4H-cyclohepta[d]thiazole (0.072 g, 0.311 mM), methyl 4-(4-((5-fluoro-2-(4,4,5,5-tetramethyl-1,3,2-dioxaborolan-2-yl)benzyl)oxy)phenyl)butanoate (0.200 g, 0.467 mM), K$_2$CO$_3$ (0.129 g, 0.934 mM), in presence of tetrakis(triphenylphosphine)palladium(0) (0.018 g, 0.016 mM) according to general procedure C (as described herein above). Yield: 0.106 g, 0.234 mM, 75%; $^1$H NMR (500 MHz, CDCl$_3$) δ 7.63-7.66 (m, 1H), 7.46 (d, J=10.0 Hz, 1H), 7.10 (d, J=8.5 Hz, 2H), 7.02-7.05 (m, 1H), 6.88 (d, J=8.0 Hz, 2H), 5.44 (s, 2H), 3.68 (s, 3H), 2.99-3.01 (m, 2H), 2.86-2.88 (m, 2H), 2.60 (t, J=10.5 Hz, 2H), 2.33 (t, J=10.5 Hz, 2H), 1.89-1.97 (m, 4H), 1.73-1.79 (m, 4H); MS, m/z 454.6 [M+H$^+$].

Step 41b

Synthesis of 4-(4-((5-fluoro-2-(5,6,7,8-tetrahydro-4H-cyclohepta[d]thiazol-2-yl)benzyl)oxy)phenyl)butanoic acid The title compound was prepared in an analogous manner as Example 1 involving the reaction of methyl 4-(4-((5-fluoro-2-(5,6,7,8-tetrahydro-4H-cyclohepta[d]thiazol-2-yl)benzyl)oxy)phenyl)butanoate (0.096 g, 0.212 mM) with LiOH.H$_2$O (0.044 g, 1.058 mM), according to general procedure D (as described herein above). Yield: 0.083 g, 0.189 mM, 89%; $^1$H NMR (300 MHz, DMSO-d$_6$) δ: 12.03 (s, 1H), 7.73-7.78 (m, 1H), 7.45 (d, J=9.9 Hz, 1H), 7.25-7.30 (m, 1H), 7.09 (d, J=7.2 Hz, 2H), 6.85 (d, J=8.4 Hz, 2H), 5.38 (s, 2H), 2.70-7.90 (m, 4H), 2.40-2.60 (m, 2H), 2.15-2.19 (m, 2H), 1.40-1.90 (m, 8H); MS: m/z 440.5 [M+H$^+$].

Example 42

4-(4-((5-Fluoro-2-(5-(1-fluorocyclopropyl)thiophen-2-yl)benzyl)oxy)phenyl)butanoic acid Step 42a

Synthesis of 1-(5-bromothiophen-2-yl)cyclopropanol

To a stirred solution of ethyl 5-bromothiophene-2-carboxylate (1 g, 4.25 mM) and titanium(iv) isopropoxide (0.312 ml, 1.063 mM) in diethyl ether (20 ml), ethylmagnesium bromide (10.63 ml, 10.63 mM) solution was added at RT and stirred for overnight. The reaction mixture was quenched with saturated ammonium chloride solution, extracted with ethyl acetate, organic layer washed with brine solution, dried, concentrated and purified by combiflash to give the title compound. Yield: 0.18 g, 0.822 mM, 19.31%; $^1$H NMR (CDCl$_3$, 500 MHz) δ 6.88 (d, J=4.0 Hz, 1H), 6.62 (d, J=3.5 Hz, 1H), 2.59 (s, 1H), 1.25-1.31 (m, 2H), 1.04-1.10 (m, 2H); MS e/z 220.1 [M+H].

Step 42b

Synthesis of 2-bromo-5-(1-fluorocyclopropyl)thiophene

To a stirred solution of 1-(5-bromothiophen-2-yl)cyclopropanol (0.150 g, 0.685 mM) in CH$_2$Cl$_2$ (5 ml) at −78° C., Diethylaminosulfur trifluoride (DAST) was added slowly (0.090 ml, 0.685 mM) and stirred for 2 h. The reaction mixture was washed with sodium bicarbonate solution, dried, concentrated and purified to give the title compound. Yield: 0.041 g, 0.185 mM, 27.1%; $^1$H NMR (CDCl$_3$, 300 MHz) δ 6.83 (d, J=3.90 Hz, 1H), 6.61 (d, J=3.6 Hz, 1H), 1.77-1.21 (m, 2H), 0.86-0.90 (m, 2H); MS (e/z) 244.1 [M+Na].

Step 42c

Synthesis of methyl 4-(4-((5-fluoro-2-(5-(1-fluorocyclopropyl)thiophen-2-yl)benzyl)oxy)phenyl)butanoate The title compound was prepared in an analogous manner as step 1c of Example 1 involving the reaction of methyl 4-(4-((5-fluoro-2-(4,4,5,5-tetramethyl-1,3,2-dioxaborolan-2-yl)benzyl)oxy)phenyl)butanoate (0.174 g, 0.407 mM), 2-bromo-5-(1-fluorocyclopropyl)thiophene (0.06 g, 0.40 mM), K$_2$CO$_3$ (0.113 g, 0.814 mM) in presence of tetrakis(triphenylphosphine)palladium(0) (0.016 g, 0.014 mM) according to general procedure C (as described herein above). Yield: 0.082 g, 0.185 mM, 68.3%; $^1$H NMR (CDCl$_3$, 500 MHz) δ 7.32-7.38 (m, 2H), 7.07 (d, J=8.5 Hz, 2H), 7.01-7.03 (m, 1H), 6.80-6.81 (m, 4H), 4.98 (s, 2H), 3.67 (s, 3H), 2.59 (t, J=7.5 Hz, 2H), 2.32 (t, J=7.5 Hz, 2H), 1.89-1.95 (m, 2H), 1.28-1.30 (m, 2H), 0.95-0.98 (m, 2H); MS, m/z 465.4 [M+Na].

Step 42d

Synthesis of 4-(4-((5-fluoro-2-(5-(1-fluorocyclopropyl)thiophen-2-yl)benzyl)oxy)phenyl)butanoic acid The title compound was prepared in an analogous manner as Example 1 involving the reaction of methyl 4-(4-((5-fluoro-2-(5-(1-fluorocyclopropyl)thiophen-2-yl)benzyl)oxy)phenyl)butanoate (0.070 g, 0.158 mM) with LiOH.H$_2$O (0.033 g, 0.791 mM), according to general procedure D (as described herein above). Yield: 0.045 g, 0.105 mM, 66.4%; $^1$H NMR (300 MHz, DMSO-d$_6$) δ: 12.03 (s, 1H), 7.40-7.42 (m, 2H), 7.19-7.24 (m, 1H), 7.05 (d, J=8.1 Hz, 2H), 6.90 (d, J=3.6 Hz, 1H), 6.75-7.85 (m, 3H), 4.92 (s, 2H), 2.40-2.55 (m, 2H), 2.16 (t, J=7.2 Hz, 2H), 1.65-1.80 (m, 2H), 1.15-1.25 (m, 2H), 0.08-0.090 (m, 2H); MS: m/z 428.5 [M$^+$].

Example 43

4-(4-((4'-(2,2-Difluorocyclopropyl)-4-fluoro-[1,1'-biphenyl]-2-yl)methoxy)phenyl)butanoic acid Step 43a

Synthesis of methyl 4-(4-((4'-(2,2-difluorocyclopropyl)-4-fluoro-[1,1'-biphenyl]-2-yl)methoxy)phenyl)butanoate The title compound was prepared in an analogous manner as step 1c of Example 1 involving the reaction of 1-bromo- 4-(2,2-difluorocyclopropyl)benzene (0.054 g, 0.233 mM), methyl 4-(4-((5-fluoro-2-(4,4,5,5-tetramethyl-1,3,2-dioxaborolan-2-yl)benzyl)oxy)phenyl)butanoate (0.150 g, 0.350 mM), $K_2CO_3$ (0.097 g, 0.700 mM) in presence of tetrakis(triphenylphosphine)palladium(0) (0.013 g, 0.012 mM) according to general procedure C (as described herein above). Yield: 0.084 g, 0.185 mM, 79%; $^1$H NMR (300 MHz, CDCl$_3$) δ 7.25-7.37 (m, 6H), 7.04-7.11 (m, 3H), 6.78 (d, J=8.4 Hz, 2H), 4.88 (s, 2H), 3.66 (s, 3H), 2.73-2.84 (m, 1H), 2.58 (t, J=7.2 Hz, 2H), 2.31 (t, J=7.5 Hz, 2H), 1.80-1.96 (m, 3H), 1.61-1.72 (m, 1H); MS, m/z 478.4 [M+Na$^+$].

Step 43b

Synthesis of 4-(4-((4'-(2,2-difluorocyclopropyl)-4-fluoro-[1,1'-biphenyl]-2-yl)methoxy)phenyl)butanoic acid The title compound was prepared in an analogous manner as Example 1 involving the reaction of methyl 4-(4-((4'-(2,2-difluorocyclopropyl)-4-fluoro-[1,1'-biphenyl]-2-yl)methoxy)phenyl)butanoate (0.070 g, 0.154 mM) with LiOH.H$_2$O (0.032 g, 0.770 mM), according to general procedure D (as described herein above). Yield: 0.062 g, 0.141 mM, 91%; $^1$H NMR (300 MHz, DMSO-d$_6$) δ 12.02 (s, 1H), 7.31-7.45 (m, 6H), 7.26-7.29 (m, 1H), 7.07 (d, J=8.5 Hz, 2H), 6.80 (d, J=8.5 Hz, 2H), 4.91 (s, 2H), 3.01-3.08 (m, 1H), 2.45-2.55 (m, 2H), 2.18 (t, J=7.0 Hz, 2H), 1.91-2.01 (m, 2H), 1.70-1.76 (m, 2H); MS, m/z 463.2 [M+Na$^+$].

Example 44

4-(4-((2-(5-Cyclopropyl-1,3,4-thiadiazol-2-yl)-5-fluorobenzyl)oxy)phenyl)butanoic acid Step 44a Synthesis of methyl 4-(4-((2-(5-cyclopropyl-1,3,4-thiadiazol-2-yl)-5-fluorobenzyl)oxy)phenyl)butanoate The title compound was prepared in an analogous manner as step 1c of Example 1 involving the reaction of 2-bromo-5-cyclopropyl-1,3,4-thiadiazole (0.048 g, 0.233 mM), methyl 4-(4-((5-fluoro-2-(4,4,5,5-tetramethyl-1,3,2-dioxaborolan-2-yl)benzyl)oxy)phenyl)butanoate (0.150 g, 0.350 mM), $K_2CO_3$ (0.097 g, 0.700 mM) in presence of tetrakis(triphenylphosphine)palladium(0) (0.233 mM) according to general procedure C (as described herein above). Yield: 0.064 g, 0.150 mM, 64.3%; $^1$H NMR (300 MHz, CDCl$_3$) δ 7.56-7.64 (m, 2H), 7.05-7.15 (m, 3H), 6.90 (d, J=8.4 Hz, 2H), 5.42 (s, 2H), 3.67 (s, 3H), 2.59 (t, J=7.5 Hz, 2H), 2.40-2.44 (m, 1H), 2.32 (t, J=7.5 Hz, 2H), 1.87-1.97 (m, 2H), 1.22-1.29 (m, 4H); MS, m/z 427.4 [M+H$^+$].

Step 44b

Synthesis of 4-(4-((2-(5-cyclopropyl-1,3,4-thiadiazol-2-yl)-5-fluorobenzyl)oxy)phenyl)butanoic acid The title compound was prepared in an analogous manner as Example 1 involving the reaction of methyl 4-(4-((2-(5-cyclopropyl-1,3,4-thiadiazol-2-yl)-5-fluorobenzyl)oxy)phenyl)butanoate (0.053 g, 0.124 mM) with LiOH.H$_2$O (0.026 g, 0.621 mM), according to general procedure D (as described herein above). Yield: 0.039 g, 0.095 mM, 76%; $^1$H NMR (300 MHz, DMSO-d$_6$) δ 12.02 (s, 1H), 7.77-7.82 (m, 1H), 7.50-7.60 (m, 1H), 7.31-7.41 (m, 1H), 7.09 (d, J=8.1 Hz, 2H), 6.86 (d, J=8.4 Hz, 2H), 5.30 (s, 2H), 2.40-2.60 (m, 3H), 2.18 (t, J=7.2 Hz, 2H), 1.65-1.80 (m, 2H), 1.20-1.30 (m, 2H), 0.95-1.05 (m, 2H); MS, m/z 413.5 [M+H$^+$].

Example 45

4-(4-((2-(5-Cyclopropylthiazol-2-yl)-5-fluorobenzyl)oxy)phenyl)butanoic acid

Step 45a

Synthesis of methyl 4-(4-((2-(5-cyclopropylthiazol-2-yl)-5-fluorobenzyl)oxy)phenyl)butanoate The title compound was prepared in an analogous manner as step 1c of Example 1 involving the reaction of 2-bromo-5-cyclopropylthiazole (0.032 g, 0.156 mM), methyl 4-(4-((5-fluoro-2-(4,4,5,5-tetramethyl-1,3,2-dioxaborolan-2-yl)benzyl)oxy)phenyl)butanoate (0.100 g, 0.233 mM), potassium carbonate (0.065 g, 0.467 mM) in presence of tetrakis(triphenylphosphine)palladium(0) (8.99 mg, 7.78 μmol) according to general procedure C (as described herein above). Yield: 0.058 g, 0.136 mM, 88%; $^1$H NMR (CDCl$_3$, 300 MHz) δ 7.60-7.65 (m, 1H), 7.55 (s, 1H), 7.01-7.09 (m, 3H), 6.88 (d, J=8.4 Hz, 2H), 5.42 (s, 2H), 3.66 (s, 3H), 2.59 (t, J=7.5 Hz, 2H), 2.32 (t, J=7.2 Hz, 2H), 2.06-2.13 (m, 2H), 1.87-1.97 (m, 2H), 1.05-1.11 (m, 2H), 0.76-0.81 (m, 2H); MS m/z 426.4 [M+H$^+$].

Step 45b

Synthesis of 4-(4-((2-(5-cyclopropylthiazol-2-yl)-5-fluorobenzyl)oxy)phenyl)butanoic acid The title compound was prepared in an analogous manner as Example 1 involving the reaction of methyl 4-(4-((2-(5-cyclopropylthiazol-2-yl)-5-fluorobenzyl)oxy)phenyl)butanoate (0.045 g, 0.106 mM) with LiOH.H$_2$O (0.022 g, 0.529 mM), according to general procedure D (as described herein above). Yield: 0.041 g, 0.100 mM, 94%; $^1$H NMR (DMSO-d$_6$, 300 MHz) δ: 12.03 (s, 1H), 7.75-7.79 (m, 1H), 7.68 (s, 1H), 7.45-7.50 (m, 1H), 7.27-7.31 (m, 1H), 7.09 (d, J=8.4 Hz, 2H), 6.85 (d, J=8.4 Hz, 2H), 5.37 (s, 2H), 2.45-2.55 (m, 2H), 2.15-2.20 (m, 3H), 1.71-1.78 (m, 2H), 1.02-1.08 (m, 2H), 0.70-0.75 (m, 2H); MS m/z 412.4 [M+H$^+$].

Example 46

4-(4-((5-Fluoro-2-(4,5,6,7-tetrahydrobenzo[d]thiazol-2-yl)benzyl)oxy)phenyl)butanoic acid Step 46a Synthesis of methyl 4-(4-((5-fluoro-2-(4,5,6,7-tetrahydrobenzo[d]thiazol-2-yl)benzyl)oxy)phenyl)butanoate The title compound was prepared in an analogous manner as step 1c of Example 1 involving the reaction of 2-bromo-4,5,6,7-tetrahydrobenzo[d]thiazole (0.034 g, 0.156 mM), methyl 4-(4-((5-fluoro-2-(4,4,5,5-tetramethyl-1,3,2-dioxaborolan-2-yl)benzyl)oxy)phenyl)butanoate (0.100 g, 0.233 mM), $K_2CO_3$ (0.065 g, 0.467 mM) in presence of tetrakis(triphenylphosphine)palladium(0) (8.99 mg, 7.78 μmol) according to general procedure C (as described herein above). Yield: 0.054 g, 0.123 mM, 79%; $^1$H NMR (CDCl$_3$, 300 MHz) δ 7.63-7.67 (m, 1H), 7.43-7.47 (m, 1H), 7.01-7.09 (m, 3H), 6.85 (d, J=8.4 Hz, 2H), 5.42 (s, 2H), 3.66 (s, 3H), 2.75-2.85 (m, 4H), 2.59 (t, J=7.5 Hz, 2H), 2.32 (t, J=7.5 Hz, 2H), 1.90-1.97 (m, 6H); MS; m/z 440.3 [M+H$^+$].

Step 46b

Synthesis of 4-(4-((5-fluoro-2-(4,5,6,7-tetrahydrobenzo[d]thiazol-2-yl)benzyl)oxy)phenyl)butanoic acid The title compound was prepared in an analogous manner as Example 1 involving the reaction of methyl 4-(4-((5-fluoro-2-(4,5,6,7-tetrahydrobenzo[d]thiazol-2-yl)benzyl)oxy)phenyl)butanoate (0.040 g, 0.091 mM) with LiOH.H$_2$O (0.019 g, 0.455 mM), according to general procedure D (as described herein above). Yield: 0.034 g, 0.080 mM, 88%; $^1$H NMR (DMSO-d$_6$, 300 MHz) δ 12.03 (s, 1H), 7.72-7.80 (m, 1H), 7.40-7.50 (m, 1H), 7.25-7.35 (m, 1H), 7.09 (d, J=8.4 Hz, 2H), 6.83 (d, J=8.1 Hz, 2H), 5.37 (s, 2H), 2.77 (s, 2H), 2.67 (s, 2H), 2.40-2.50 (m, 2H), 2.10-2.20 (m, 2H), 1.65-1.85 (m, 6H); MS, m/z 425.3 [M$^+$].

Example 47

4-(4-((2-(5,6-dihydro-4H-cyclopenta[d]thiazol-2-yl)-5-fluorobenzyl)oxy)phenyl)butanoic acid Step 47a

Synthesis of methyl 4-(4-((2-(5,6-dihydro-4H-cyclopenta[d]thiazol-2-yl)-5-fluorobenzyl)oxy)phenyl)butanoate The title compound was prepared in an analogous manner as step 1c of Example 1 involving the reaction of 2-bromo-5,6-dihydro-4H-cyclopenta[d]thiazole (0.048 g, 0.233 mM), methyl 4-(4-((5-fluoro-2-(4,4,5,5-tetramethyl-1,3,2-dioxaborolan-2-yl)benzyl)oxy)phenyl)butanoate (0.150 g, 0.350 mM), K$_2$CO$_3$ (0.032 g, 0.233 mM) in presence of tetrakis (triphenylphosphine)palladium(0) (0.013 g, 0.012 mM) according to general procedure C (as described herein above). Yield: 0.084 g, 0.197 mM, 85%; $^1$H NMR (CDCl$_3$, 300 MHz) δ 7.65-7.69 (m, 1H), 7.45-7.49 (m, 1H), 7.01-7.09 (m, 3H), 6.87 (d, J=8.4 Hz, 2H), 5.42 (s, 2H), 3.66 (s, 3H), 2.88-2.99 (m, 4H), 2.48-2.61 (m, 4H), 2.32 (t, J=7.5 Hz, 2H), 1.87-1.97 (m, 2H); MS m/z 426.4 [M+H$^+$].

Step 47b

Synthesis of 4-(4-((2-(5,6-dihydro-4H-cyclopenta[d]thiazol-2-yl)-5-fluorobenzyl)oxy)phenyl)butanoic acid The title compound was prepared in an analogous manner as Example 1 involving the reaction of methyl 4-(4-((2-(5,6-dihydro-4H-cyclopenta[d]thiazol-2-yl)-5-fluorobenzyl)oxy)phenyl)butanoate (0.075 g, 0.176 mM) with LiOH.H$_2$O (0.037 g, 0.881 mM), according to general procedure D (as described herein above). Yield: 0.068 g, 0.165 mM, 94%; $^1$H NMR (DMSO-d$_6$, 300 MHz) δ 12.04 (s, 1H), 7.75-7.85 (m, 1H), 7.40-7.50 (m, 1H), 7.21-7.33 (m, 1H), 7.09 (d, J=7.8 Hz, 2H), 6.84 (d, J=7.8 Hz, 2H), 5.38 (s, 2H), 2.70-3.00 (s, 4H), 2.40-2.50 (m, 4H), 2.17 (t, J=6.9 Hz, 2H), 1.73-1.80 (m, 2H); MS, m/z 412.2 [M+H$^+$].

Example 48

4-(4-((2-(6,7-Dihydro-4H-pyrano[4,3-d]thiazol-2-yl)-5-fluorobenzyl)oxy)phenyl)butanoic acid Step 48a

Synthesis of methyl 4-(4-((2-(6,7-dihydro-4H-pyrano[4,3-d]thiazol-2-yl)-5-fluorobenzyl)oxy)phenyl)butanoate The title compound was prepared in an analogous manner as step 1c of Example 1 involving the reaction of 2-bromo-6,7-dihydro-4H-pyrano[4,3-d]thiazole (0.051 g, 0.233 mM), methyl 4-(4-((5-fluoro-2-(4,4,5,5-tetramethyl-1,3,2-dioxaborolan-2-yl)benzyl)oxy)phenyl)butanoate (0.150 g, 0.350 mM), K$_2$CO$_3$ (0.097 g, 0.700 mM) in presence of tetrakis (triphenylphosphine)palladium(0) (0.013 g, 0.012 mM) according to general procedure C (as described herein above). Yield: 0.081 g, 0.183 mM, 79%; $^1$H NMR (CDCl$_3$ 300 MHz) δ 7.65-7.69 (m, 1H), 7.45-7.49 (m, 1H), 7.03-7.10 (m, 3H), 6.85 (d, J=8.4 Hz, 2H), 5.41 (s, 2H), 4.88 (s, 2H), 4.07 (t, J=5.7 Hz, 2H), 3.66 (s, 3H), 2.96 (t, J=5.4 Hz, 2H), 2.59 (t, J=7.5 Hz, 2H), 2.32 (t, J=7.5 Hz, 2H), 1.87-1.97 (m, 2H); MS, m/z 442.1 [M+H$^+$].

Step 48b

Synthesis of 4-(4-((2-(6,7-dihydro-4H-pyrano[4,3-d]thiazol-2-yl)-5-fluorobenzyl)oxy)phenyl)butanoic acid The title compound was prepared in an analogous manner as Example 1 involving the reaction of methyl 4-(4-((2-(6,7-dihydro-4H-pyrano[4,3-d]thiazol-2-yl)-5-fluorobenzyl)oxy)phenyl)butanoate (0.071 g, 0.161 mM) with LiOH.H$_2$O (0.034 g, 0.804 mM), according to general procedure D (as described herein above). Yield: 0.061 g, 0.143 mM, 89%; $^1$H NMR (DMSO-d$_6$, 300 MHz) δ 12.03 (s, 1H), 7.78-7.82 (m, 1H), 7.40-7.50 (m, 1H), 7.28-7.33 (m, 1H), 7.08 (d, J=8.1 Hz, 2H), 6.83 (d, J=8.4 Hz, 2H), 5.38 (s, 2H), 4.80 (s, 2H), 3.93 (t, J=5.4 Hz, 2H), 2.70-2.85 (m, 2H), 2.40-2.50 (m, 2H), 2.17 (t, J=7.2 Hz, 2H), 1.70-1.75 (m, 2H); MS m/z 428.2 [M+H$^+$].

Example 49

4-(4-((2-(6,7-Dihydro-4H-pyrano[4,3-d]thiazol-2-yl)-5-fluorobenzyl)oxy)phenyl)butanoic acid Step 49a

Synthesis of methyl 4-(4-((2-(2,3-dihydrobenzo[b][1,4]dioxin-6-yl)-5-fluorobenzyl)oxy)phenyl)butanoate The title compound was prepared in an analogous manner as step 1c of Example 1 involving the reaction of 6-bromo-2,3-dihydrobenzo[b][1,4]dioxine (0.033 g, 0.156 mM), methyl 4-(4-((5-fluoro-2-(4,4,5,5-tetramethyl-1,3,2-dioxaborolan-2-yl)benzyl)oxy)phenyl)butanoate (0.100 g, 0.233 mM), K$_2$CO$_3$ (0.065 g, 0.467 mM) in presence of tetrakis (triphenyl)palladium(0) (8.99 mg, 7.78 μmol) according to general procedure C (as described herein above). Yield: 0.057 g, 0.131 mM, 84%; $^1$H NMR (CDCl$_3$, 300 MHz) δ 7.31-7.34 (m, 2H), 7.00-7.07 (m, 3H), 6.77-6.90 (m, 5H), 4.92 (s, 2H), 4.29 (s, 4H), 3.66 (s, 3H), 2.57 (t, J=7.2 Hz, 2H), 2.31 (t, J=7.5 Hz, 2H), 1.86-1.96 (m, 2H); MS, m/z 459.2 [M+Na$^+$].

Step 49b

Synthesis of 4-(4-((2-(6,7-dihydro-4H-pyrano[4,3-d]thiazol-2-yl)-5-fluorobenzyl)oxy)phenyl)butanoic acid The title compound was prepared in an analogous manner as Example 1 involving the reaction of methyl 4-(4-((2-(6,7-dihydro-4H-pyrano[4,3-d]thiazol-2-yl)-5-fluorobenzyl)oxy)phenyl)butanoate (0.045 g, 0.103 mM) with LiOH.H$_2$O (0.022 g, 0.515 mM), according to general procedure D (as described herein above). Yield: 0.040 g, 0.095 mM, 92%; $^1$H NMR (DMSO-d$_6$, 300 MHz) δ 12.02 (s, 1H), 7.29-7.38 (m, 2H), 7.19-7.25 (m, 1H), 7.07 (d, J=8.7 Hz, 2H), 6.78-6.88 (m, 5H), 4.91 (s, 2H), 4.24 (s, 4H), 2.40-2.50 (m, 2H), 2.17 (t, J=7.2 Hz, 2H), 1.70-1.77 (m, 2H); MS m/z 445.0 [M+Na$^+$].

Example 50

4-(4-((2-(4-Cyclopropylthiazol-2-yl)-5-fluorobenzyl)oxy)phenyl)butanoic acid Step 50a

Synthesis of methyl 4-(4-((2-(4-cyclopropylthiazol-2-yl)-5-fluorobenzyl)oxy)phenyl)butanoate The title compound was prepared in an analogous manner as step 1c of Example 1 involving the reaction of 2-bromo-4-cyclopropylthiazole (0.048 g, 0.233 mM), methyl 4-(4-((5-fluoro-2-(4,4,5,5-tetramethyl-1,3,2-dioxaborolan-2-yl)benzyl)oxy)phenyl)butanoate (0.150 g, 0.350 mM), potassium carbonate (0.097 g, 0.700 mM) in presence of tetrakis(triphenylphosphine)palladium(0) (0.013 g, 0.012 mM) according to general procedure C (as described herein above). Yield: 0.095 g, 0.223 mM, 96%; $^1$H NMR (CDCl$_3$, 300 MHz) δ 7.68-7.72 (m, 1H), 7.48-7.51 (s, 1H), 7.01-7.11 (m, 3H), 6.86-6.91 (m, 3H), 5.42 (s, 2H), 3.66 (s, 3H), 2.60 (t, J=7.5 Hz, 2H), 2.33 (t, J=7.5 Hz, 2H), 2.02-2.11 (m, 2H), 1.88-1.98 (m, 2H), 0.90-0.99 (m, 4H); MS m/z 426.4 [M+H$^+$].

Step 50b

Synthesis of 4-(4-((2-(4-cyclopropylthiazol-2-yl)-5-fluorobenzyl)oxy)phenyl)butanoic acid The title compound was prepared in an analogous manner as Example 1 involving the reaction of methyl-4-(4-((2-(4-cyclopropylthiazol-2-yl)-5-fluorobenzyl)oxy)phenyl)butanoate (0.090 g, 0.212 mM) with LiOH.H$_2$O (0.044 g, 1.058 mM), according to general procedure D (as described herein above). Yield: 0.060 g, 0.146 mM, 68.9%; $^1$H NMR (DMSO-d$_6$, 300 MHz) δ 12.03 (s, 1H), 7.79-7.84 (m, 1H), 7.49 (d, J=9.9 Hz, 1H), 7.38 (s, 1H), 7.27-7.32 (m, 1H), 7.09 (d, J=8.1 Hz, 2H), 6.85 (d, J=8.1 Hz, 2H), 5.3 (s, 2H), 2.40-2.50 (m, 2H), 2.07-2.19 (m, 3H), 1.71-1.76 (m, 2H), 0.82-0.88 (m, 4H); MS m/z 412.2 [M+H$^+$].

Example 51

4-(5-((5-Fluoro-2-(5,6,7,8-tetrahydronaphthalen-2-yl)benzyl)oxy)pyridin-2-yl)butanoic acid Step 51a

Synthesis of 5-(benzyloxy)-2-bromopyridine

6-Bromopyridin-3-ol (3.00 g, 17.24 mmol) and cesium carbonate (8.43 g, 25.9 mmol) were stirred in dry acetonitrile (30 mL). Benzyl bromide (3.24 g, 18.97 mmol) was added and stirred at RT for 3 h. After completion of reaction, the reaction mixture was filtered and washed with ethyl acetate. The combined organic layers were dried over sodium sulfate and concentrated to give the title compound, 5-(benzyloxy)-2-bromopyridine. Yield: 4.05 g, 89%.

Step 51b

Synthesis of ethyl 4-(5-(benzyloxy)pyridin-2-yl)butanoate 5-(Benzyloxy)-2-bromopyridine (3.00 g, 11.36 mmol) was stirred in dry THF (60 ml) under argon atmosphere. A 0.5 M solution of (4-ethoxy-4-oxobutyl)zinc(II) bromide in THF (25 mL, 12.49 mmol) was added carefully under argon atmosphere. After complete addition of (4-ethoxy-4-oxobutyl)zinc(II) bromide, PEPPSI™-IPr catalyst (0.386 g, 0.568 mmol) was added and reaction was stirred overnight at RT. The reaction mixture was decomposed with saturated ammonium chloride solution and extracted with ethyl acetate. The organic layer was washed with brine, dried and concentrated. The crude product was purified over silica gel using ethyl acetate/petroleum ether as eluent to give the title compound, ethyl 4-(5-(benzyloxy)pyridin-2-yl)butanoate. Yield: 2.2 g, 64.7%; $^1$H NMR (300 MHz, DMSO-d$_6$): δ 8.31 (m, 1H), 7.45-7.34 (m, 5H), 7.22-7.18 (m, 1H), 7.09-7.07 (d, J=8.4 Hz, 1H), 5.10 (s, 2H), 4.17-4.10 (q, 2H), 2.81-2.76 (t, 2H), 2.38-2.33 (t, 2H), 2.10-2.00 (m, 2H), 1.28 (t, 3H).

Step 51c

Synthesis of ethyl 4-(5-hydroxypyridin-2-yl)butanoate

Ethyl 4-(5-(benzyloxy)pyridin-2-yl)butanoate (0.37 g, 1.23 mmol) was stirred in dry ethanol (20 mL). Palladium/C (0.02 g) was added carefully under argon atmosphere and the reaction mixture was set for hydrogenation at 40 psi for 3 h. After completion of reaction, the reaction mixture was filtered carefully and the filtrate was concentrated to give title compound, ethyl 4-(5-hydroxypyridin-2-yl)butanoate (0.220 g, 85%). $^1$H NMR (300 MHz, DMSO-d$_6$): δ 8.22 (m, 1H), 7.25-7.23 (m, 1H), 7.13-7.10 (d, J=8.4 Hz, 1H), 4.16-4.09 (q, 2H), 2.82-2.77 (t, 2H), 2.378-2.33 (t, 2H), 2.04-2.00 (m, 2H), 1.27 (t, 3H).

Step 51d

Synthesis of ethyl 4-(5-((2-bromo-5-fluorobenzyl)oxy)pyridin-2-yl)butanoate

1-Bromo-2-(bromomethyl)-4-fluorobenzene (0.282 g, 1.05 mmol) and ethyl 4-(5-hydroxypyridin-2-yl)butanoate (0.220 g, 1.05 mmol) were stirred in dry acetonitrile. Cesium carbonate was added and reaction mixture was stirred overnight. After completion of reaction, the reaction mixture was filtered and the residue was washed with ethyl acetate. The combined organic layers were concentrated, purified over combiflash using ethyl acetate/pet ether as eluent to give title compound, 4-(5-((2-bromo-5-fluorobenzyl)oxy)pyridin-2-yl)butanoate. Yield: 0.320 g, 77%; $^1$H NMR (300 MHz, DMSO-d$_6$) δ: 8.33 (m, 1H), 7.58-7.54 (m, 1H), 7.13-7.10 (d, J=8.4 Hz, 1H), 4.16-4.09 (q, 2H), 2.82-2.77 (t, 2H), 2.378-2.33 (t, 2H), 2.04-2.00 (m, 2H), 1.27 (t, 3H).

Step 51e

Synthesis of ethyl 4-(5-((5-fluoro-2-(5,6,7,8-tetrahydronaphthalen-2-yl)benzyl)oxy)pyridin-2-yl)butanoate The title compound was prepared in an analogous manner as Example 1 involving the reaction of ethyl 4-(5-((2-bromo-5-fluorobenzyl)oxy)pyridin-2-yl)butanoate (0.100 g, 0.252 mmol) with (5,6,7,8-tetrahydronaphthalen-2-yl)boronic acid (0.067 g, 0.379 mmol) in presence of Tetrakis(triphenylphosphine)palladium(0) (0.01 g, 0.015 mmol), according to general procedure C (as described herein above). Yield: 0.057, 50.5%; $^1$H NMR (300 MHz, CDCl$_3$): δ 8.18 (s, 1H), 7.32-7.32 (m, 2H), 7.10-7.03 (m, 6H), 4.98 (s, 2H), 4.17-4.09 (q, J=7.2 Hz, 2H), 2.81-2.74 (m, 6H), 2.34 (t, J=7.2 Hz, J=14.7 Hz, 2H), 2.08-2.01 (m, 2H), 1.83 (m, 5H), 1.28-1.24 (m, 4H); MS: 448 (M+1).

Step 51f

Synthesis of 4-(5-((5-fluoro-2-(5,6,7,8-tetrahydronaphthalen-2-yl)benzyl)oxy)pyridin-2-yl)butanoic acid The title compound was prepared in an analogous manner as Example 1 involving the reaction of ethyl 4-(5-((5-fluoro-2-(5,6,7,8-tetrahydronaphthalen-2-yl)benzyl)oxy)pyridin-2-yl)butanoate (0.050 g, 0.11 mmol) with LiOH.H$_2$O (1.5M, 0.44 mL), according to general procedure D (as described herein above). Yield: 0.035 g, 76%; $^1$H NMR (300 MHz, DMSO-d$_6$): δ 12.03 (s, 1H), 8.16 (d, J=2.7 Hz, 1H), 7.45-7.23 (m, 8H), 4.96 (s, 2H), 2.71-2.63 (m, 6H), 2.19 (t, J=7.5 Hz, J=14.7 Hz, 2H), 1.86-1.81 (m, 2H), 1.71 (s, 4H); MS: 420 (M+1).

Example 52

4-(5-((2-(2,3-Dihydrobenzofuran-5-yl)-5-fluorobenzyl)oxy)pyridin-2-yl)butanoic acid Step 52a

Synthesis of ethyl 4-(5-((2-(2,3-dihydrobenzofuran-5-yl)-5-fluorobenzyl)oxy)pyridin-2-yl)butanoate The title compound was prepared in an analogous manner as Example 51 involving the reaction of ethyl 4-(5-((2-bromo-5-fluorobenzyl)oxy)pyridin-2-yl)butanoate (0.100 g, 0.252 mmol) with (2,3-dihydrobenzofuran-5-yl)boronic acid (0.062 g, 0.379 mmol) in presence of Tetrakis(triphenylphosphine)palladium(0) (0.01 g, 0.015 mmol), according to general procedure C (as described herein above). Yield: 0.047 g, 43%; $^1$H NMR (300 MHz, CDCl$_3$): δ 8.17 (s, 1H), 7.33-7.26 (m, 2H), 7.16 (s, 1H), 7.10-7.06 (m, 4H), 6.83 (d, J=8.1 Hz, 1H), 4.96 (s, 2H), 4.63 (t, J=8.7 Hz, 17.4 Hz, 2H), 4.17-4.09 (q, J=6.9 Hz, 2H), 3.23 (t, J=8.7 Hz, J=17.4 Hz, 2H), 2.77 (t, J=7.2 Hz, J=15 Hz, 2H), 2.34 (t, J=7.2 Hz, J=14.7 Hz, 2H), 2.08-2.01 (m, 2H), 1.28-1.24 (m, 3H); MS: 436 (M+1).

Step 52b

Synthesis of 4-(5-((2-(2,3-dihydrobenzofuran-5-yl)-5-fluorobenzyl)oxy)pyridin-2-yl)butanoic acid The title compound was prepared in an analogous manner as Example 1 involving the reaction of ethyl 4-(5-((2-(2,3-dihydrobenzofuran-5-yl)-5-fluorobenzyl)oxy)pyridin-2-yl)butanoate (0.040 g, 0.09 mmol) with LiOH.H$_2$O (1.5M, 0.37 mL), according to general procedure D (as described herein above). Yield: 0.030 g, 80%; $^1$H NMR (300 MHz, DMSO-d$_6$): δ 12.04 (s, 1H), 8.15 (s, 1H), 7.42-7.39 (m, 1H), 7.36-7.07 (m, 6H), 6.79 (m, 1H), 4.98 (s, 2H), 4.53 (t, J=8.7 Hz, J=17.4 Hz, 2H), 3.15 (t, J=8.7 Hz, J=17.1 Hz, 2H), 2.65 (t, J=7.2 Hz, J=15 Hz, 2H), 2.20 (t, J=7.2 Hz, J=14.7 Hz, 2H), 1.85-1.81 (m, 2H); MS: 408 (M+1).

Example 53

4-(5-((5-Fluoro-2-(6-methoxypyridin-3-yl)benzyl)oxy)pyridin-2-yl)butanoic acid Step 53a

Synthesis of ethyl 4-(5-((5-fluoro-2-(6-methoxypyridin-3-yl)benzyl)oxy)pyridin-2-yl)butanoate The title compound was prepared in an analogous manner as Example 51 involving the reaction of ethyl 4-(5-((2-bromo-5-fluorobenzyl)oxy)pyridin-2-yl)butanoate (0.120 g, 0.303 mmol) with (6-methoxypyridin-3-yl)boronic acid (0.069, 0.454 mmol) in presence of Tetrakis(triphenylphosphine)palladium(0) (0.01 g, 0.015 mmol), according to general procedure C (as described herein above). Yield: 0.042 g, 33%; $^1$H NMR (300 MHz, CDCl$_3$): δ 8.14 (m, 2H), 7.80 (d, J=3 Hz, 1H), 7.37-7.31 (m, 2H), 7.20-7.04 (m, 3H), 6.82 (d, J=8.1 Hz, 1H), 4.93 (s, 2H), 4.12 (q, J=6.9 Hz, 2H), 3.99 (s, 3H), 2.77 (t, J=7.5 Hz, J=15.3 Hz, 2H), 2.35 (t, J=7.5 Hz, J=15 Hz, 2H), 2.08-1.98 (m, 2H), 1.28-1.24 (t, J=7.2 Hz, J=14.4, 3H); MS: 425 (M+1).

Step 53b

Synthesis of 4-(5-((5-fluoro-2-(6-methoxypyridin-3-yl)benzyl)oxy)pyridin-2-yl)butanoic acid The title compound was prepared in an analogous manner as Example 1 involving the reaction of ethyl 4-(5-((2-(2,3-dihydrobenzofuran-5-yl)-5-fluorobenzyl)oxy)pyridin-2-yl) butanoate (0.040 g, 0.09 mmol) with LiOH.H$_2$O (1.5M, 0.37 mL), according to general procedure D (as described herein above). Yield: 0.033, 90%; $^1$H NMR (300 MHz, DMSO-d$_6$) δ: 12.04 (s, 1H), 8.18-8.14 (m, 2H), 7.77 (d, J=8.4 Hz, 1H), 7.49-7.12 (m, 5H), 6.88 (d, J=8.4 Hz, 1H), 5.00 (s, 2H), 3.86 (s, 3H), 2.65 (t, J=7.2 Hz, J=15 Hz, 2H), 2.20 (t, J=7.2 Hz, 14.4 Hz, 2H), 1.86-1.81 (m, 2H); MS: 397 (M+1).

Example 54

4-(5-((4'-Cyclopropyl-4-fluoro-[1,1'-biphenyl]-2-yl)methoxy)pyridin-2-yl)butanoic acid Step 54a

Synthesis of ethyl 4-(5-((4'-cyclopropyl-4-fluoro-[1,1'-biphenyl]-2-yl)methoxy)pyridin-2-yl)butanoate The title compound was prepared in an analogous manner as Example 51 involving the reaction of ethyl 4-(5-((2-bromo-5-fluorobenzyl)oxy)pyridin-2-yl)butanoate (0.120 g, 0.303 mmol) with (4-cyclopropylphenyl)boronic acid (0.074, 0.454 mmol) in presence of Tetrakis(triphenylphosphine)palladium(0) (0.01 g, 0.015 mmol), according to general procedure C (as described herein above). Yield: 0.050 g, 38%; $^1$H NMR (300 MHz, CDCl$_3$): δ 8.17 (s, 1H), 7.35-7.31 (m, 2H), 7.26-7.23 (m, 2H), 7.13-7.05 (m, 5H), 4.96 (s, 2H), 4.12 (q, J=7.2 Hz, 2H), 2.77 (t, J=7.5 Hz, J=15.3 Hz, 2H), 2.34 (t, J=7.2 Hz, 14.7 Hz, 2H), 2.08-2.01 (m, 2H), 1.28-1.24 (m, 4H), 1.05-0.99 (m, 2H), 0.77-0.74 (m, 2H); MS: 434 (M+1).

Step 54b

Synthesis of 4-(5-((4'-cyclopropyl-4-fluoro-[1,1'-biphenyl]-2-yl)methoxy)pyridin-2-yl)butanoic acid The title compound was prepared in an analogous manner as Example 1 involving the reaction of ethyl 4-(5-((4'-cyclopropyl-4-fluoro-[1,1'-biphenyl]-2-yl)methoxy)pyridin-2-yl)butanoate (0.040, 0.092 mmol) with LiOH.H$_2$O (1.5M, 0.4 mL), according to general procedure D (as described herein above). Yield: 0.033 g, 90%; $^1$H NMR (300 MHz, DMSO-d6): δ 12.02 (s, 1H), 8.13 (s, 2H), 7.44-7.21 (m, 5H), 7.20-7.14 (m, 3H), 4.98 (s, 2H), 2.65 (t, J=7.5 Hz, J=15 Hz, 2H), 2.20 (t, J=7.5 Hz, 14.7 Hz, 2H), 1.99-1.93 (m, 1H), 1.88-1.81 (m, 2H), 0.94-0.85 (m, 2H), 0.69-0.68 (m, 2H); MS: 406 (M+1).

Example 55

4-(5-((5-Fluoro-2-(5-methylthiophen-2-yl)benzyl)oxy)pyridin-2-yl)butanoic acid Step 55a

Synthesis of ethyl 4-(5-((5-fluoro-2-(5-methylthiophen-2-yl)benzyl)oxy)pyridin-2-yl)butanoate The title compound was prepared in an analogous manner as Example 51 involving the reaction of ethyl 4-(5-((2-bromo-5-fluorobenzyl)oxy)pyridin-2-yl)butanoate (0.150 g, 0.379 mmol) with (5-methylthiophen-2-yl)boronic acid (0.161 g, 01.131 mmol) in presence of Tetrakis(triphenylphosphine)palladium(0) (0.013 g, 0.019 mmol), according to general procedure C (as described herein above). Yield: 0.065 g, 41.5%; $^1$H NMR (300 MHz, CDCl$_3$): δ 8.24 (d, J=2.7 Hz, 1H), 7.45-7.40 (m, 1H), 7.35-7.31 (m, 1H), 7.15-7.07 (m, 3H), 6.84 (d, J=3.6 Hz, 1H), 6.74 (s, 1H), 5.11 (s, 2H), 4.17-4.10 (m, 2H), 2.78 (q, J=7.5 Hz, J=15.3 Hz, 2H), 2.52 (s, 3H), 2.35 (t, J=7.5 Hz, J=15 Hz, 2H), 2.07 (q, J=8.1 Hz, 2H), 1.29 (t, J=6.9 Hz, 14.1 Hz, 3H).

Step 55b

Synthesis of 4-(5-((5-fluoro-2-(5-methylthiophen-2-yl)benzyl)oxy)pyridin-2-yl)butanoic acid The title compound was prepared in an analogous manner as Example 1 involving the reaction of ethyl 4-(5-((5-fluoro-2-(5-methylthiophen-2-yl)benzyl)oxy)pyridin-2-yl)butanoate (0.060 g, 0.145 mmol) with LiOH.H$_2$O (1.5M, 0.58 mL), according to general procedure D (as described herein above). Yield: 0.034 g, 61%; $^1$H NMR (300 MHz, DMSO-d$_6$): δ 12.04 (s, 1H), 8.22 (s, 1H), 7.51-7.47 (m, 2H), 7.35-7.19 (m, 5H), 5.11 (s, 2H), 2.67 (t, J=7.2 Hz, J=15 Hz, 2H), 2.44 (s, 3H), 2.21 (t, J=7.5 Hz, 14.7 Hz, 2H), 1.87-1.82 (m, 2H); MS: 386 (M+1).

Example 56

4-(5-((2-(Bicyclo[4.2.0]octa-1(6),2,4-trien-3-yl)-5-fluorobenzyl)oxy)pyridine-2-yl)butanoic acid Step 56a

Synthesis of ethyl 4-(5-((2-(bicyclo[4.2.0]octa-1(6),2,4-trien-3-yl)-5-fluorobenzyl)oxy)pyridin-2-yl)butanoate The title compound was prepared in an analogous manner as Example 51 involving the reaction of ethyl 4-(5-((2-bromo-5-fluorobenzyl)oxy)pyridin-2-yl)butanoate (0.120 g, 0.303 mmol), with bicyclo[4.2.0]octa-1(6),2,4-trien-3-ylboronic acid (0.067 g, 0.454 mmol) in presence of Tetrakis(triphenylphosphine)palladium(0) (0.017 g, 0.015 mmol), according to general procedure C (as described herein above). Yield: 0.100 g, 79% yield; $^1$H NMR (300 MHz, CDCl$_3$) δ: 8.16 (s, 1H), 7.30-7.27 (m, 2H), 7.14-7.01 (m, 6H), 4.96 (s, 2H), 4.16-4.09 (q, J=7.2 Hz, 2H), 3.23 (s, 4H), 2.79-2.74 (t, J=7.5 Hz, J=15.3 Hz, 2H), 2.37-2.32 (d, J=7.5 Hz, J=15 Hz, 2H), 2.08-1.98 (m, 2H), 1.28-1.24 (m, 3H); MS: 420 (M+1).

Step 56b

Synthesis of 4-(5-((2-(bicyclo[4.2.0]octa-1(6),2,4-trien-3-yl)-5-fluorobenzyl)oxy)pyridine-2-yl)butanoic acid The title compound was prepared in an analogous manner as Example 1 involving the reaction of ethyl 4-(5-((2-(bicyclo[4.2.0]octa-1(6),2,4-trien-3-yl)-5-fluorobenzyl)oxy)pyridin-2-yl)butanoate (0.09 g, 0.215 mmol) with LiOH.H$_2$O (1.5M, 0.858 mL, 1.287 mmol), according to general procedure D (as described herein above). Yield: 0.080 g, 95%; $^1$H NMR (300 MHz, DMSO-d$_6$): δ: 12.03 (s, 1H), 7.41-7.32 (m, 1H), 7.30-7.08 (m, 8H), 4.97 (s, 2H), 2.64 (t, J=7.2 Hz, J=14.7 Hz, 2H), 2.19 (t, J=7.5 Hz, J=14.4 Hz, 2H), 1.85-1.80 (m, 2H), 1.23-1.15 (m, 4H); MS: 392 (M+1).

Example 57

4-(5-((4'-(1-cyanocyclopropyl)-4-fluoro-[1,1'-biphenyl]-2-yl)methoxy)pyridin-2-yl)butanoic acid Step 57a

Synthesis of ethyl 4-(5-((4'-(1-cyanocyclopropyl)-4-fluoro-[1,1'-biphenyl]-2-yl)methoxy)pyridin-2-yl)butanoate The title compound was prepared in an analogous manner as Example 51 involving the reaction of ethyl 4-(5-((2-bromo-5-fluorobenzyl)oxy)pyridin-2-yl)butanoate (0.120 g, 0.303 mmol), with (4-(1-cyanocyclopropyl)phenyl)boronic acid (0.085 g, 0.454 mmol) in presence of Tetrakis(triphenylphosphine)palladium(0) (0.017 g, 0.015 mmol), according to general procedure C (as described herein above). Yield: 0.115 g, 83%; $^1$H NMR (300 MHz, CDCl$_3$): δ 8.15 (s, 1H), 7.31-7.26 (m, 6H), 7.15-7.06 (m, 3H), 4.92 (s, 2H), 4.17 (q, J=7.2 Hz, 2H), 2.77 (t, J=7.2 Hz, J=15 Hz, 2H), 2.35 (t, J=7.5 Hz, J=15 Hz, 2H), 2.06-2.01 (m, 3H), 1.81-1.77 (m, 2H), 1.49-1.45 (m, 2H), 1.28-1.24 (m, 2H); MS: 459 (M+1).

Step 57b

Synthesis of 4-(5-((4'-(1-cyanocyclopropyl)-4-fluoro-[1,1'-biphenyl]-2-yl)methoxy)pyridin-2-yl)butanoic acid The title compound was prepared in an analogous manner as Example 1 involving the reaction of ethyl 4-(5-((4'-(1-cyanocyclopropyl)-4-fluoro-[1,1'-biphenyl]-2-yl)methoxy)pyridin-2-yl)butanoate (0.105 g, 0.229 mmol) with LiOH.H$_2$O (0.916 mL, 1.374 mmol), according to general procedure D (as described herein above). Yield: 0.090 g, 91%; $^1$H NMR (300 MHz, DMSO-d$_6$): δ 12.02 (s, 1H), 8.13 (d, J=2.7 Hz, 1H), 7.47-7.30 (m, 6H), 7.25-7.21 (m, 2H), 7.14-7.11 (m, 1H), 4.99 (s, 2H), 2.65 (t, J=7.2 Hz, J=14.7 Hz, 2H), 2.20 (t, J=7.5 Hz, J=14.7 Hz, 2H), 1.86-1.75 (m, 4H), 1.56-1.51 (m, 2H); MS: 431 (M+1).

Example 58

4-(5-((5-fluoro-2-(4,5,6,7-tetrahydrobenzo[d]thiazol-2-yl)benzyl)oxy)pyridin-2-yl)butanoic acid Step 58a

Synthesis of 5-fluoro-2-(4,5,6,7-tetrahydrobenzo[d]thiazol-2-yl)benzaldehyde 5-Fluoro-2-(4,4,5,5-tetramethyl-1,3,2-dioxaborolan-2-yl)benzaldehyde (0.200 g, 0.800 mmol), 2-bromo-4,5,6,7-tetrahydrobenzo[d]thiazole (0.209 g, 0.960 mmol) and potassium carbonate (0.276 g, 1.999 mmol) were stirred in dioxane:water (4:1) mixture (5 mL) and the reaction mixture was purged with argon for 5 minutes. Palladium tetrakis (0.011 g, 0.040 mmol) was added and again purged with argon for 5 minutes. The reaction mixture was heated at 110° C. for 2 h. After completion of reaction, the reaction mixture was concentrated and purified by column chromatography to obtain the title compound, 5-fluoro-2-(4,5,6,7-tetrahydrobenzo[d]thiazol-2-yl)benzaldehyde. Yield: 0.089 g, 43%; $^1$H NMR (300 MHz, DMSO-$d_6$): δ 10.31 (s, 1H), 7.89-7.84 (m, 1H), 7.65-7.56 (m, 2H), 2.84-2.77 (m, 4H), 1.83 (s, 4H); MS (m/z): 262 (M+1).

Step 58b

Synthesis of (5-fluoro-2-(4,5,6,7-tetrahydrobenzo[d]thiazol-2-yl)phenyl)methanol To a solution of 5-fluoro-2-(4,5,6,7-tetrahydrobenzo[d]thiazol-2-yl)benzaldehyde (0.080 g, 0.306 mmol) in methanol was added sodium borohydride (0.014 g, 0.367 mmol) at 0° C. The reaction mixture was stirred at RT for 1 h. After completion of reaction, the reaction mixture was concentrated, triturated with water, extracted with ethyl acetate, dried over sodium sulfate, concentrated and purified by column chromatography to provide the title compound, (5-fluoro-2-(4,5,6,7-tetrahydrobenzo[d]thiazol-2-yl)phenyl)methanol. Yield: 0.077 g, 96%; $^1$H NMR (300 MHz, CDCl$_3$): δ 7.68 (dd, J=5.7, 8.7 Hz, 1H), 7.18 (dd, J=2.4, 9 Hz, 1H), 7.09-7.03 (m, 1H), 6.37 (s, 1H), 4.56 (s, 2H), 1.91 (s, 4H), 1.58 (s, 4H); MS (m/z): 264 (M+1).

Step 58c

Synthesis of 2-(2-(bromomethyl)-4-fluorophenyl)-4,5,6,7-tetrahydrobenzo[d]thiazole To a solution of (5-fluoro-2-(4,5,6,7-tetrahydrobenzo[d]thiazol-2-yl)phenyl)methanol (0.070 g, 0.266 mmol) in DCM was added tribromophosphine (0.072 g, 0.266 mmol) at 0° C. The reaction mixture was stirred at room temperature for 1 h. After completion of reaction, the reaction mixture was diluted with DCM and washed with aqueous NaHCO$_3$. The aqueous layer was extracted with DCM. The organic layers were combined, dried over sodium sulfate and concentrated to obtain title compound, 2-(2-(bromomethyl)-4-fluorophenyl)-4,5,6,7-tetrahydrobenzo[d]thiazole. Yield: 64 mg, 0.196 mmol, 73.8% yield.

Step 58d

Synthesis of ethyl 4-(5-((5-fluoro-2-(4,5,6,7-tetrahydrobenzo[d]thiazol-2-yl)benzyl)oxy)pyridin-2-yl)butanoate A mixture of 2-(2-(bromomethyl)-4-fluorophenyl)-4,5,6,7-tetrahydrobenzo[d]thiazole (0.100 g, 0.307 mmol), ethyl 4-(5-hydroxypyridin-2-yl)butanoate (0.071 g, 0.337 mmol) and cesium carbonate (0.250 g, 0.766 mmol) in acetonitrile (5 mL) was stirred at RT for 2 h. The reaction mixture was filtered through Celite® and washed with ethyl acetate. The organic layers were combined, concentrated and purified by column chromatography to obtain the title compound, ethyl 4-(5-((5-fluoro-2-(4,5,6,7-tetrahydrobenzo[d]thiazol-2-yl)benzyl)oxy)pyridin-2-yl)butanoate. Yield: 0.037 g, 26.6%; $^1$H NMR (300 MHz, CDCl$_3$): δ 8.28 (d, J=3 Hz, 1H), 7.70-7.65 (m, 1H), 7.48-7.45 (m, 1H), 7.20-7.16 (m, 1H), 7.09-7.05 (m, 2H), 5.50 (s, 2H), 4.15 (q, J=6.9 Hz, 2H), 2.83-2.76 (m, 6H), 2.36 (t, J=7.5 Hz, J=15 Hz, 2H), 2.10-2.00 (m, 2H), 1.92-1.91 (m, 4H), 1.35-1.24 (m, 3H); MS: 455 (M+1).

Step 58e

Synthesis of 4-(5-((5-fluoro-2-(4,5,6,7-tetrahydrobenzo[d]thiazol-2-yl)benzyl)oxy)pyridin-2-yl)butanoic acid The title compound was prepared in an analogous manner as Example 1 involving the reaction of ethyl 4-(5-((5-fluoro-2-(4,5,6,7-tetrahydrobenzo[d]thiazol-2-yl)benzyl)oxy)pyridin-2-yl)butanoate (0.030 g, 0.066 mmol) with LiOH.H$_2$O (0.264 mL, 0.396 mmol), according to general procedure D (as described herein above). Yield: 0.025 g, 89%; $^1$H NMR (300 MHz, DMSO-$d_6$): δ 12.4 (s, 1H), 8.17 (s, 1H), 7.81-7.76 (m, 1H), 7.53-7.50 (m, 1H), 7.36-7.27 (m, 2H), 7.18-7.16 (m, 1H), 5.46 (s, 2H), 2.78 (s, 2H), 2.69-2.64 (m, 4H), 2.27-2.19 (m, 2H), 1.90-1.82 (m, 6H); MS: 427 (M+1).

Example 59

4-(5-(((5-fluoro-2-(5-(1-methylcyclopropyl)thiophen-2-yl)benzyl)oxy)pyridin-2-yl)butanoic acid Step 59a

Synthesis of 5-fluoro-2-(5-(1-methylcyclopropyl)thiophen-2-yl)benzaldehyde

To a solution of 2-bromo-5-(1-methylcyclopropyl)thiophene (0.660 g, 3.04 mmol) and (4-fluoro-2-formylphenyl)boronic acid (0.510 g, 3.04 mmol) in 15 mL dioxane:water (4:1) mixture was added potassium carbonate (1.05 g, 7.60 mmol) and the mixture was purged with argon for 5 minutes. To the resulting solution palladium tetrakistriphenylphosphine (0.211 g, 0.182 mmol) was added and the mixture was heated at 80° C. for 1 h. After completion of reaction, the reaction was quenched with water, extracted with ethyl acetate, dried over sodium sulfate, concentrated and purified by column chromatography to obtain the title compound, 5-fluoro-2-(5-(1-methylcyclopropyl)thiophen-2-yl)benzaldehyde as yellow semisolid. Yield: 0.316 g, 40%; $^1$H NMR (300 MHz, CDCl$_3$) δ; 10.16 (s, 1H), 7.68-7.64 (m, 1H), 7.54-7.46 (m, 2H), 7.39-7.31 (m, 1H), 6.83-6.80 (m, 1H), 2.17-2.08 (m, 1H), 1.53 (s, 3H), 1.03-1.00 (m, 2H), 0.99-0.91 (m, 2H); MS (m/z): 261.0 (M+1).

Step 59b

Synthesis of (5-fluoro-2-(5-(1-methylcyclopropyl)thiophen-2-yl)phenyl)methanol 5-Fluoro-2-(5-(1-methylcyclopropyl)thiophen-2-yl)benzaldehyde (0.180 g, 0.691 mmol) was stirred in methanol (2 mL) at 0° C. and sodium borohydride (0.026 g, 0.691 mmol) was added slowly. After complete addition of sodium borohydride, the reaction mixture was stirred at RT for 1 h. After completion of the reaction, the reaction mixture was concentrated under vacuum, the residue was quenched with water and extracted with ethyl acetate (10 mL×3). The organic layers were combined, dried over Na$_2$SO$_4$ and concentrated to obtain the title compound, (5-fluoro-2-(5-(1-methylcyclopropyl)thiophen-2-yl)phenyl)methanol. Yield: 0.150 g, 83%; $^1$H NMR (300 MHz, CDCl$_3$): δ 7.37-7.28 (m, 3H), 7.13-6.98 (m, 1H), 6.86-6.85 (m, 1H), 4.77-4.76 (m, 2H), 1.52 (s, 3H), 0.99-0.89 (m, 4H).

Step 59c

Synthesis of 2-(2-(bromomethyl)-4-fluorophenyl)-5-(1-methylcyclopropyl)thiophene To a solution of (5-fluoro-2-(5-(1-methylcyclopropyl)thiophen-2-yl)phenyl)methanol (0.180 g, 0.686 mmol) in DCM (2 mL), was added tribromophosphine (0.186 g, 0.686 mmol) at 0° C. The reaction mixture was stirred at 0° C. for 30 minutes. After completion of reaction, the reaction mixture was diluted with DCM and washed with ice cold solution of NaHCO$_3$ and then extracted with DCM. The organic layers were combined, washed with brine solution dried over anhydrous sodium sulfate and concentrated to obtain the title compound, 2-(2-(bromomethyl)-4-fluorophenyl)-5-(1-methylcyclopropyl)thiophene.

Step 59d

Ethyl 4-(5-((5-fluoro-2-(5-(1-methylcyclopropyl)thiophen-2-yl)benzyl)oxy)pyridin-2-yl)butanoate 2-(2-(Bromomethyl)-4-fluorophenyl)-5-(1-methylcyclopropyl)thiophene (0.200 g, 0.615 mmol), ethyl 4-(5-hydroxypyridin-2-yl)butanoate (0.142 g, 0.676 mmol) and cesium carbonate (0.501 g, 1.537 mmol) were stirred in acetonitrile (10 mL) at RT for 2 h. The reaction mixture was filtered through celite. The filtrate was washed with ethyl acetate, concentrated and the crude mass purified by column chromatography, to get ethyl 4-(5-((5-fluoro-2-(5-(1-methylcyclopropyl)thiophen-2-yl)benzyl)oxy)pyridin-2-yl)butanoate. Yield: 0.013 g, 4.66%; $^1$H NMR (300 MHz, CDCl$_3$): δ 8.24 (d, J=2.4 Hz, 1H), 7.45-7.40 (m, 1H), 7.34-7.30 (m, 1H), 7.15-7.04 (m, 3H), 6.82 (d, J=3.6 Hz, 1H), 6.73 (d, J=3.6 Hz, 1H), 5.11 (s, 2H), 4.17-4.10 (m, 2H), 2.81-2.74 (m, 2H), 2.36 (d, J=7.5 Hz, J=15 Hz, 2H), 2.10-2.00 (m, 2H), 1.50 (s, 3H), 1.31-1.24 (m, 3H), 0.96-0.86 (m, 4H); MS (m/z): 454 (M+1).

Step 59e

Synthesis of 4-(5-((5-fluoro-2-(5-(1-methylcyclopropyl)thiophen-2-yl)benzyl)oxy)pyridin-2-yl)butanoic acid The title compound was prepared in an analogous manner as Example 1 involving the reaction of ethyl 4-(5-((5-fluoro-2-(5-(1-methylcyclopropyl)thiophen-2-yl)benzyl)oxy)pyridin-2-yl) butanoate (0.010 g, 0.022 mmol) with LiOH.H$_2$O (0.088 mL, 0.132 mmol), according to general procedure D (as described herein above). Yield: 0.09 g, 96%; $^1$H NMR (300 MHz, DMSO-d$_6$): δ 8.14 (s, 1H), 7.46-7.32 (m, 2H), 7.24-7.05 (m, 3H), 6.82-6.79 (m, 1H), 6.74-6.58 (m, 1H), 5.13 (s, 2H), 3.02-2.85 (m, 2H), 2.43-2.39 (m, 2H), 2.08-2.02 (m, 2H), 1.24-1.17 (m, 3H), 1.02-0.901 (m, 4H); MS (m/z): 426 (M+1).

Example 60

4-(5-((4-fluoro-2-(4,5,6,7-tetrahydrobenzo[d]thiazol-2-yl)benzyl)oxy)pyridin-2-yl)butanoic acid Step 60a Synthesis of 4-fluoro-2-(4,5,6,7-tetrahydrobenzo[d]thiazol-2-yl)benzaldehyde 2-Bromo-4,5,6,7-tetrahydrobenzo[d]thiazole (1.732 g, 7.94 mmol), (5-fluoro-2-formylphenyl)boronic acid (2.00 g, 11.91 mmol) and potassium carbonate (3.29 g, 23.82 mmol) were stirred in a solvent mixture of dioxane (20 mL) and water (25 mL) and purged with argon for 5 minutes. To the resulting reaction mixture was added palladium tetrakistriphenylphosphine (0.459 g, 0.397 mmol) and argon was purged for 5 minutes. The reaction mixture was heated overnight at 80° C. then cooled to room temperature and filtered through Celite®. The filtrate was concentrated to give residue, which was dissolved in ethyl acetate, washed with water, brine solution, dried over sodium sulfate, concentrated and purified by flash chromatography to obtain the title compound, 4-fluoro-2-(4,5,6,7-tetrahydrobenzo[d]thi- azol-2-yl)benzaldehyde as a solid. Yield: 1.6 g, 77% yield; $^1$H NMR (300 MHz, CDCl$_3$): δ 10.49 (s, 1H), 8.09-8.04 (m, 1H), 7.41-7.37 (m, 1H), 7.24-7.18 (m, 1H), 2.88 (s, 4H), 1.94 (s, 4H); MS: 262 (M+1).

Step 60b

Synthesis of (4-fluoro-2-(4,5,6,7-tetrahydrobenzo[d]thiazol-2-yl)phenyl)methanol To a stirred solution of 4-fluoro-2-(4,5,6,7-tetrahydrobenzo[d]thiazol-2-yl)benzaldehyde (1.7 g, 6.51 mmol) in MeOH (25 mL) at 0° C. was added sodium borohydride (0.123 g, 3.25 mmol) portion wise and the reaction mixture was stirred for 2 h. After completion of reaction, the reaction mixture was concentrated, acidified by 1N HCl solution, extracted with ethyl acetate, washed with brine solution, dried, concentrated and purified to obtain the title compound (4-fluoro-2-(4,5,6,7-tetrahydrobenzo[d]thiazol-2-yl)phenyl)methanol as solid. Yield: 1.3 g, 76%; $^1$H NMR (300 MHz, CDCl$_3$): δ 7.45-7.36 (m, 2H), 7.11-7.05 (m, 1H), 6.25-6.20 (t, 1H, OH peak), 4.60-4.57 (d, 2H), 2.86 (s, 4H), 1.93 (s, 4H); MS: 264.1 (M+1).

Step 60c

Synthesis of 2-(2-(bromomethyl)-5-fluorophenyl)-4,5,6,7-tetrahydrobenzo[d]thiazole To a solution of (4-fluoro-2-(4,5,6,7-tetrahydrobenzo[d]thiazol-2-yl)phenyl)methanol (0.195 g, 0.741 mmol) in DCM (2 mL), was added tribromophosphine (0.070 mL, 0.741 mmol) at 0° C. The reaction mixture was stirred at 0° C. for 30 minutes. After completion of reaction, the reaction mixture was poured in ice cold water, neutralized with NaHCO$_3$ and extracted with DCM. The organic layers were combined, washed with brine solution, dried over sodium sulfate and concentrated under vacuum to obtain the title compound, 2-(2-(bromomethyl)-5-fluorophenyl)-4,5,6,7-tetrahydrobenzo[d]thiazole. Yield: 0.196 g, 81%.

Step 60d

Ethyl 4-(5-((4-fluoro-2-(4,5,6,7-tetrahydrobenzo[d]thiazol-2-yl)benzyl)oxy)pyridin-2-yl)butanoate A mixture of 2-(2-(bromomethyl)-4-fluorophenyl)-4,5,6,7-tetrahydrobenzo[d]thiazole (0.196 g, 0.601 mmol), ethyl 4-(5-hydroxypyridin-2-yl)butanoate (0.126 g, 0.601 mmol) and cesium carbonate (0.489 g, 1.502 mmol) were stirred in acetonitrile (5 mL) at RT for 2 h. The reaction mixture was filtered through Celite® and washed with ethyl acetate. The filtrate was concentrated and purified by column chromatography (0-20% EtOAc:petroleum ether), to obtain the title compound, ethyl 4-(5-((4-fluoro-2-(4,5,6,7-tetrahydrobenzo[d]thiazol-2-yl)benzyl)oxy)pyridin-2-yl)butanoate. Yield: 0.142 g, 52.0%; $^1$H NMR (300 MHz, CDCl$_3$): δ 8.26 (d, J=2.7 Hz, 1H), 7.68-7.64 (m, 1H), 7.44-7.40 (m, 1H), 7.18-7.06 (m, 3H), 5.45 (s, 2H), 4.15 (q, J=7.2 Hz, 2H), 2.84-2.76 (m, 6H), 2.36 (t, 2H), 2.10-2.02 (m, 2H), 1.90 (s, 4H), 1.29-1.24 (m, 3H); MS: 455 (M+1).

Step 60e

Synthesis of 4-(5-((4-fluoro-2-(4,5,6,7-tetrahydrobenzo[d]thiazol-2-yl)benzyl)oxy)pyridin-2-yl)butanoic acid The title compound was prepared in an analogous manner as Example 1 involving the reaction of ethyl 4-(5-((4-fluoro-2-(4,5,6,7-tetrahydrobenzo[d]thiazol-2-yl)benzyl)oxy)pyridin-2-yl)butanoate (0.132 g, 0.290 mmol) with LiOH.H$_2$O (1.162 ml, 1.742 mmol), according to general procedure D (as described herein above). Yield: 0.100 g, 81%; $^1$H NMR (300 MHz, DMSO-d$_6$): δ 12.06 (s, 1H), 8.14 (d, J=2.7 Hz, 1H), 7.73-7.68 (m, 1H), 7.57-7.54 (m, 1H), 7.38-7.26 (m, 2H), 6.82 (d, J=3.6 Hz, 1H), 5.40 (s, 2H), 2.78 (s, 2H), 2.69-2.60 (m, 4H), 2.21 (d, J=7.5 Hz, J=15 Hz, 2H), 1.99-1.77 (m, 6H); MS: 427 (M+1).

Example 61

4-(5-((2-(5-cyclopropylthiophen-2-yl)-4-fluorobenzyl)oxy)pyridin-2-yl)butanoic acid Step 61a Synthesis of 2-(5-cyclopropylthiophen-2-yl)-4-fluorobenzaldehyde To a solution of 2-bromo-5-cyclopropylthiophene (2 g, 9.85 mmol) and (5-fluoro-2-formylphenyl)boronic acid (2.150 g, 12.80 mmol) in 10 mL dioxane:water (4:1) mixture was added potassium carbonate (3.40 g, 24.62 mmol) and the mixture was purged with argon for 5 minutes. To the resulting solution palladiumtetrakistriphenylphosphine (0.683 g, 0.591 mmol) was added and argon was purged for 5 minutes. The reaction mixture was heated at 80° C. for 1 h. After completion of reaction, the reaction mixture was quenched with water, extracted with ethyl acetate, dried over sodium sulfate, concentrated and purified by column chromatography on silica gel to obtain the title compound 2-(5-cyclopropylthiophen-2-yl)-4-fluorobenzaldehyde and colorless thick liquid. Yield: 1.74 g, 7.06 mmol, 71.7%.

Step 61b

Synthesis of (2-(5-cyclopropylthiophen-2-yl)-4-fluorophenyl)methanol

To a solution of 2-(5-cyclopropylthiophen-2-yl)-4-fluorobenzaldehyde (2.3 g, 9.34 mmol) in methanol was added sodium borohydride (0.353 g, 9.34 mmol) and the reaction mixture was stirred at RT for 2 h. After completion of reaction, the reaction mixture was concentrated, diluted with acidified water (acidified with 1N HCl) and extracted with ethyl acetate to obtain the title compound (2-(5-cyclopropylthiophen-2-yl)-4-fluorophenyl)methanol. Yield: 2.2 g, 8.86 mmol, 95%.

Step 61c

Synthesis of 2-(2-(bromomethyl)-5-fluorophenyl)-5-cyclopropylthiophene

To a solution of (2-(5-cyclopropylthiophen-2-yl)-4-fluorophenyl)methanol (0.250 g, 1.007 mmol) in DCM, was added tribromophosphine (0.096 mL, 1.007 mmol) at 0° C. The reaction mixture was stirred at 0° C. for 30 minutes. After completion, the reaction mixture was poured in ice-cold water and neutralized with NaHCO$_3$ and extracted with DCM. The organic layers were combined, washed with brine solution, dried over sodium sulfate and concentrated to obtain the title compound, 2-(2-(bromomethyl)-5-fluorophenyl)-5-cyclopropylthiophene.

Step 61d

Synthesis of ethyl 4-(5-((2-(5-cyclopropylthiophen-2-yl)-4-fluorobenzyl)oxy)pyridin-2-yl)butanoate 2-(2-(Bromomethyl)-5-fluorophenyl)-5-cyclopropylthiophene (0.200 g, 0.643 mmol), ethyl 4-(5-hydroxypyridin-2-yl)butanoate (0.134 g, 0.643 mmol) and cesium carbonate (0.523 g, 1.607 mmol) were stirred in acetonitrile (5 mL) at RT for 2 h. The reaction mixture was filtered through Celite® and washed with ethyl acetate. The filtrate was concentrated and purified by column chromatography (0-20% EtOAc:pet ether), to obtain the title compound, ethyl 4-(5-((2-(5-cyclopropylthiophen-2-yl)-4-fluorobenzyl)oxy)pyridin-2-yl)butanoate. Yield: 0.168 g, 59.5%; $^1$H NMR (300 MHz, CDCl$_3$): δ 8.26 (d, J=2.4 Hz, 1H), 7.56-7.51 (m, 1H), 7.21-7.04 (m, 4H), 6.91 (d, J=3.3 Hz, 1H), 6.73 (d, J=3.6 Hz, 1H), 5.06 (s, 2H), 4.15 (q, J=6.9 Hz, 2H), 2.79 (t, J=7.5 Hz, 15.3 Hz, 2H), 2.36 (t, J=7.5 Hz, J=15 Hz, 2H), 2.08-2.06 (m, 3H), 1.29-1.24 (m, 3H), 1.04-0.99 (m, 2H), 0.76-0.74 (m, 2H); MS: 440 (M+1).

Step 61e

Synthesis of 4-(5-((2-(5-cyclopropylthiophen-2-yl)-4-fluorobenzyl)oxy)pyridin-2-yl)butanoic acid The title compound was prepared in an analogous manner as Example 1 involving the reaction of ethyl 4-(5-((2-(5-cyclopropylthiophen-2-yl)-4-fluorobenzyl)oxy)pyridin-2-yl)butanoate (0.160 g, 0.364 mmol) with LiOH.H$_2$O (1.456 mL, 2.184 mmol), according to general procedure D (as described herein above). Yield: 0.139 g, 93% yield; $^1$H NMR (300 MHz, DMSO-d$_6$): δ 12.04 (s, 1H), 8.21 (s, 1H), 7.69-7.64 (m, 1H), 7.35-7.16 (m, 4H), 7.05 (d, J=3.6 Hz, 1H), 6.82 (d, J=3.6 Hz, 1H), 5.06 (s, 2H), 2.68 (t, J=7.5 Hz, 15 Hz, 2H), 2.24-2.19 (m, 2H), 2.10-1.99 (m, 1H), 1.88-1.83 (m, 2H), 1.23-1.15 (m, 4H).

Example 62

Biological Assays

Representative compounds of formula (I) of the present invention (referred to as test compounds) were tested for their activity using the assays and the methods described below Beta (β) arrestin 2 Interaction Assay (BRET assay) was performed using CHO-K1 cells stably expressing the GPR120L receptor using β-galactosidase (Beta gal) enzyme fragment complementation assay. The measurement of GPR120 activation upon agonist activation was directly provided by β-arrestin recruitment. One day before the β-arrestin 2 assay, CHO-K1 cells were seeded and incubated overnight at 37° C. in a 5% CO$_2$ humidified atmosphere. Cells were treated with the test compounds in the various concentrations ranging from 30 μM to 1 nM and incubated for 2 hours for GPCR (GPR120) activation. Extent of Arrestin recruitment was measured by adding detection reagents for Beta gal complementation assay and was further incubated for 1 hour. The chemi-luminescent signal was detected on Polar Star (BMG Labtech). The dose-response curve was analyzed using Sigma Plot/Graph Pad. The EC$_{50}$ (concentration of the test compounds where 50% of compounds' maximal activity is observed) values were calculated from the dose-response curve.

TABLE 1

EC$_{50}$ values of compounds of Examples

| Examples No. | EC$_{50}$ (nM) |
| --- | --- |
| Example 1 | +++ |
| Example 2 | ++ |
| Example 3 | +++ |
| Example 4 | +++ |

TABLE 1-continued

EC$_{50}$ values of compounds of Examples

| Examples No. | EC$_{50}$ (nM) |
|---|---|
| Example 5 | +++ |
| Example 6 | ++ |
| Example 7 | +++ |
| Example 8 | +++ |
| Example 9 | +++ |
| Example 10 | +++ |
| Example 11 | +++ |
| Example 12 | ++ |
| Example 13 | + |
| Example 14 | ++ |
| Example 15 | + |
| Example 16 | ++ |
| Example 17 | + |
| Example 18 | +++ |
| Example 19 | ++ |
| Example 20 | ++ |
| Example 21 | + |
| Example 22 | +++ |
| Example 23 | +++ |
| Example 24 | +++ |
| Example 25 | ++ |
| Example 26 | +++ |
| Example 27 | +++ |
| Example 28 | +++ |
| Example 29 | +++ |
| Example 30 | +++ |
| Example 31 | +++ |
| Example 32 | + |
| Example 33 | +++ |
| Example 34 | ++ |
| Example 35 | +++ |
| Example 36 | +++ |
| Example 37 | ++ |
| Example 38 | + |
| Example 39 | + |
| Example 40 | +++ |
| Example 41 | +++ |
| Example 42 | + |
| Example 43 | +++ |
| Example 44 | +++ |
| Example 45 | +++ |
| Example 46 | +++ |
| Example 47 | +++ |
| Example 48 | ++ |
| Example 49 | +++ |
| Example 50 | ++ |

+++ corresponds to EC$_{50}$ ranging from 10 nM to 500 nM;
++ corresponds to EC$_{50}$ ranging from 500 nM to 5000 nM;
+ corresponds to EC$_{50}$ ranging from 5000 nM to 50000 nM;

Conclusion:

The EC$_{50}$ values determined for the compounds of the present invention is indicative of GPR120 agonist activity of the compounds of the present invention.

We claim:

1. A compound of formula (I):

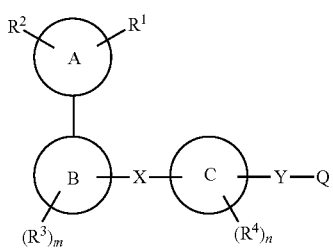

Formula (I)

or a stereoisomer, a tautomer, a geometrical isomer, a pharmaceutically acceptable salt, a pharmaceutically acceptable solvate, a prodrug, an N-oxide, a S-oxide or a carboxylic acid isostere thereof;

wherein:

Ring A is a saturated or unsaturated optionally substituted 4- to 10-membered carbocycle; an optionally substituted 5- to 10-membered heteroaryl; or a saturated or partly saturated or unsaturated optionally substituted 5- to 10-membered heterocycle; wherein said heteroaryl or heterocycle contain 1, 2, 3 or 4 heteroatoms independently selected from N, O and S;

Ring B and Ring C are independently selected from the group consisting of optionally substituted (C$_6$-C$_{10}$) aryl and optionally substituted 6- to 10-membered heteroaryl which contains 1, 2 or 3 heteroatoms independently selected from the group consisting of N, O and S;

X is —(CR$^8$R$^9$)$_p$—O—, (CR$^8$R$^9$)$_p$—S—, —(CR$^8$R$^9$)$_p$—N(R$^{10}$)—, —O—(CR$^8$R$^9$)$_p$—, —S—(CR$^8$R$^9$)$_p$— or —N(R$^{10}$)—(CR$^8$R$^9$)$_p$;

Y is —(CR$^{14}$R$^{15}$)$_g$—;

Q is —CO$_2$M, —CONH$_2$, —CONH[(C$_1$-C$_6$)alkyl], —CON[(C$_1$-C$_6$)alkyl]$_2$ or —CONHSO$_2$(C$_1$-C$_6$)alkyl;

M is hydrogen, deuterium or (C$_1$-C$_6$)alkyl;

R$^1$ is

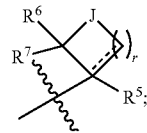

wherein

⸹ is point of attachment to Ring A;

J is —CH$_2$—, —CHF—, —CF$_2$—, —CH[(C$_1$-C$_6$) alkyl]—, or —C[(C$_1$-C$_6$)alkyl]$_2$-;

"-----" represents an optional bond;

R$^a$ is hydrogen, (C$_1$-C$_6$)alkyl or halo(C$_1$-C$_6$)alkyl;

R$^2$ is selected from the group consisting of hydrogen, halogen, (C$_1$-C$_6$)alkyl, halo(C$_1$-C$_6$)alkyl, (C$_1$-C$_6$) alkoxy, hydroxy, (C$_3$-C$_{10}$)cycloalkyl, (C$_6$-C$_{10}$)aryl, heteroaryl, heterocyclyl, (C$_6$-C$_{10}$)aryl-(C$_1$-C$_6$)alkyl, (C$_1$-C$_6$)alkyl-(C$_6$-C$_{10}$)aryl-, (C$_6$-C$_{10}$)aryloxy, heterocyclyl-(C$_1$-C$_6$)alkyl, (C$_1$-C$_6$)alkyl-heterocyclyl, heteroaryl-(C$_1$-C$_6$)alkyl, (C$_1$-C$_6$)alkyl-heteroaryl, cyano, —NR$^{10}$R$^{11}$, —C(O)NR$^{10}$R$^{11}$, —C(S) NR$^{10}$R$^{11}$, —S(O)$_r$R$^{12}$ and —C(O)R$^{13}$; or R$^1$ and R$^2$ are combined together with one or two atoms of Ring A to form:

a 3- to 8-membered partly unsaturated or saturated carbocycle wherein the said carbocycle or heterocycle can be unsubstituted or substituted with the one or more groups independently selected from the group consisting of (C$_1$-C$_6$)alkenyl, (C$_1$-C$_6$)alkyl, halo(C$_1$-C$_6$)alkyl, (C$_1$-C$_6$)alkoxy, hydroxy, halogen, cyano, oxo, (C$_3$-C$_{10}$) cycloalkyl, (C$_6$-C$_{10}$)aryl, heteroaryl and heterocyclyl and wherein Ring A together with R$^1$ and R$^2$ does not form an unsubstituted tetrahydronaphthyl group;

R$^3$ at each occurrence, is independently selected from the group consisting of hydrogen, halogen, (C$_1$-C$_6$) alkyl, halo(C$_1$-C$_6$)alkyl, (C$_1$-C$_6$)alkoxy, hydroxy, (C$_3$-C$_{10}$)cycloalkyl, (C$_6$-C$_{10}$)aryl, heteroaryl, heterocyclyl, (C$_6$-C$_{10}$)aryl-(C$_1$-C$_6$)alkyl, (C$_1$-C$_6$)alkyl- ($C_6$-$C_{10}$)aryl, ($C_6$-$C_{10}$)aryloxy, heterocyclyl-($C_1$-$C_6$)alkyl, ($C_1$-$C_6$)alkyl-heterocyclyl-, heteroaryl-($C_1$-$C_6$)alkyl, ($C_1$-$C_6$)alkyl-heteroaryl, cyano, —NR$^{10}$R$^{11}$, —C(O)NR$^{10}$R$^{11}$, —C(S)NR$^{10}$R$^{11}$, —S(O)$_r$R$^{12}$ and —C(O)R$^{13}$;

R$^4$ at each occurrence, is independently selected from the group consisting of hydrogen, ($C_1$-$C_6$)alkyl, halo($C_1$-$C_6$)alkyl, ($C_1$-$C_6$)alkoxy, hydroxy, halogen, cyano, ($C_3$-$C_{10}$)cycloalkyl, ($C_6$-$C_{10}$)aryl, heteroaryl, heterocyclyl, ($C_6$-$C_{10}$)aryl-($C_1$-$C_6$)alkyl, ($C_1$-$C_6$)alkyl-($C_6$-$C_{10}$)aryl, ($C_6$-$C_{10}$)aryloxy, heterocyclyl-($C_1$-$C_6$)alkyl, ($C_1$-$C_6$)alkyl-heterocyclyl, heteroaryl-($C_1$-$C_6$)alkyl, ($C_1$-$C_6$)alkyl-heteroaryl, —NR$^{10}$R$^{11}$, —S(O)$_r$R$^{12}$ and —C(O)R$^{13}$;

R$^5$ is selected from the group consisting of hydrogen, ($C_1$-$C_6$)alkyl, hydroxy, cyano, —COR$^{10}$, —NR$^{10}$R$^{11}$, —CONR$^{10}$R$^{11}$, ($C_1$-$C_6$)alkylamino, di($C_1$-$C_6$)alkylamino, ($C_1$-$C_6$)alkoxy, halo($C_1$-$C_6$)alkyl, —S(O)$_r$R$^{12}$ and —C(O)R$^{13}$;

R$^6$ and R$^7$ are independently selected from the group consisting of hydrogen, ($C_1$-$C_6$)alkyl, halo($C_1$-$C_6$)alkyl and halogen;

R$^8$ and R$^9$ are independently selected from the group consisting of hydrogen, deuterium, ($C_1$-$C_6$)alkyl, halo($C_1$-$C_6$)alkyl and halogen; or R$^8$ and R$^9$ together with the carbon atom they are attached to form:

i) a 3- to 5-membered saturated carbocycle selected from the group consisting of cyclopropane, cyclobutane, cyclopentane and cyclohexane; or ii) a 4- to 6-membered saturated heterocycle selected from the group consisting of oxetane, thietane, azetidine, tetrahydrofuran, tetrahydrothiophene, pyrolidine and piperidine;

R$^{10}$ is hydrogen, hydroxy, ($C_1$-$C_6$)alkyl, halo($C_1$-$C_6$)alkyl, ($C_1$-$C_6$)alkoxy, ($C_3$-$C_{10}$)cycloalkyl, ($C_6$-$C_{10}$)aryl, heterocyclyl, heteroaryl, ($C_6$-$C_{10}$)aryloxy, ($C_6$-$C_{10}$)aryl-($C_1$-$C_6$)alkyl, ($C_1$-$C_6$)alkyl-($C_6$-$C_{10}$)aryl, heterocyclyl-($C_1$-$C_6$)alkyl, ($C_1$-$C_6$)alkyl-heterocyclyl, heteroaryl-($C_1$-$C_6$)alkyl or ($C_1$-$C_6$)alkyl-heteroaryl or —S(O)$_r$R$^{12}$;

R$^{11}$ is hydrogen, hydroxy, ($C_1$-$C_6$)alkyl, halo($C_1$-$C_6$)alkyl, ($C_3$-$C_{10}$)cycloalkyl, ($C_1$-$C_6$)alkoxy, ($C_3$-$C_{10}$)cycloalkyl, ($C_6$-$C_{10}$)aryl, heterocyclyl, heteroaryl, ($C_6$-$C_{10}$)aryloxy, ($C_6$-$C_{10}$)aryl-($C_1$-$C_6$)alkyl, ($C_1$-$C_6$)alkyl-($C_6$-$C_{10}$)aryl, heterocyclyl-($C_1$-$C_6$)alkyl, ($C_1$-$C_6$)alkyl-heterocyclyl, heteroaryl-($C_1$-$C_6$)alkyl, ($C_1$-$C_6$)alkyl-heteroaryl or —S(O)$_r$R$^{12}$; or R$^{10}$ and R$^{11}$ are combined together to form 3- to 8-membered saturated or unsaturated ring which contains 1, 2 or 3 heteroatoms independently selected from N, O and S;

R$^{12}$ and R$^{13}$ are independently selected from the group consisting of hydrogen, ($C_1$-$C_6$)alkyl, halo($C_1$-$C_6$)alkyl, ($C_3$-$C_{10}$)cycloalkyl, ($C_6$-$C_{10}$)aryl, heterocyclyl, heteroaryl, ($C_6$-$C_{10}$)aryl-($C_1$-$C_6$)alkyl, ($C_1$-$C_6$)alkyl-($C_6$-$C_{10}$)aryl, heterocyclyl-($C_1$-$C_6$)alkyl, ($C_1$-$C_6$)alkyl-heterocyclyl, heteroaryl-($C_1$-$C_6$)alkyl and ($C_1$-$C_6$)alkyl-heteroaryl;

R$^{14}$ and R$^{15}$ are independently selected from the group consisting of hydrogen, ($C_1$-$C_6$)alkyl, halo($C_1$-$C_6$)alkyl and halogen; or R$^{14}$ and R$^{15}$ are combined together to form a 3- to 5-membered saturated carbocycle or 4- to 6-membered saturated heterocycle which optionally contains 1 or 2 heteroatoms independently selected from the group consisting of N, O and S; wherein the said carbocycle or heterocycle can be unsubstituted or substituted;

g is 2, 3, 4, 5 or 6;
m is 0, 1 or 2;
n is 0, 1 or 2;
p is 1, 2 or 3;
r is 0, 1, 2, 3 or 4;
t is 0, 1 or 2;

wherein
($C_1$-$C_6$)alkyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, ($C_6$-$C_{10}$)aryloxy, heterocyclyl, heteroaryl, amino, cyano, nitro, —NH($C_1$-$C_6$)alkyl, —N[($C_1$-$C_6$)alkyl]$_2$, —C(O)($C_1$-$C_6$)alkyl, —C(O)O($C_1$-$C_6$)alkyl, —C(O)NH$_2$, —C(O)NH($C_1$-$C_6$)alkyl, —C(O)N[($C_1$-$C_6$)alkyl]$_2$ and —C(O)NHSO$_2$($C_1$-$C_6$)alkyl;

($C_3$-$C_{10}$)cycloalkyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, amino, cyano and nitro;

carbocycle is unsubstituted or substituted with one or more groups independently selected from the group consisting of ($C_1$-$C_6$)alkyl, halo($C_1$-$C_6$)alkyl, hydroxy, halogen, ($C_1$-$C_6$)alkoxy, halo($C_1$-$C_6$)alkoxy, ($C_6$-$C_{10}$)aryl, ($C_3$-$C_{10}$)cycloalkyl, heteroaryl, heterocyclyl, amino, cyano, nitro, —C(O)O($C_1$-$C_6$)alkyl, —C(O)NR$^{10}$R$^{11}$ and —S(O)$_r$R$^{12}$; wherein R$^{10}$, R$^{11}$, R$^{12}$ and t are as defined above;

($C_6$-$C_{10}$)aryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)O($C_1$-$C_6$)alkyl, —C(O)NR$^{10}$R$^{11}$ and —S(O)$_r$R$^{12}$; wherein R$^{10}$, R$^{11}$, R$^{12}$ and t are as defined above;

heterocyclyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)NR$^{10}$R$^{11}$ and —S(O)$_r$R$^{12}$; wherein R$^{10}$, R$^{11}$, R$^{12}$ and t are as defined above;

heteroaryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, heterocyclyl, heteroaryl, amino, cyano, nitro, —C(O)NR$^{10}$R$^{11}$ and —S(O)$_r$R$^{12}$; wherein R$^{10}$, R$^{11}$, R$^{12}$ and t are as defined above.

2. A compound according to claim 1, wherein R$^1$ is

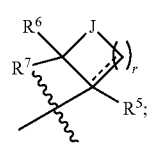

wherein

⸳ is point of attachment to Ring A;

J is —CH$_2$—, —CHF—, —CF$_2$—, —CH[($C_1$-$C_6$)alkyl], or —C[($C_1$-$C_6$)alkyl]$_2$-;

"-----" represents an optional bond;

$R^5$, $R^6$, $R^7$ and r are as defined in claim 1;
$R^2$ is selected from the group consisting of hydrogen, halogen, ($C_1$-$C_6$)alkyl, halo($C_1$-$C_6$)alkyl, ($C_1$-$C_6$) alkoxy, hydroxy, ($C_3$-$C_{10}$)cycloalkyl, ($C_6$-$C_{10}$)aryl, heteroaryl, heterocyclyl, ($C_6$-$C_{10}$)aryl-($C_1$-$C_6$)alkyl, ($C_1$-$C_6$)alkyl-($C_6$-$C_{10}$)aryl-, ($C_6$-$C_{10}$)aryloxy, heterocyclyl-($C_1$-$C_6$)alkyl, ($C_1$-$C_6$)alkyl-heterocyclyl, heteroaryl-($C_1$-$C_6$)alkyl, ($C_1$-$C_6$)alkyl-heteroaryl, cyano, —$NR^{10}R^{11}$, —$C(O)NR^{10}R^{11}$, —$C(S)NR^{10}R^{11}$, —$S(O)_rR^{12}$ and —$C(O)R^{13}$.

3. A compound according to claim 1, wherein
$R^1$ and $R^2$ are combined together with one or two atoms of Ring A to form:
  a 3- to 8-membered, partly saturated or saturated carbocycle
wherein the carbocycle or heterocycle is unsubstituted or substituted with the one or more groups independently selected from the group consisting of ($C_1$-$C_6$)alkyl, halo($C_1$-$C_6$)alkyl, ($C_1$-$C_6$)alkoxy, hydroxy, halogen, cyano, ($C_6$-$C_{10}$)aryl, heteroaryl and heterocyclyl and
wherein Ring A together with $R^1$ and $R^2$ does not form an unsubstituted tetrahydronaphthyl group.

4. A compound according to claim 1, wherein Ring A is a 6- to 10-membered aromatic carbocycle; a 5- or 6-membered heteroaryl or a 5- or 6-membered heterocyclyl wherein heteroaryl and heterocyclyl contain 1, 2 or 3 heteroatoms independently selected from the group consisting of N, O and S;
wherein
  aromatic carbocycle is unsubstituted or substituted with one or more groups independently selected from the group consisting of ($C_1$-$C_6$)alkyl, halo($C_1$-$C_6$)alkyl, hydroxy, halogen, ($C_1$-$C_6$)alkoxy, halo($C_1$-$C_6$)alkoxy, ($C_6$-$C_{10}$)aryl, ($C_3$-$C_{10}$)cycloalkyl, heteroaryl, heterocyclyl, amino, cyano, nitro, —C(O)O($C_1$-$C_6$)alkyl, —C(O)$NR^{10}R^{11}$ and —$S(O)_rR^{12}$; wherein $R^{10}$, $R^{11}$, $R^{12}$ and t are as defined above;
  heteroaryl is unsubstituted or substituted with one or more groups independently selected from the group consisting of ($C_1$-$C_6$)alkyl, halogen, halo($C_1$-$C_6$) alkyl, hydroxy, ($C_1$-$C_6$)alkoxy, halo($C_1$-$C_6$)alkoxy, heterocyclyl, heteroaryl, amino, cyano, nitro, —C(O)$NR^{10}R^{11}$ and —$S(O)_rR^{12}$; wherein $R^{10}$, $R^{11}$, $R^{12}$ and t are as defined above;
  heterocyclyl is unsubstituted or substituted with one or more groups independently selected from the group consisting of ($C_1$-$C_6$)alkyl, halogen, halo($C_1$-$C_6$) alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)$NR^{10}R^{11}$ and —$S(O)_rR^{12}$; wherein $R^{10}$, $R^{11}$, $R^{12}$ and t are as defined above.

5. A compound according to claim 1, wherein Ring A is 6- to 10-membered aromatic carbocycle, wherein aromatic carbocycle is unsubstituted or substituted with one or more groups independently selected from the group consisting of ($C_1$-$C_6$)alkyl, halo($C_1$-$C_6$)alkyl, hydroxy, halogen, ($C_1$-$C_6$) alkoxy, halo($C_1$-$C_6$)alkoxy, ($C_6$-$C_{10}$)aryl, ($C_3$-$C_{10}$)cycloalkyl, heteroaryl, heterocyclyl, amino, cyano, nitro, —C(O)O($C_1$-$C_6$)alkyl, —C(O)$NR^{10}R^{11}$ and —$S(O)_rR^{12}$; wherein $R^{10}$, $R^{11}$, $R^{12}$ and t are as defined above.

6. A compound according to claim 1, wherein Ring A is phenyl; wherein phenyl is unsubstituted or substituted with one or more groups independently selected from the group consisting of ($C_1$-$C_6$)alkyl, halo($C_1$-$C_6$)alkyl, hydroxy, halogen, ($C_1$-$C_6$)alkoxy, halo($C_1$-$C_6$)alkoxy, ($C_6$-$C_{10}$)aryl, ($C_3$-$C_{10}$)cycloalkyl, heteroaryl, heterocyclyl, amino, cyano, nitro, —C(O)O($C_1$-$C_6$)alkyl, —C(O)$NR^{10}R^{11}$ and —$S(O)_rR^{12}$; wherein $R^{10}$, $R^{11}$, $R^{12}$ and t are as defined above.

7. A compound according to claim 1, wherein Ring A is a 5- or 6-membered heteroaryl containing 1, 2 or 3 heteroatoms independently selected from the group consisting of N, O and S; wherein
  heteroaryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, heterocyclyl, heteroaryl, amino, cyano, nitro, —C(O)$NR^{10}R^{11}$ and —$S(O)_rR^{12}$; wherein $R^{10}$, $R^{11}$, $R^{12}$ and t are as defined above;
  heterocyclyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$) cycloalkyl, ($C_6$-$C_{10}$)aryl, heterocyclyl, heteroaryl, amino, cyano, nitro, —C(O)$NR^{10}R^{11}$ and —$S(O)_rR^{12}$; wherein $R^{10}$, $R^{11}$, $R^{12}$ and t are as defined above.

8. A compound according to claim 1, wherein Ring A is 5- or 6-membered heteroaryl selected from the group consisting of pyrrole, pyrazole, imidazole, pyrazine, furan, thiophene, oxazole, oxadiazole, thiazole, thiadiazole, pyridine, pyrimidine, and tetrazole; wherein each of the heteroaryl ring is unsubstituted or substituted with one or more groups independently selected from the group consisting of ($C_1$-$C_6$)alkyl, halogen, halo($C_1$-$C_6$)alkyl, hydroxy, ($C_1$-$C_6$) alkoxy, halo($C_1$-$C_6$)alkoxy, heterocyclyl, heteroaryl, amino, cyano, nitro, —C(O)$NR^{10}R^{11}$ and —$S(O)_rR^{12}$; wherein $R^{10}$, $R^{11}$, $R^{12}$ and t are as defined above.

9. A compound according to claim 1, wherein Ring B is ($C_6$-$C_{10}$)aryl; wherein ($C_6$-$C_{10}$)aryl is unsubstituted or substituted with one or more groups independently selected from the group consisting of ($C_1$-$C_6$)alkyl, halogen, halo ($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)O($C_1$-$C_6$)alkyl, —C(O)$NR^{10}R^{11}$ and —$S(O)_rR^{12}$; wherein $R^{10}$, $R^{11}$, $R^{12}$ and t are as defined above.

10. A compound according to claim 1, wherein Ring B is phenyl; wherein phenyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)O($C_1$-$C_6$)alkyl, —C(O)$NR^{10}R^{11}$ and —$S(O)_rR^{12}$; wherein $R^{10}$, $R^{11}$, $R^{12}$ and t are as defined above.

11. A compound according to claim 1, wherein Ring B is 6- to 10-membered heteroaryl which contains 1, 2 or 3 heteroatoms independently selected from N, O and S, wherein heteroaryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, heterocyclyl, heteroaryl, amino, cyano, nitro, —C(O)$NR^{10}R^{11}$ and —$S(O)_rR^{12}$; wherein $R^{10}$, $R^{11}$, $R^{12}$ and t are as defined above.

12. A compound according to claim 1, wherein Ring B is a 6-membered heteroaryl which contains 1, 2 or 3 N; wherein said heteroaryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, heterocyclyl, heteroaryl, amino, cyano, nitro, —C(O)NR$^{10}$R$^{11}$ and —S(O)$_t$R$^{12}$; wherein R$^{10}$, R$^{11}$, R$^{12}$ and t are as defined above.

13. A compound according to claim 1, wherein Ring C is 6- to 10-membered heteroaryl which contains 1, 2 or 3 heteroatoms independently selected from N, O and S, wherein heteroaryl is unsubstituted or substituted with one or more groups independently selected from the group consisting of (C$_1$-C$_6$)alkyl, halogen, halo(C$_1$-C$_6$)alkyl, hydroxy, (C$_1$-C$_6$)alkoxy, halo(C$_1$-C$_6$)alkoxy, heterocyclyl, heteroaryl, amino, cyano, nitro, —C(O)NR$^{10}$R$^{11}$ and —S(O)$_t$R$^{12}$; wherein R$^{10}$, R$^{11}$, R$^{12}$ and t are as defined above.

14. A compound according to claim 1, wherein Ring C is a 6-membered heteroaryl which contains 1, 2 or 3 N; wherein said heteroaryl is unsubstituted or substituted with one or more groups with one or more groups independently selected from the group consisting of (C$_1$-C$_6$)alkyl, halogen, halo(C$_1$-C$_6$)alkyl, hydroxy, (C$_1$-C$_6$)alkoxy, halo(C$_1$-C$_6$) alkoxy, heterocyclyl, heteroaryl, amino, cyano, nitro, —C(O)NR$^{10}$R$^{11}$ and —S(O)$_t$R$^{12}$; wherein R$^{10}$, R$^{11}$, R$^{12}$ and t are as defined above.

15. A compound according to claim 1, wherein Ring C is (C$_6$-C$_{10}$)aryl; which is unsubstituted or substituted with one or more groups independently selected from the group consisting of (C$_1$-C$_6$)alkyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, heterocyclyl, heteroaryl, amino, cyano, nitro, —C(O)O(C$_1$-C$_6$)alkyl, —C(O)NR$^{10}$R$^{11}$ and —S(O)$_t$R$^{12}$; wherein R$^{10}$, R$^{11}$, R$^{12}$ and t are as defined above.

16. A compound according to claim 1, wherein Ring C is phenyl; wherein phenyl is unsubstituted or substituted with one or more groups independently selected from the group consisting of (C$_1$-C$_6$)alkyl, halogen, halo(C$_1$-C$_6$)alkyl, hydroxy, (C$_1$-C$_6$)alkoxy, halo(C$_1$-C$_6$)alkoxy, (C$_3$-C$_{10}$)cycloalkyl, (C$_6$-C$_{10}$)aryl, heterocyclyl, heteroaryl, amino, cyano, nitro, —C(O)O(C$_1$-C$_6$)alkyl, —C(O)NR$^{10}$R$^{11}$ and —S(O)$_t$R$^{12}$; wherein R$^{10}$, R$^{11}$, R$^{12}$ and t are as defined above.

17. A compound according to claim 1, wherein Ring C is unsubstituted phenyl.

18. A compound according to claim 1, wherein X is —(CR$^8$R$^9$)$_p$—O—, wherein R$^8$, R$^9$ and p are as defined in claim 1.

19. A compound according to claim 1, wherein Y is —(CR$^{14}$R$^{15}$)$_q$—; wherein R$^{14}$ and R$^{15}$ are independently hydrogen or (C$_1$-C$_6$)alkyl.

20. A compound which is
4-(4-((2-(5-(1-Cyanocyclopropyl)thiophen-2-yl)-5-fluorobenzyl)oxy)phenyl)butanoic acid;
3-(4-((2-(5-(1-Cyanocyclopropyl)thiophen-2-yl)-5-fluorobenzyl)oxy)phenyl)propanoic acid;
4-(4-((4-Fluoro-4'-(1-methylcyclopropyl)-[1,1'-biphenyl]-2-yl)methoxy)phenyl)butanoic acid;
4-(4-((4'-(1-Cyanocyclopropyl)-4-fluoro-[1,1'-biphenyl]-2-yl)methoxy)phenyl)butanoic acid;
3-(4-((4'-(1-Cyanocyclopropyl)-4-fluoro-[1,1'-biphenyl]-2-yl)methoxy)phenyl)propanoic acid;
3-(4-((2-(6-(1-Cyanocyclopropyl)pyridin-3-yl)-5-fluorobenzyl)oxy)phenyl)propanoic acid;
4-(4-((4'-Cyclopropyl-4-fluoro-[1,1'-biphenyl]-2-yl)methoxy)phenyl)butanoic acid;
4-(4-((2-(2,3-Dihydro-1H-inden-5-yl)-5-fluorobenzyl)oxy)phenyl)butanoic acid;
4-(4-((5-Fluoro-2-(5,6,7,8-tetrahydronaphthalen-2-yl)benzyl)oxy)phenyl)butanoic acid;
4-(4-((2-(Bicyclo[4.2.0]octa-1(6),2,4-trien-3-yl)-5-fluorobenzyl)oxy)phenyl)butanoic acid;
4-(4-((2-(5-Cyclopropylthiophen-2-yl)-5-fluorobenzyl)oxy)phenyl)butanoic acid;
4-(4-((5-Fluoro-2-(5-(1-hydroxycyclobutyl)thiophen-2-yl)benzyl)oxy)phenyl)butanoic acid;
3-(4-((4-Fluoro-4'-(oxetan-3-yl)-[1,1'-biphenyl]-2-yl)methoxy)phenyl)propanoic acid;
3-(4-((4-Fluoro-4'-(1-hydroxycyclobutyl)-[1,1'-biphenyl]-2-yl)methoxy)phenyl)propanoic acid;
3-(4-((4'-(5,5-Dimethylcyclopent-1-en-1-yl)-4-fluoro-[1,1'-biphenyl]-2-yl)methoxy)phenyl)propanoic acid;
4-(4-((4'-Cyclohexyl-4-fluoro-[1,1'-biphenyl]-2-yl)methoxy)phenyl)butanoic acid;
3-(4-((5-Fluoro-2-(6-(oxetan-3-yl)pyridin-3-yl)benzyl)oxy)phenyl)propanoic acid;
3-(5-((4'-(1-Cyanocyclopropyl)-4-fluoro-[1,1'-biphenyl]-2-yl)methoxy)pyridin-2-yl)propanoic acid;
4-(4-((4-(4-(1-Cyanocyclopropyl)phenyl)pyridin-3-yl)methoxy)phenyl)butanoic acid;
3-(5-((2-(Bicyclo[4.2.0]octa-1(6),2,4-trien-3-yl)-5-fluorobenzyl)oxy)pyridin-2-yl)propanoic acid;
3-(4-((2-(4-(1-Cyanocyclopropyl)phenyl)pyridin-3-yl)methoxy)phenyl)propanoic acid;
4-(4-((2-(2,3-Dihydrobenzofuran-5-yl)-5-fluorobenzyl)oxy)phenyl)butanoic acid;
4-(4-((5-Fluoro-2-(4,5,6,7-tetrahydrobenzo[b]thiophen-2-yl)benzyl)oxy)phenyl)butanoic acid;
4-(4-((2-(6,7-Dihydro-5H-cyclopenta[b]pyridin-3-yl)-5-fluorobenzyl)oxy)phenyl)butanoic acid;
4-(4-((5-Fluoro-2-(7-methylene-4,5,6,7-tetrahydrobenzo[d]thiazol-2-yl)benzyl)oxy)phenyl)butanoic acid;
4-(4-((2-(Bicyclo[4.2.0]octa-1(6),2,4-trien-3-yl)benzyl)oxy)phenyl)butanoic acid;
4-(4-((2-(5,6,7,8-Tetrahydronaphthalen-2-yl)benzyl)oxy)phenyl)butanoic acid;
4-(4-((2-(5-Cyclobutylthiophen-2-yl)-5-fluorobenzyl)oxy)phenyl)butanoic acid;
4-(4-((4'-Cyclopropyl-4-fluoro-3'-methyl-[1,1'-biphenyl]-2-yl)methoxy)phenyl)butanoic acid;
4-(4-((2-(6-Cyclopropylpyridin-3-yl)-5-fluorobenzyl)oxy)phenyl)butanoic acid;
4-(4-((2-(2-Cyclopropylpyrimidin-5-yl)-5-fluorobenzyl)oxy)phenyl)butanoic acid;
4-(4-((2-(4-Cyclopropylthiazol-5-yl)-5-fluorobenzyl)oxy)phenyl)butanoic acid;
4-(4-((2-(2,3-Dihydro-1H-inden-5-yl)benzyl)oxy)phenyl)butanoic acid;
4-(4-((5-Fluoro-2-(5-oxo-5,6,7,8-tetrahydronaphthalen-2-yl)benzyl)oxy)phenyl)butanoic acid;
4-(4-((2-(7,8-Dihydronaphthalen-2-yl)-5-fluorobenzyl)oxy)phenyl)butanoic acid;
4-(4-((5-Fluoro-2-(5-methylene-5,6,7,8-tetrahydronaphthalen-2-yl)benzyl)oxy)phenyl)butanoic acid;
4-(4-((5-Fluoro-2-(5-methyl-7,8-dihydronaphthalen-2-yl)benzyl)oxy)phenyl)butanoic acid;
4-(4-((5-Fluoro-2-(5-methoxy-5,6,7,8-tetrahydronaphthalen-2-yl)benzyl)oxy)phenyl)butanoic acid;
4-(4-((5-Fluoro-2-(5-methoxy-5-methyl-5,6,7,8-tetrahydronaphthalen-2-yl)benzyl)oxy)phenyl)butanoic acid;
4-(4-((5-Fluoro-2-(5-(1-methylcyclopropyl)thiophen-2-yl)benzyl)oxy)phenyl)butanoic acid;
4-(4-((5-Fluoro-2-(5,6,7,8-tetrahydro-4H-cyclohepta[d]thiazol-2-yl)benzyl)oxy)phenyl)butanoic acid;
4-(4-((5-Fluoro-2-(5-(1-fluorocyclopropyl)thiophen-2-yl)benzyl)oxy)phenyl)butanoic acid;

4-(4-((4'-(2,2-Difluorocyclopropyl)-4-fluoro-[1,1'-biphenyl]-2-yl)methoxy)phenyl)butanoic acid;
4-(4-((2-(5-Cyclopropyl-1,3,4-thiadiazol-2-yl)-5-fluorobenzyl)oxy)phenyl)butanoic acid;
4-(4-((2-(5-Cyclopropylthiazol-2-yl)-5-fluorobenzyl)oxy)phenyl)butanoic acid;
4-(4-((5-Fluoro-2-(4,5,6,7-tetrahydrobenzo[d]thiazol-2-yl)benzyl)oxy)phenyl)butanoic acid;
4-(4-((2-(5,6-Dihydro-4H-cyclopenta[d]thiazol-2-yl)-5-fluorobenzyl)oxy)phenyl)butanoic acid;
4-(4-((2-(6,7-Dihydro-4H-pyrano[4,3-d]thiazol-2-yl)-5-fluorobenzyl)oxy)phenyl)butanoic acid;
4-(4-((2-(6,7-Dihydro-4H-pyrano[4,3-d]thiazol-2-yl)-5-fluorobenzyl)oxy)phenyl)butanoic acid;
4-(4-((2-(4-Cyclopropylthiazol-2-yl)-5-fluorobenzyl)oxy)phenyl)butanoic acid;
4-(5-((5-Fluoro-2-(5,6,7,8-tetrahydronaphthalen-2-yl)benzyl)oxy)pyridin-2-yl)butanoic acid;
4-(5-((2-(2,3-Dihydrobenzofuran-5-yl)-5-fluorobenzyl)oxy)pyridin-2-yl)butanoic acid;
4-(5-((5-Fluoro-2-(6-methoxypyridin-3-yl)benzyl)oxy)pyridin-2-yl)butanoic acid;
4-(5-((4'-Cyclopropyl-4-fluoro-[1,1'-biphenyl]-2-yl)methoxy)pyridin-2-yl)butanoic acid;
4-(5-((5-Fluoro-2-(5-methylthiophen-2-yl)benzyl)oxy)pyridin-2-yl)butanoic acid;
4-(5-((2-(Bicyclo[4.2.0]octa-1(6),2,4-trien-3-yl)-5-fluorobenzyl)oxy)pyridine-2-yl)butanoic acid;
4-(5-((4'-(1-cyanocyclopropyl)-4-fluoro-[1,1'-biphenyl]-2-yl)methoxy)pyridin-2-yl)butanoic acid;
4-(5-((5-fluoro-2-(4,5,6,7-tetrahydrobenzo[d]thiazol-2-yl)benzyl)oxy)pyridin-2-yl)butanoic acid;
4-(5-((5-fluoro-2-(5-(1-methylcyclopropyl)thiophen-2-yl)benzyl)oxy)pyridin-2-yl)butanoic acid; or
4-(5-((4-fluoro-2-(4,5,6,7-tetrahydrobenzo[d]thiazol-2-yl)benzyl)oxy)pyridin-2-yl)butanoic acid; and
4-(5-((2-(5-cyclopropylthiophen-2-yl)-4-fluorobenzyl)oxy)pyridin-2-yl)butanoic acid
or a stereoisomer, a tautomer or a geometrical isomer thereof; or a pharmaceutically acceptable salt, a pharmaceutically acceptable solvate thereof.

21. A pharmaceutical composition comprising a therapeutically effective amount of a compound of Formula (I) according to claim 1, or a stereoisomer, a tautomer, a geometrical isomer, a pharmaceutically acceptable salt or a pharmaceutically acceptable solvate thereof; and at least one pharmaceutically acceptable carrier or excipient.

22. A compound according to claim 1, wherein Ring A is a 6- to 10-membered aromatic carbocycle; a 5- or 6-membered heteroaryl or a 5- or 6-membered heterocyclyl wherein heteroaryl and heterocyclyl contain 1, 2 or 3 heteroatoms independently selected from the group consisting of N, O and S;
wherein
the aromatic carbocycle, heteroaryl or heterocyclyl is substituted with $R^1$; wherein $R^1$ is

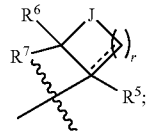

wherein

⸎ is point of attachment to Ring A;
J is —$CH_2$—, —CHF—, —$CF_2$—, —CH[($C_1$-$C_6$)alkyl], —C[($C_1$-$C_6$)alkyl]$_2$;
r is 0, 1, 2, 3, or 4, "-----" represents a bond, and the remaining variables are defined as in claim 1.

23. A compound according to claim 1, wherein $R^1$ and $R^2$ are combined together with one or two atoms of Ring A to form a 3- to 8-membered partly unsaturated or saturated carbocycle;
wherein the said carbocycle can be unsubstituted or substituted with the one or more groups independently selected from the group consisting of ($C_1$-$C_6$)alkenyl, ($C_1$-$C_6$)alkyl, halo($C_1$-$C_6$)alkoxy, hydroxy, halogen, cyano, oxo, ($C_3$-$C_{10}$)cycloalkyl, ($C_6$-$C_{10}$)aryl, heteroaryl and heterocyclyl; and
wherein Ring A together with $R^1$ and $R^2$ does not form an unsubstituted tetrahydronaphthyl group.

24. A pharmaceutical composition comprising a therapeutically effective amount of a compound of Formula (I) according to claim 20, or a stereoisomer, a tautomer, a geometrical isomer, a pharmaceutically acceptable salt or a pharmaceutically acceptable solvate thereof; and at least one pharmaceutically acceptable carrier or excipient.

25. The compound of claim 22, wherein $R^5$, $R^6$, $R^7$ are hydrogen, J is —$CH_2$—, and r is 0.

26. A compound according to claim 23, wherein $R^1$ and $R^2$ are combined together with one or two atoms of Ring A to form a 3- to 8-membered partly unsaturated or saturated carbocycle, and
wherein Ring A together with $R^1$ and $R^2$ does not form an unsubstituted tetrahydronaphthyl group.

27. The compound of claim 22, wherein Ring A is a 5- or 6-membered heteroaryl containing 1, 2 or 3 heteroatoms independently selected from the group consisting of N, O and S; wherein
heteroaryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, heterocyclyl, heteroaryl, amino, cyano, nitro, —C(O)$NR^{10}R^{11}$ and —S(O)$_tR^{12}$; wherein $R^{10}$, $R^{11}$, $R^{12}$ and t are as defined above;
heterocyclyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)$NR^{10}R^{11}$ and —S(O)$_tR^{12}$; wherein $R^{10}$, $R^{11}$, $R^{12}$ and t are as defined above.

28. The compound of claim 23, wherein Ring A is a 5- or 6-membered heteroaryl containing 1, 2 or 3 heteroatoms independently selected from the group consisting of N, O and S; wherein
heteroaryl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, heterocyclyl, heteroaryl, amino, cyano, nitro, —C(O)$NR^{10}R^{11}$ and —S(O)$_tR^{12}$; wherein $R^{10}$, $R^{11}$, $R^{12}$ and t are as defined above;
heterocyclyl is unsubstituted or substituted with one or more groups independently selected from the group consisting of ($C_1$-$C_6$)alkyl, halogen, halo($C_1$-$C_6$)alkyl, hydroxy, ($C_1$-$C_6$)alkoxy, halo($C_1$-$C_6$)alkoxy, ($C_3$-$C_{10}$)cycloalkyl, ($C_6$-$C_{10}$)aryl, heterocyclyl, heteroaryl, amino, cyano, nitro, —C(O)$NR^{10}R^{11}$ and —S(O)$_tR^{12}$; wherein $R^{10}$, $R^{11}$, $R^{12}$ and t are as defined above.

* * * * *

UNITED STATES PATENT AND TRADEMARK OFFICE
CERTIFICATE OF CORRECTION

PATENT NO. : 10,227,360 B2
APPLICATION NO. : 15/117430
DATED : March 12, 2019
INVENTOR(S) : Sanjay Kumar et al.

It is certified that error appears in the above-identified patent and that said Letters Patent is hereby corrected as shown below:

In the Claims

In Column 90, Claim 1, Line 18, add "—" to "$(CR^8R^9)_p$-S-", resulting in "—$(CR^8R^9)_p$-S-".

In Column 98, Claim 23, Line 10, remove "halo($C_1$-$C_6$)alkoxy," and add "halo($C_1$-$C_6$)alkyl, ($C_1$-$C_6$)alkoxy,".

Signed and Sealed this
Seventeenth Day of March, 2020

Andrei Iancu
*Director of the United States Patent and Trademark Office*